(12) United States Patent
Hollingsworth et al.

(10) Patent No.: US 7,390,825 B1
(45) Date of Patent: Jun. 24, 2008

(54) PROCESS FOR THE PREPARATION OF OXAZOLIDINONES AND METHOD OF USE THEREOF

(75) Inventors: Rawle I. Hollingsworth, Haslett, MI (US); Guijun Wang, New Orleans, LA (US); Raghavakaimal Padmakumar, Dayton, NJ (US); Jianmin Mao, North Brunswick, NJ (US); Huiping Zhang, Bellemead, NJ (US); Zongmin Dai, Chicago, IL (US); Kanakamma Puthuparampil, Plainsboro, NJ (US)

(73) Assignee: Board of Trustees of Michigan State University, East Lansing, MI (US)

( * ) Notice: Subject to any disclaimer, the term of this patent is extended or adjusted under 35 U.S.C. 154(b) by 783 days.

(21) Appl. No.: 10/272,877

(22) Filed: Oct. 17, 2002

Related U.S. Application Data

(60) Provisional application No. 60/330,266, filed on Oct. 18, 2001, provisional application No. 60/330,268, filed on Oct. 18, 2001.

(51) Int. Cl.
*A01N 43/76* (2006.01)
(52) U.S. Cl. ...................... 514/376; 544/369; 546/271.7
(58) Field of Classification Search ........................ None
See application file for complete search history.

(56) References Cited

FOREIGN PATENT DOCUMENTS

| EP | 0 050 827 | 5/1982 |
|---|---|---|
| EP | 0 064 294 | 11/1982 |
| EP | 0 101 076 | 2/1984 |
| EP | 0 138 539 | 4/1985 |
| EP | 0 184 170 | 6/1986 |
| GB | 1085106 | * 9/1967 |
| WO | WO 99/37630 | 7/1999 |
| WO | WO 01/47919 | 7/2001 |

OTHER PUBLICATIONS

Park et al. "Antibacterials. Synthesis and Structure-Activity Studies of 3-Aryl-2oxooxazolidines. 4. Multiply-Substituted Aryl Derivatives" J. Med. Chem. 1992, 35, 1156-1165.*

Seneci, Pierfausto et al., "Synthesis and antimicrobialactivity of oxazolidinonesand relalted heterocycles" Journal of the Chemical Society, Perkin Transactions 1: Organic and Bio-Organic Chemistry, (1972-1999)(1994)(16)2345-51.

* cited by examiner

*Primary Examiner*—Jon D. Epperson
(74) *Attorney, Agent, or Firm*—Ian C. McLeod

(57) ABSTRACT

Substituted oxazolidinone of the formula:

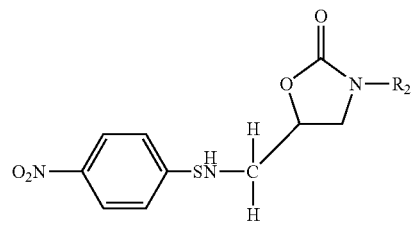

wherein $R_2$ is alkyl selected from the group consisting of methyl, ethyl, and isopropyl moieties, are described. The compounds are antibacterial.

5 Claims, 4 Drawing Sheets

Peak 1

Peak 2

Peak 3

Peak 4

Peak 5

Peak 6

Peak 7

Peak 8

Peak 9

Peak 10

PROCESS FOR THE PREPARATION OF OXAZOLIDINONES AND METHOD OF USE THEREOF

CROSS-REFERENCE TO RELATED APPLICATION

This application claims priority to U.S. Provisional Application No. 60/330,266 filed Oct. 18, 2001, and U.S. Provisional Application No. 60/330,268 filed Oct. 18, 2001.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a process for preparing N-(substituted)-C-(substituted methyl)-oxazolidinones, C-(substituted methyl)-oxazolidinones, and N-(substituted)-C-(substituted methyl)-oxazolidinones, preferably chiral, from optically active C-(protected oxymethyl)-oxazolidinones. The process can be used to produce combinatorial libraries of the above substituted oxazolidinones in a two or three step reaction comprising a plurality of reagents differing in numbers of carbons or particular substituted oxazolidinones. A number of substituted oxazolidinones produced using the above process have been discovered to have antimicrobial activity.

(2) Description of Related Art

Oxazolidinones, particularly substituted oxazolidinones such as 3-(substituted)-5-alkylaminomethyl- and 3-(substituted)-5-acylaminomethyl-2-oxazolidinones, are an important class of drug substances which are used for a wide variety of drug applications. These applications include use as antibacterial agents and in therapies for treating behavior disorders (Bowersock et al., Antimicrob. Agents Chemotherp. 44: 1367-1369 (2000); Skold, Acta Vet. Scand. Suppl. 93: 23-36 (2000); Diekema and Jones, Drugs 59: 7-16 (2000); Genin et al., J. Med. Chem. 43: 953-970 (2000); Johnson et al., J. Antimicrob. Chemother. 45: 225-230 (2000); Schulin et al., Antimicrob. Agents Chemotherp. 43: 2873-2876 (1999); Cynamon et al., Antimicrob. Agents Chemotherp. 43: 1189-1191 (1999); Chen and Reamer, Organic Letts. 1: 293-294 (1999); Brenner et al., Clin Therapeut. 22: 411-419 (2000); Clemett and Markham, Drugs 59: 815-827 (2000); Brickner et al., J. Med. Chem. 39: 673-679 (1996); Barry, Antimicrob. Agents Chemotherp. 32: 150-152 (1988); Slee et al., Antimicrob. Agents Chemotherp. 31: 1791-1797 (1987); Manninen et al., Abs. Paps. Amer. Chem. Soc. 212: 389-ORGN, Part 2, (Aug. 25, 1996)).

There are several methods for making the oxazolidinone nucleus in 3-(substituted)-5-alkylaminomethyl- and 3-(substituted)-5-acylaminomethyl-2-oxazolidinones. The general structure of 3-(substituted)-5-(substituted methyl)-2-oxazolidinone is

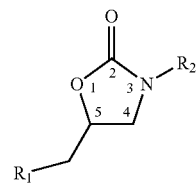

wherein $R_1$ is alkyl, aryl, heteroalkyl, heteroaryl, or mixture thereof, or hydrogen or hydroxy, and $R_2$ is alkyl, aryl, heteroalkyl, heteroaryl, or mixture thereof. The following disclose processes for preparing oxazolidinones and substituted oxazolidinones.

U.S. Pat. No. 6,288,238 B1 to Hollingsworth and Wang disclose a process for preparing 5-hydroxymethyl-2-oxazolidinones in one step from 3,4-boronic acid ester protected 3,4-dihydroxybutyramides.

U.S. Pat. No. 6,288,239 B1 to Hollingsworth and Wang discloses a process for preparing 5-trityloxymethyl-2-oxazolidinones and suggests a scheme for the alkylation of N-lithio-N-substituted carbamates with oxiranes such as glycidyl butyrate as shown in Scheme 1.

Scheme 1

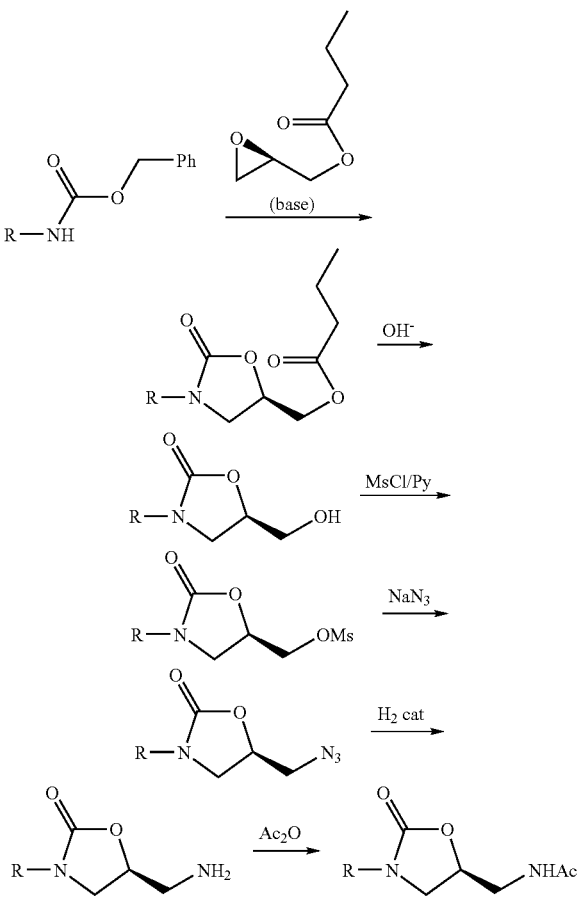

Glycidyl equivalents such as epichlorohydrin can be used instead of glycidyl butyrate.

Schaus and Jacobsen (Tetrahedron Letts. 37: 7937-7940 (1996)) teach using optically active N-oxiranylmethylacetamides to prepare chiral 3-(substituted)-5-acetamidomethyl-2-oxazolidinones in one step by the alkylation of N-lithio-N-aryl (or alkyl) carbamates as shown in Scheme 2.

Scheme 2

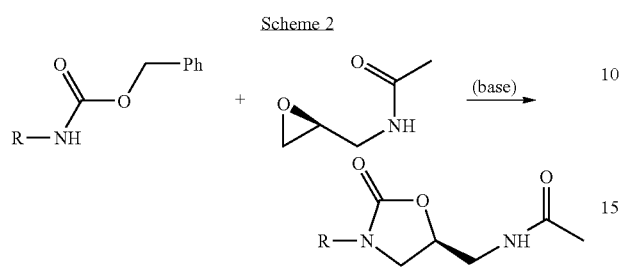

However, the above processes do not allow for the rapid synthesis of a plurality of substituted oxazolidinones at the same time in the same reaction. Thus, producing a plurality of substituted oxazolidinones for drug screening is slow and cumbersome which affects the rate in which new and useful drugs can be discovered. Therefore, there remains a need for a rapid and simple process that can produce a plurality of substituted oxazolidinones at the same time in the same reaction. Being able to produce a plurality of drug candidates in a short period of time would accelerate the rate at which new and useful drugs and other compounds are discovered. The present invention provides a simple and rapid process for synthesizing substituted oxazolidinones.

Strains of Gram positive bacteria resistant to the present repertoire of antibiotics have been increasing in prevalence over the past several decades (Skold, Acta Vet. Scand. Suppl. 93: 23-36 (2000)). Resistant Gram positive that have been commonly encountered include among others those in the staphylococci, streptococci, pneumococci, and enterococci families. Because of the increasing prevalence of these antibiotic resistant bacterial strains, there is a clear need for new antimicrobial agents.

Several species of substituted oxazolidinones have been discovered to be effective antimicrobial agents against particular antibiotic resistant strains of Gram positive bacteria. Linezolid (Clemett and Markham, Drugs 59: 815-827 (2000); Johnson et al., J. Antimicrob. Chemother. 45: 225-230 (2000)) is a substituted oxazolidinone which has been approved for the treatment of microbial infections. The structure of linezolid is shown below.

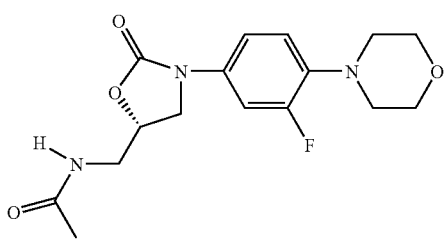

A number of other substituted oxazolidinones with varying degrees of antibacterial activity against Gram positive and in some cases Gram negative bacteria are also known (Barry, Antimicrob. Agents Chemotherp. 32: 150-152 (1988); Brickner et al., J. Med. Chem. 39: 673-679 (1996); Genin et al., J. Med. Chem. 43: 953-970 (2000); Slee et al., Antimicrob. Agents Chemotherp. 31: 1791-1797 (1987)).

Most, if not all, of the known substituted oxazolidinones which have been found to have antibacterial activity have the structure shown below wherein the $R_3$ substituent is aryl and the relative stereochemistries of the groups on the chiral center (C-5) is as indicated.

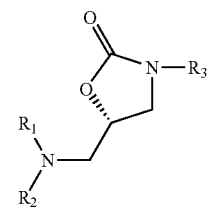

A comparison of the structures for all of the known substituted oxazolidinones which have antimicrobial activity, the general consensus has arisen that there are at least three elements of these substituted oxazolidinones which are critical for biological activity. The first element is that when the oxazolidinone ring is oriented as shown below such that all the ring atoms are in one plane, the carbonyl oxygen points up, the ring nitrogen is to the left, and the 5-substituent is to the right, then of the two possible orientations for the 5-substituent (distal or proximal), the proximal substituent is required for biological activity.

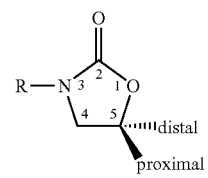

The second element is that the 3-substituent is an aryl. The third element is that the 5-substituent is an alkylamino methyl or an acetamidomethyl group. No substituted oxazolidinone which has antibacterial activity has been found which does not have all three of the above elements.

Because microorganisms will eventually develop resistance to antibiotics, there is a continual need for new antibiotics. The present invention provides families of novel substituted oxazolidinones which have antimicrobial activity but which have structures which do not conform to the consensus structure thought to be necessary for antimicrobial activity.

SUMMARY OF THE INVENTION

The present invention provides a process for preparing N-(substituted)-C-(substituted methyl)-oxazolidinones, C-(substituted methyl)-oxazolidinones, and N-(substituted)-C-(substituted methyl)-oxazolidinones, preferably chiral, from optically active C-(protected oxymethyl)-oxazolidinones. The process can be used to produce combinatorial libraries of the above substituted oxazolidinones in a two or three step reaction comprising a plurality of reagents differing in numbers of carbons or particular substituted oxazolidinones.

Therefore, the present invention provides a process for producing a library of substituted oxazolidinones which comprises (a) reacting a C-(protected oxymethyl)-oxazolidinone in an anhydrous organic solvent containing a first reagent including a plurality of compounds having different numbers of carbons which are reactive with N in the C-(protected oxymethyl)-oxazolidinone under alkylation or Buchwald conditions in an inert atmosphere to produce a mixture of N-(substituted)-C-(protected oxymethyl)-oxazolidinones (I); and (b) reacting the mixture of (I) produced in step (a) in an aqueous organic solvent with a second reagent which removes the protecting group and replaces it with another group from the second reagent to produce the library of substituted oxazolidinones.

In a further embodiment of the above process, the second reagent is a reducing agent which removes the protecting group of the N-(substituted)-C-(protected oxymethyl)-oxazolidinone to provide a mixture of N-(substituted)-C-hydroxymethyl-oxazolidinones (II) as the library of substituted oxazolidinones.

In a further embodiment of the above process, the mixture of (II) is further reacted with a third reagent containing a plurality of compounds reactive with the hydroxymethyl in an anhydrous organic solvent to produce a mixture of N-(substituted)-C-(substituted methyl)-oxazolidinones (III) as the library of substituted oxazolidinones. Preferably, the anhydrous organic solvent further includes pyridine. In particular embodiments, the third reagent produces a mixture of 3-(substituted)-5-(substituted methyl)-2-oxazolidinones or a mixture of 3-(substituted)-4-(substituted methyl)-2-oxazolidinones.

The present invention further provides a process for producing a library of substituted oxazolidinones which comprises (a) reacting a C-(protected oxymethyl)-oxazolidinone in an anhydrous organic solvent containing a first reagent including a plurality of compounds having different numbers of carbons which are reactive with N in the C-(protected oxymethyl)-oxazolidinone under alkylation or Buchwald conditions in an inert atmosphere to produce a mixture of N-(substituted)-C-(protected oxymethyl)-oxazolidinones (I); (b) reacting the mixture of (I) produced in step (a) in an aqueous organic solvent with a second reagent which removes the protecting group of the N-(substituted)-C-(protected oxymethyl)-oxazolidinones to produce a mixture of N-(substituted)-C-hydroxymethyl-oxazolidinones (II); and c) reacting the mixture of (II) produced in step (b) in an anhydrous organic solvent with a third reagent containing a plurality of compounds reactive with the hydroxymethyl of the mixture of (II) to produce a mixture of N-(substituted)-C-(substituted methyl)-oxazolidinones (III) as the library of substituted oxazolidinones. Preferably, the anhydrous organic solvent in step (c) further includes pyridine. In particular embodiments, the third reagent produces a mixture of 3-(substituted)-5-(substituted methyl)-2-oxazolidinones or a mixture of 3-(substituted)-4-(substituted methyl)-2-oxazolidinones.

In a further embodiment of the above processes, substituted is selected from the group consisting of acyl, alkyl, aryl, aryl sulfonyl, heteroalkyl, heteroaryl, cycle, heterocycle, thio, and mixtures thereof.

In a further embodiment of the above processes, the substituted oxazolidinones in the library are separated chromatographically.

In a preferred embodiment of the above process, the protecting group is a trityl group.

In a further embodiment of the above processes, under the alkylation conditions in step (a) the anhydrous organic solvent further includes an alkali without substantial reducing activity, preferably, the alkali is an ionic hydride, most preferably, the ionic hydride is sodium hydride, and under the Buchwald conditions in step (a) the anhydrous organic solvent further includes a palladium catalyst, preferably, the palladium catalyst is Pd(OAc) 2.

In a further embodiment of the above processes, the mixture of N-(substituted)-C-(protected oxymethyl)-oxazolidinones (I) produced in step (a) are purified by extracting the reaction mixture with the organic solvent, drying over a drying agent, and then removing the solvent.

In a still further embodiment of the above processes, the N-(substituted)-C-hydroxymethyl-oxazolidinones (II) produced in step (b) are purified by removing the solvent.

In a still further embodiment of the above processes, the N-(substituted)-C-(substituted methyl)-oxazolidinones (III) produced in step (c) are purified by extracting the reaction mixture with the organic solvent, drying over a drying agent, and then removing the solvent.

In a further embodiment of the above processes, the present invention provides a process for preparing a library of substituted oxazolidinones which comprises reacting a C-hydroxymethyl-oxazolidinone in an anhydrous organic solvent including pyridine with a reagent containing a plurality of compounds reactive with the hydroxy group to produce a mixture of substituted oxazolidinones as the library of substituted oxazolidinones.

In a further embodiment of the above processes, the reaction produces a mixture of 5-(substituted methyl)-2-oxazolidinones, a mixture of 4-(substituted methyl)-2-oxazolidinones, a mixture of N-(substituted)-C-(hydroxymethyl)-2-oxazolidinones, or a mixture of N-(substituted)-C-(substituted methyl)-2-oxazolidinones.

In a further embodiment of the above processes, substituted is selected from the group consisting of acyl, alkyl, aryl, aryl sulfonyl, heteroalkyl, heteroaryl, cycle, heterocycle, thio, and mixtures thereof.

In a further embodiment of the above processes, the substituted oxazolidinones in the library are separated chromatographically.

The present invention further provides a library of substituted oxazolidinones selected from the group consisting of N-(substituted)-C-(substituted methyl)-oxazolidinones, N-(substituted)-C-hydroxymethyl-oxazolidinones, and C-(substituted methyl)-oxazolidinones.

In a further embodiment of the library, substituted in N-(substituted) includes at least 10 different individual groups.

In a further embodiment of the library, substituted in C-(substituted) includes at least 10 different individual groups.

In a further embodiment of the library, the library is a mixture of N-(substituted)-C-hydroxymethyl-2-oxazolidinones or a mixture selected from the group consisting of 3-(substituted)-5-(substituted methyl)-2-oxazolidinones and 3-(substituted)-4-(substituted methyl)-2-oxazolidinones.

In a further embodiment of the library, substituted is selected from the group consisting of acyl, alkyl, aryl, aryl sulfonyl, heteroalkyl, heteroaryl, cycle, heterocycle, thio, and mixtures thereof.

The present invention further provides a method of screening substituted oxazolidinones for biological activity which comprises (a) providing a library of the substituted oxazolidinones wherein the substituted oxazolidinones are selected from the group consisting of N-(substituted)-C-(substituted methyl)-oxazolidinones, N-(substituted)-C-hydroxymethyl-oxazolidinones, and C-(substituted methyl)-oxazolidinones; (b) chromatographically separating the substituted oxazolidinones in the library; and (c) testing the separated substituted oxazolidinones for the biological activity.

In a further embodiment of the above method, substituted in N-(substituted) includes at least 10 different individual groups.

In a further embodiment of the above method, substituted in C-(substituted methyl) includes at least 10 different individual groups.

In a further embodiment of the above method, the substituted oxazolidinones is a mixture of N-(substituted)-C-hydroxymethyl-2-oxazolidinones or a mixture selected from the group consisting of 3-(substituted)-5-(substituted methyl)-2-oxazolidinones, 3-(substituted)-4-(substituted methyl)-2-oxazolidinones, 5-(substituted methyl)-2-oxazolidinones, and 4-(substituted methyl)-2-oxazolidinones.

In a further embodiment of the above method, substituted is selected from the group consisting of acyl, alkyl, aryl, aryl sulfonyl, heteroalkyl, heteroaryl, cycle, heterocycle, thio, and mixtures thereof.

The present invention further provides a substituted oxazolidinone with biological activity obtained by the above method.

The present invention further provides a process for producing a substituted oxazolidinone which comprises (a) reacting a C-(protected oxymethyl)-oxazolidinone in an anhydrous organic solvent containing a first reagent including a compound which is reactive with N in the C-(protected oxymethyl)-oxazolidinone under alkylation or Buchwald conditions in an inert atmosphere to produce an N-(substituted)-C-(protected oxymethyl)-oxazolidinone; (b) reacting the N-(substituted)-C-(protected oxymethyl)-oxazolidinone in an aqueous organic solvent with a second reagent with a second reagent which replaces the protecting group of the N-(substituted)-C-(protected oxymethyl)-oxazolidinone with a hydrogen to produce an N-(substituted)-C-hydroxymethyl-oxazolidinone; and (c) reacting the N-(substituted)-C-hydroxymethyl-oxazolidinone in an anhydrous organic solvent with a third reagent containing a compound reactive with the hydroxy group to produce N-(substituted)-C-(substituted methyl)-oxazolidinones as the substituted oxazolidinone.

In a further embodiment of the above process, the anhydrous organic solvent in step (c) further includes pyridine.

In a further embodiment of the above process, substituted is selected from the group consisting of acyl, alkyl, aryl, aryl sulfonyl, heteroalkyl, heteroaryl, cycle, heterocycle, thio, and mixtures thereof.

In a further embodiment of the above process, the protecting group is a trityl group.

In a further embodiment of the above process, the substituted oxazolidinone has the formula

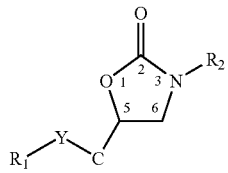

wherein $R_1$ is selected from the group consisting of hydrogen, acyl, alkyl, aryl, heteroalkyl, heteroaryl, heterocycle, phenacyl, aryl sulfonyl, thio, and mixture thereof, or a hydrogen; $R_2$ is selected from the group consisting of acyl, alkyl, aryl, heteroalkyl, heteroaryl, heterocycle, aryl sulfonyl, phenacyl, thio, and mixture thereof, or a hydrogen, wherein hetero is an atom selected from the group consisting of O, N, P, and S; and y is a heteroatom selected from the group consisting of O, N, and S.

In a further embodiment of the above process, the substituted oxazolidinone has the formula

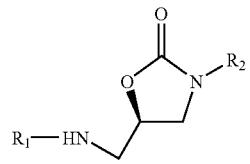

wherein $R_1$ is selected from the group consisting of alkyl sulfonyl, aryl sulfonyl, alkyl, acyl, aryl, and thio and $R_2$ is selected from the group consisting of alkyl, acyl, aryl, and thio; or, the substituted oxazolidinone has the formula

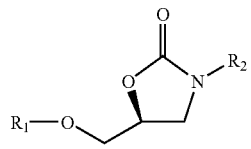

wherein $R_1$ is selected from the group consisting of alkyl sulfonyl, aryl sulfonyl, alkyl, acyl, aryl, and thio and $R_2$ is selected from the group consisting of alkyl, acyl, aryl, and thio; or, the substituted oxazolidinone has the formula

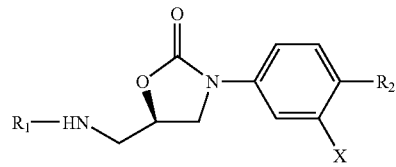

wherein $R_1$ is selected from the group consisting of alkyl, acyl, thio, and aryl, $R_2$ is selected from the group consisting of C-3, C-4, and C-5 chiral synthons with 1, 2, or 3 chiral centers, and X is selected from the group consisting of F, $NO_2$, Cl, alkyl, and aryl; or, the substituted oxazolidinone has the formula

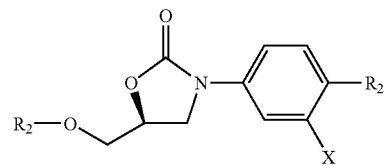

wherein $R_1$ is selected from the group consisting of alkyl, acyl, thio, and aryl, $R_2$ is selected from the group consisting of C-3, C-4, and C-5 chiral synthons with 1, 2, or 3 chiral centers, and X is selected from the group consisting of F, $NO_2$, Cl, alkyl, and aryl; or, the substituted oxazolidinone has the formula

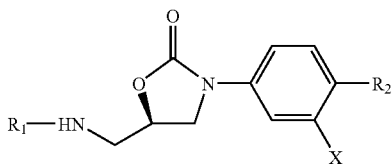

wherein $R_1$ is selected from the group consisting of C-3, C-4, and C-5 chiral synthons with 1, 2, or 3 chiral centers, R2 is selected from the group consisting of alkyl, aryl, acyl, thio, and heterocycle, and X is selected from the group consisting of F, $NO_2$, Cl, alkyl, and aryl; or, the substituted oxazolidinone has the formula

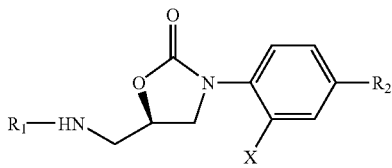

wherein $R_1$ is selected from the group consisting of alkyl, aryl, acyl, thio, or heterocycle, $R_2$ is selected from the group consisting of C-3, C-4, and C-5 chiral synthons with 1, 2, or 3 chiral centers, and X is selected from the group consisting of F, $NO_2$, Cl, alkyl, and aryl; or, the substituted oxazolidinone has the formula

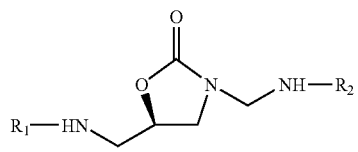

wherein $R_1$ is selected from the group consisting of alkyl, aryl, acyl, thio, and heterocycle and $R_2$ is selected from the group consisting of C-3, C-4, and C-5 chiral synthons with 1, 2, or 3 chiral centers; or, the substituted oxazolidinone has the formula

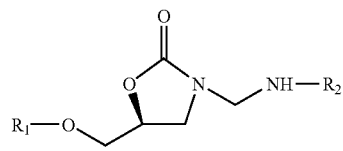

wherein $R_1$ is selected from the group consisting of alkyl, aryl, acyl, thio, and heterocycle and $R_2$ is selected from the group consisting of C-3, C-4, with C-5 chiral synthons with 1, 2, or 3 chiral centers.

In a further embodiment of the above process, under the alkylation conditions in step (a) the anhydrous organic solvent further includes an alkali without substantial reducing activity, preferably, the alkali is an ionic hydride, most preferably, the ionic hydride is sodium hydride.

In a further embodiment of the above process, under the Buchwald conditions in step (a) the anhydrous organic solvent further includes a palladium catalyst, preferably, the palladium catalyst is $Pd(OAc)_2$.

In a further embodiment of the above process, the mixture of N-(substituted)-C-(protected oxymethyl)-oxazolidinone produced in step (a) is purified by extracting the reaction mixture with the organic solvent, drying over a drying agent, and then removing the solvent.

In a further embodiment of the above process, the N-(substituted)-C-hydroxymethyl-oxazolidinone produced in step (b) is purified by removing the solvent.

In a further embodiment of the above process, the N-(substituted)-C-(substituted methyl)-oxazolidinone produced in step (c) is purified by extracting the reaction mixture with the organic solvent, drying over a drying agent, and then removing the solvent.

The present invention further provides a substituted oxazolidinone which has the formula

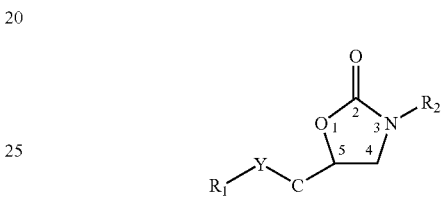

wherein $R_1$ is selected from the group consisting of hydrogen, acyl, alkyl, aryl, heteroalkyl, heteroaryl, heterocycle, phenacyl, aryl sulfonyl, thio, and mixture thereof, or a hydrogen; $R_2$ is selected from the group consisting of acyl, alkyl, aryl, heteroalkyl, heteroaryl, heterocycle, aryl sulfonyl, phenacyl, thio, and mixture thereof, or a hydrogen, wherein hetero is an atom selected from the group consisting of O, N, P, and S; and y is a heteroatom selected from the group consisting of O, N, and S.

The present invention further provides a substituted oxazolidinone which has the formula

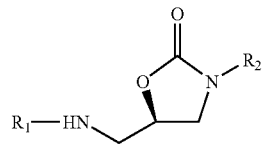

wherein $R_1$ is selected from the group consisting of alkyl sulfonyl, aryl sulfonyl, alkyl, acyl, aryl, and thio and $R_2$ is selected from the group consisting of alkyl, acyl, aryl, and thio; or, a substituted oxazolidinone which has the formula

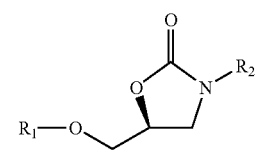

wherein $R_1$ is selected from the group consisting of alkyl sulfonyl, aryl sulfonyl, alkyl, acyl, aryl, and thio and $R_2$ is selected from the group consisting of alkyl, acyl, aryl, and thio; or, a substituted oxazolidinone which has the formula

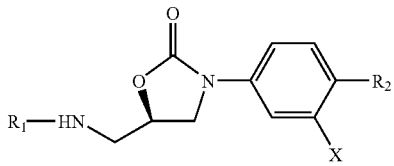

wherein R₁ is selected from the group consisting of alkyl, acyl, thio, and aryl, R₂ is selected from the group consisting of C-3, C-4, and C-5 chiral synthons with 1, 2, or 3 chiral centers, and X is selected from the group consisting of F, NO₂, Cl, alkyl, and aryl; or, a substituted oxazolidinone which has the formula

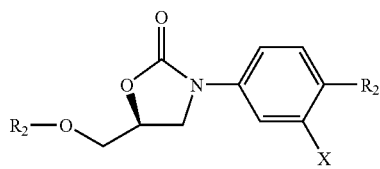

wherein R₁ is selected from the group consisting of alkyl, acyl, thio, and aryl, R₂ is selected from the group consisting of C-3, C-4, and C-5 chiral synthons with 1, 2, or 3 chiral centers, and X is selected from the group consisting of F, NO₂, Cl, alkyl, and aryl; or, a substituted oxazolidinone which has the formula

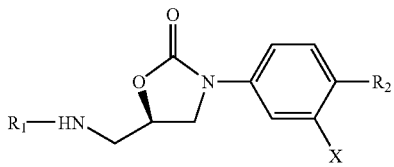

wherein R₁ is selected from the group consisting of C-3, C-4, and C-5 chiral synthons with 1, 2, or 3 chiral centers, R2 is selected from the group consisting of alkyl, aryl, acyl, thio, and heterocycle, and X is selected from the group consisting of F, NO₂, Cl, alkyl, and aryl; or, a substituted oxazolidinone which has the formula

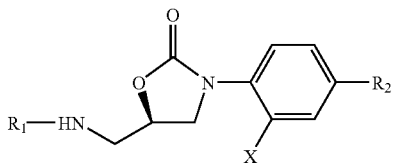

wherein R₁ is selected from the group consisting of alkyl, aryl, acyl, thio, or heterocycle, R₂ is selected from the group consisting of C-3, C-4, and C-5 chiral synthons with 1, 2, or 3 chiral centers, and X is selected from the group consisting of F, NO₂, Cl, alkyl, and aryl; or, a substituted oxazolidinone which has the formula

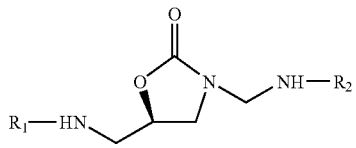

wherein R₁ is selected from the group consisting of alkyl, aryl, acyl, thio, and heterocycle and R₂ is selected from the group consisting of C-3, C-4, and C-5 chiral synthons with 1, 2, or 3 chiral centers; or, a substituted oxazolidinone which has the formula

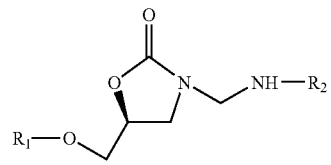

wherein R₁ is selected from the group consisting of alkyl, aryl, acyl, thio, or heterocycle and R₂ is selected from the group consisting of C-3, C-4, with C-5 chiral synthons with 1, 2, or 3 chiral centers.

The present invention further provides an antimicrobial composition comprising a carrier and one or more substituted oxazolidinones of the formula

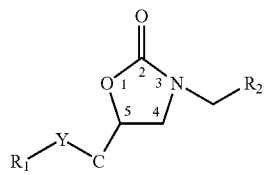

wherein R₁ is selected from the group consisting of hydrogen, acyl, alkyl, aryl, heteroalkyl, heteroaryl, heterocycle, phenacyl, aryl sulfonyl, thio, and mixture thereof, or a hydrogen; R₂ is selected from the group consisting of acyl, alkyl, aryl, heteroalkyl, heteroaryl, heterocycle, aryl sulfonyl, phenacyl, thio, and mixture thereof, or a hydrogen, wherein hetero is an atom selected from the group consisting of O, N, P, and S; and y is a heteroatom selected from the group consisting of O, N, and S.

OBJECTS

Therefore, it is the object of the present invention to provide a process for producing substituted oxazolidinones which are substituted at the N-position or the C-position, or both.

It is a further object of the present invention to provide a process for producing a library of substituted oxazolidinones comprising a plurality of oxazolidinones substituted at the N-position, a plurality of oxazolidinones substituted at the C-position, or a plurality of oxazolidinones substituted at both the N-position and the C-position.

These and other objects of the present invention will become increasingly apparent with reference to the following drawings and preferred embodiments.

DETAILED DESCRIPTION OF THE INVENTION

Figure 1A:
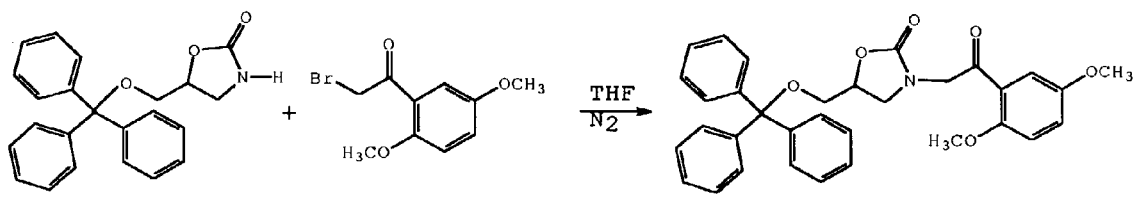
FIG. 1A shows the conversion of 5-trityloxymethyl-2-oxazolidinone to 3-(2,5-dimethoxyphenacyl)-5-trityloxymethyl-2-oxazolidinone.

All patents, patent applications, government publications, government regulations, and literature references cited in this specification are hereby incorporated herein by reference in their entirety. In case of conflict, the present description, including definitions, will control.

The present invention provides a novel process for preparing collections or combinatorial libraries of substituted oxazolidinones. In particular, the present invention provides a process for preparing libraries of optically active or chiral N-(substituted)-C-(substituted methyl)-oxazolidinones, N-(substituted)-C-(methyl)-oxazolidinones, and C-(substituted methyl)-oxazolidinones bearing alkyl or aryl substituents in the N-substituted position (3-position) and a methyl group substituted with a heteroatom such as O, N, or S in the C-substituted position (4- or 5-position) and wherein the heteroatom is further substituted with hydrogen or acyl, alkyl, aryl, heteroalkyl, heteroaryl, heterocycle, phenacyl, aryl sulfonyl, or mixture thereof.

In a preferred embodiment, the substituted oxazolidinones comprising the library are optically active or chiral N-(substituted)-C-(substituted methyl)-2-oxazolidinones, N-(substituted)-C-(methyl)-2-oxazolidinones, and C-(substituted)-2-oxazolidinones bearing alkyl or aryl substituents in the N-substituted position (3-position) and a methyl group substituted with a heteroatom in the C-substituted position (4- or 5-position) and wherein the heteroatom is further substituted with hydrogen or acyl, alkyl, aryl, heteroalkyl, heteroaryl, heterocycle, phenacyl, aryl sulfonyl, or mixture thereof.

As used herein, the term "substituted" refers to groups other than hydrogen substituted at the N-position or the methyl at the C-position. Preferably, the substituting group is an organic group. Therefore, when the N-position is substituted, it is substituted with a group such as acyl, alkyl, aryl, heteroalkyl, heteroaryl, heterocycle, aryl sulfonyl, phenacyl, or mixture thereof. When N is not referred to as being "substituted", the N has a hydrogen at the N-position. When the C-position methyl is substituted, it is referred to as "substituted methyl" wherein "substituted" is a group such as acyl, alkyl, aryl, heteroalkyl, heteroaryl, heterocycle, phenacyl, aryl sulfonyl, or mixture thereof.

The general structure of these substituted oxazolidinones is shown below

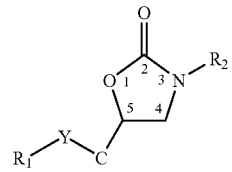

wherein $R_1$ is an acyl, alkyl, aryl, heteroalkyl, heteroaryl, heterocycle, phenacyl, aryl sulfonyl, thio, or mixture thereof, or a hydrogen, $R_2$ is an acyl, alkyl, aryl, heteroalkyl, heteroaryl, heterocycle, aryl sulfonyl, phenacyl, thio, or mixture thereof, or a hydrogen (when N is not substituted by an organic group), and y is a heteroatom selected from the group consisting of O, N, and S. The heteroatom comprising $R_1$ or $R_2$ can include one or more atoms selected from the group consisting of 0, P, S, N, Al, and Si.

The above genus comprises at least eight families of substituted oxazolidinones. The first family (Family I) comprises substituted oxazolidinones with the following general structure

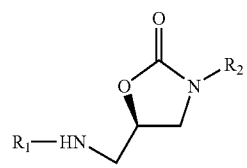

wherein $R_1$ is alkyl sulfonyl, aryl sulfonyl, alkyl, acyl, aryl, or thio and $R_2$ is alkyl, acyl, aryl, or thio.

The second family (Family II) comprises substituted oxazolidinones with the following general structure

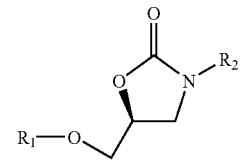

wherein $R_1$ is alkyl sulfonyl, aryl sulfonyl, alkyl, acyl, aryl, or thio and $R_2$ is alkyl, acyl, aryl, or thio.

The third family (Family III) comprises substituted oxazolidinones with the following general structure

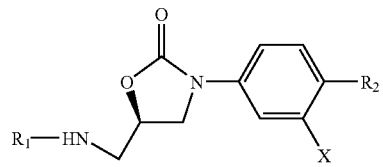

wherein $R_1$ is alkyl, acyl, thio, or aryl, $R_2$ is a C-3, C-4, or C-5 chiral synthon with 1, 2, or 3 chiral centers, and X is F, $NO_2$, Cl, Alkyl, or aryl.

The fourth family (Family IV) comprises substituted oxazolidinones with the general structure

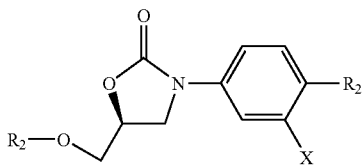

wherein $R_1$ is alkyl, acyl, thio, or aryl, $R_2$ is a C-3, C-4, or C-5 chiral synthon with 1, 2, or 3 chiral centers, and X is F, $NO_2$, Cl, Alkyl, or aryl.

The fifth family (Family V) comprises substituted oxazolidinones with the general structure

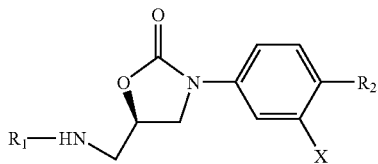

wherein $R_1$ is a C-3, C-4, or C-5 chiral synthon with 1, 2, or 3 chiral centers, $R_2$ is alkyl, aryl, acyl, thio, or heterocycle, and X is F, $NO_2$, Cl, Alkyl, or aryl.

The sixth family (Family VI) comprises substituted oxazolidinones with the general structure

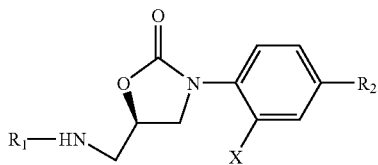

wherein $R_1$ is alkyl, aryl, acyl, thio, or heterocycle, $R_2$ is a C-3, C-4, or C-5 chiral synthon with 1, 2, or 3 chiral centers, and X is F, $NO_2$, Cl, Alkyl, or aryl.

The seventh family (Family VII) comprises substituted oxazolidinones with the general structure

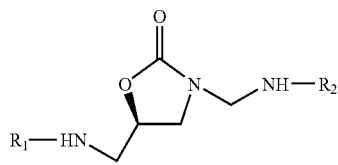

wherein $R_1$ is alkyl, aryl, acyl, thio, or heterocycle and $R_2$ is a C-3, C-4, or C-5 chiral synthon with 1, 2, or 3 chiral centers.

The eighth family (Family VIII) comprises substituted oxazolidinones with the general structure

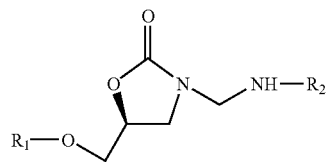

wherein $R_1$ is alkyl, aryl, acyl, thio, or heterocycle and $R_2$ is a C-3, C-4, or C-5 chiral synthon with 1, 2, or 3 chiral centers.

Examples of the C-3, C-4, and C-5 chiral synthons with 1, 2, or 3 chiral centers include, but are not limited to, (R)-3-acetoxy-4-bromobutyric acid, (S)-3-acetoxy-4-bromobutyric acid, (R)-3-Acetoxy-4-bromobutiryl chloride, (S)-3-Acetoxy-4-bromobutiryl chloride, (R)-2-Acetoxy-1,4-dibromobutane, (S)-2-Acetoxy-1,4-dibromobutane, (R)-3-Acetoxy-gamma-butyrolactone, (S)-3-Acetoxy-gamma-butyrolactone, (R)-4-Acetoxy-2-thioxopyrrolidine, (S)-4-Acetoxy-2-thioxopyrrolidine, (R)-4-Acetylthio-2-pyrrolidinone, (S)-4-Acetylthio-2-pyrrolidinone, (R)-4-Amino-1,3-butanediol, (S)-4-Amino-1,3-butanediol, (R)-3-Amino-1,2-dihydroxypropane, hydrochloride, (S)-3-Amino-1,2-dihydroxypropane, hydrochloride, (R)-4-Amino-3-hydroxy-1-trityloxy-butane, (S)-4-Amino-3-hydroxy-1-trityloxy-butane, (R)-4-Amino-3-hydroxybutanoic acid, (S)-4-Amino-3-hydroxybutanoic acid, (S)-4-Aminomethyl-2,2-dimethyl-1,3-dioxolane, (R)-3-Amino-1,2-propanediol, (S)-3-Amino-1,2-propanediol, (S)-N-Benzyl-3,4-dihydroxybutyramide, (R)-1-Benzyl-4-hydroxy-2-pyrrolidinone, (S)-1-Benzyl-4-hydroxy-2-pyrrolidinone, (R)-1-Benzyl-3-mesyloxy pyrrolidine, (S)-1-Benzyl-3-mesyloxy pyrrolidine, (R)-1-Benzyl-3-pyrrolidinol, (S)-1-Benzyl-3-pyrrolidinol, (R)-3-Bromo-1-(bromomethyl)propyl-methoxymethyl, (S)-3-Bromo-1-(bromomethyl)propyl-methoxymethyl ether, (R)-4-Bromo-1,3-butanediol, (S)-4-Bromo-1,3-butanediol, (R)-4-Bromo-1,3-diacetoxy-butane, (S)-4-Bromo-1,3-diacetoxy-butane, (R)-3-Bromo-1,2-dihydroxypropane, (S)-3-Bromo-1,2-dihydroxypropane, (R)-4-Bromo-1,2-epoxybutane, (S)-4-Bromo-1,2-epoxybutane, (R)-5-Bromo-4-(methoxymethoxy)-pentanenitrile, (S)-5-Bromo-4-(methoxymethoxy)-pentanenitrile, (4R)-4-Bromomethyl-2-phenyl-1,3-dioxane, (4S)-4-Bromomethyl-2-phenyl-1,3-dioxane, (R)-1,3-Butanediol, (S)-1,3-Butanediol, (R)-1,2,4-Butanetriol, (S)-1,2,4-Butanetriol, (R)-1,2,4-Butanetriol trimesylate, (S)-1,2,4-Butanetriol trimesylate, (R)-4-Cyano-1,2-epoxybutane, (S)-4-Cyano-1,2-epoxybutane, 1,3-Dehydro-2-deoxy-N-acetylneuraminic acid, (R)-1,4-Dibromo-2-butanol, (S)-1,4-Dibromo-2-butanol, (R)-3,4-Dihydroxybutyramide, (S)-3,4-Dihydroxybutyramide, (R)-2,2-Dimethyl-4-aminomethyl-1,3-dioxane, (S)-2,2-Dimethyl-4-aminomethyl-1,3-dioxane, (R)-2,2-Dimethyl-1,3-dioxolane-4-acetamide, (S)-2,2-Dimethyl-1,3-dioxolane-4-acetamide, (R)-2,2-Dimethyl-1,3-dioxolane-4-acetic acid, methyl ester, (S)-2,2-Dimethyl-1,3-dioxolane-4-acetic acid, methyl ester, (R)-2,2-Dimethyl-1,3-dioxolane-4-acetonitrile, (S)-2,2-Dimethyl-1,3-dioxolane-4-acetonitrile, (R)-2,2-Dimethyl-1,3-dioxolane-4-propanol, (S)-2,2-Dimethyl-1,3-dioxolane-4-propanol, (3R)-1,3-Dioxane-2-methyl-4-carboxylic acid, (3S)-1,3-Dioxane-2-methyl-4-carboxylic acid, (R)-1,4-Ditosyloxy-2-butanol, (S)-1,4-Ditosyloxy-2-butanol, (3R)-3-(1-Ethoxyethoxy)-gamma-butyrolactone, (3S)-3-(1-Ethoxyethoxy)-gamma-butyrolactone, (2R)-2-(1-Ethoxyethoxy)-1,4-butanediol, (2S)-2-(1-Ethoxyethoxy)-1,4-butanediol, Ethyl (R)-4-bromo-3-hydroxybutanoate, Ethyl (S)-4-bromo-3-hydroxybutanoate, Ethyl (R)-4-chloro-3-hydroxybutanoate, Ethyl (S)-4-chloro-3-hydroxybutanoate, (R)-4-cyano-3-hydroxybutanamide, (S)-4-cyano-3-hydroxybutanamide, Ethyl (R)-4-cyano-3-hydroxybutanoate, Ethyl (S)-4-cyano-3-hydroxybutanoate, Ethyl (R)-3,4-epoxybutanoate, Ethyl (S)-3,4-epoxybutanoate, Ethyl (R)-3-hydroxy-decanoate, Ethyl (S)-3-hydroxy-decanoate, Ethyl (R)-3-hydroxy-tetradecanoate, Ethyl (S)-3-hydroxy-tetradecanoate, Ethyl (R)-4-iodo-3-hydroxybutanoate, Ethyl (S)-4-iodo-3-hydroxybutanoate, (R)-4-(4-Fluorophenoxy)methyl butyrolactone, (S)-4-(4-Fluorophenoxy)methyl butyrolactone, (1S,3R)-3-Hydroxy-cyclopentanecarboxylic acid, (1S,3S)-3-Hydroxy-cyclopentanecarboxylic acid, (R)-4-Hydroxy-1- cyclopentene-1-carboxylic acid, (S)-4-Hydroxy-1-cyclopentene-1-carboxylic acid, (R)-4-Hydroxy-2-pyrrolidinone, (S)-4-Hydroxy-2-pyrrolidinone, (4R)-4-(2-Hydroxyethyl)-2-phenyl-1,3-dioxolane, (4S)-4-(2-Hydroxyethyl)-2-phenyl-1,3-dioxolane, (R)-2-Hydroxy-gamma-butyrolactone, (S)-2-Hydroxy-gamma-butyrolactone, (R)-3-Hydroxy-gamma-butyrolactone, (S)-3-Hydroxy-gamma-butyrolactone, (R)-4-Hydroxymethyl butyrolactone, (S)-4-Hydroxymethyl butyrolactone, (R)-4-Hydroxy-2-pyrrolidinethione, (S)-4-Hydroxy-2-pyrrolidinethione, (R)-3-Hydroxytetrahydrofuran, (S)-3-Hydroxytetrahydrofuran, (R)-4-Mercapto-2-pyrrolidinone, (S)-4-Mercapto-2-pyrrolidinone, (R)-2-(Methoxy-1-methylethoxy)-butanediol, (S)-2-(1-Methoxy-1-methylethoxy)-butanediol, Methyl (R)-4,5-dihydroxyisopropylidenepentanoate, Methyl (S)-4,5-dihydroxyisopropylidenepentanoate, Methyl (R)-2-phenyl-1,3-dioxolane-4-acetate, Methyl (S)-2-phenyl-1,3-dioxolane-4-acetate, Methyl (R)-3-hydroxy-4-trityloxy-butanoate, Methyl (S)-3-hydroxy-4-trityloxy-butanoate, (R)-3-Pyrrolidinol, (S)-3-Pyrrolidinol, (R)-3-Chloro-1,2-propanediol, (S)-3-Chloro-1,2-propanediol, (2S)-(+)-glycidal tosylate, Benzyl (R)-glycidyl ether, (R)-3-chlorolactic acid, Ethyl (S)-4-chloro-3-hydroxybutanoate, (S)-3-Hydroxybutyrolactone, (R)-2-hydroxybutyrolactone, (S)-2-Hydroxybutyrolactone, (R)-2-Chlrobutyric acid, (R)-2-bromobutyric acid, (S)-1-iso-propylaminopropanediol, (S)-1-tert-Butylaminopropanediol, (R)-1-cyclohexyl-ethyl-amine, (R)-Ethyl-nipecotate, (S)-Ethyl-nipecotate, (R)-Glycerol-3-phosphate, alpha-Glycerophosphatidylcholine, alpha-glycerophosphatidylethanolamine, (R)-0-Isopropylidene glycerol, (S)-0-Isopropylidene glycerol, (R)-0-Isopropylidene glycerol mesylate, (S)-0-Isopropylidene glycerol mesylate, (R)-0-Isopropylidene glycerol tosylate, (S)-0-Isopropylidene glycerol tosylate, (R)-0-methyl-0-isopropylidene glycerate, (R)-2-tetrahydrofuroic acid, (R)-1-Tosyl-glycerol, and (S)-1-Tosyl-glycerol.

The process for synthesis of the substituted oxazolidinones preferably uses an optically active C-protected oxazolidinone as the starting material, preferably a 5-(protected hydroxymethyl)-oxazolidinone such as 5-trityloxymethyl-oxazolidinone wherein the trityl is triphenylmethyl. Most preferably, the protected oxazolidinone is a 5-(protected hydroxymethyl)-2-oxazolidinone which in a further preferred embodiment is a 5-trityloxymethyl-2-oxazolidinone. The synthesis of 5-trityloxymethyl-2-oxazolidinone and its use are disclosed in U.S. Pat. No. 6,288,239 B1 to Hollingsworth and Wang. The structure of 5-trityloxymethyl-2-oxazolidinone is shown below.

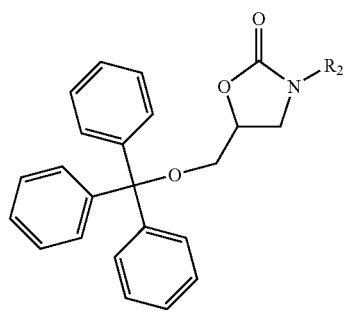

The general process for producing a library of substituted oxazolidinones comprises the following steps. First, a C-(protected oxymethyl)-oxazolidinone is N-arylated with a mixture of compounds comprising a plurality of different aryl acyl, alkyl, aryl, heteroalkyl, heteroaryl, heterocycle, aryl sulfonyl, or phenacyl bromides under Buchwald conditions (Yin and Buchwald, Org. Letts 2: 1101-1104 (2000)) or by simple alkylation under nitrogen. This produces a plurality of N-(substituted)-C-(protected oxymethyl)-oxazolidinones (I).

For example, under simple alkylation conditions, a C-(protected oxymethyl)-oxazolidinone is dissolved in an organic solvent such as tetrahydrofuran (THF) containing a strong base (alkali) which preferably does not have substantial reducing activity or which has reducing activity which is suppressed at low temperatures. Hydrides are strong bases which are suitable for the reaction. Preferably, the strong base is an ionic hydride such as an alkali hydride. Most preferred is sodium hydride which is a powerful base without substantial reducing activity. Other strong bases which may be used include lithium hydride, potassium hydride, rubidium hydride, cesium hydride, sodium alcoholates, sodium amide, and metallic sodium. In general, about 1 equiv. of the strong base (alkali), preferably sodium hydride, is added to the solvent containing the C-(protected oxymethyl)-oxazolidinone. In the case of sodium hydride, which is insoluble in organic solvents, the sodium hydride is provided as a suspension in an organic solvent such as hexane. After allowing the mixture containing the protected oxazolidinone and strong base to incubate at about 0° C. for about 10 minutes with stirring under an inert atmosphere such as nitrogen, the mixture is warmed to room temperature and stirred for about two hours and a mixture of n different arylating reagents, preferably in a molar ratio of about 1 to 1 to 1 to 2 (C-(protected oxymethyl)-oxazolidinone to mixture), is added. The reaction is incubated at room temperature with stirring for a time (about eight hours) sufficient to arylate the N at the 3-position with the n different arylating reagents to produce n N-(substituted)-C-(protected oxymethyl)-oxazolidinones. The reaction is then quenched by adding an aqueous solution containing an acid such as $NH_4Cl$ and the N-(substituted)-C-protected oxymethyl)-oxazolidinones are recovered by extracting the quenched reaction with the organic solvent, drying the extract over a drying agent such as anhydrous $Na_2SO_4$, and concentrating the extract under reduced pressure (in vacuo). The N-(substituted)-C-(protected oxymethyl)-oxazolidinones are preferably purified by chromatography.

Under Buchwald conditions, the C-(protected oxymethyl)-oxazolidinone and about 1 to 2 equiv. of a mixture of n different arylating reagents are incubated with a $Pd(OAc)_2$ catalyst in an organic solvent such as tetrahydrofuran (THF) under an inert atmosphere such as argon at a temperature between about 45° to 110° C. for a time sufficient to arylate the N at the 3-position with the n different arylating reagents to produce n N-(substituted)-C-(protected oxymethyl)-oxazolidinones (in general, about eight hours as determined by gas chromatography). The reaction is then cooled to room temperature, diluted with an organic solvent such as dichloromethane, filtered, and concentrated under reduced pressure (in vacuo). The N-(substituted)-C-(protected oxymethyl)-oxazolidinones are preferably purified by chromatography.

Next, the N-arylated oxazolidinones (N-substituted) are deprotected in the usual fashion by hydrogenolysis using $H_2$ and a palladium catalyst or an acid such as to produce a library of n N-(substituted)-C-hydroxymethyl-oxazolidinones (II). For example, the N-arylated oxazolidinones, preferably purified by chromatography or the like, are incubated in an aqueous solvent such as wet dichloromethane ($CH_2Cl_2$) (about 8:1 $CH_2Cl_2:H_2O$) further containing an acid such as trifluoroacetic acid ($CF_3CO_2H$) at room temperature for a time sufficient (about four hours) to deprotect the C-hydroxymethyl. Preferably, the C-protecting group in the above reaction is a triphenylmethyl group. The reaction is quenched by adding triethylamine or other quenching agent and the deprotected oxazolidinone concentrated under reduced pressure (in vacuo). The concentrated deprotected oxazolidinone is preferably further purified by chromatography.

In a further step, the n N-(substituted)-C-hydroxymethyl-oxazolidinones (II) are O-functionalized with a mixture of n different alkylation, acylation, sulfonylation, halogenation, or other such species. For example, a mixture containing a plurality of different acyl, alkyl, aryl, heteroalkyl, heteroacyl, heteroaryl, heterocycle, phenacyl, aryl sulfonyl, amides thereof, thiols thereof, or other such species, or the O of the hydroxymethyl is replaced by N-aryl, N-sulfonyl, N-sulfide, or other N-species, or the O of the hydroxymethyl is replaced by a thioalkyl, thioaryl, or other thio-species. Methods for converting the hydroxyl group to a nitrogen containing function can be done by any of the methods which are known. These include mesylation or tosylation followed by displacement with ammonia, azide, benzylamine, or other nitrogen nucleophiles as taught for example in U.S. Pat. No. 6,288,239 B1 to Hollingsworth and Wang or U.S. Pat. No. 5,837,870 to Pearlman et al. For example, n substituted oxazolidinones (II), preferably purified by chromatography or the like, are then incubated in an organic solvent such as dry dichloromethane containing about 1 equiv. pyridine and about 1 equiv. of a mixture of n different acyl, alkyl, aryl, heteroalkyl, heteroaryl, heterocycle, phenacyl, aryl sulfonyl, thios and amides thereof, or other such species halides at room temperature for time sufficient (about 12 to 16 hours) to functionalize the C-hydroxymethyl at the 4- or 5-position. Afterwards, the reaction is quenched by addition of ammonium chloride, extracting the organic layer with dichloromethane, drying the organic layer extract over a drying agent such as anhydrous $Na_2SO_4$, and concentrating under reduced pressure (in vacuo). The above process generates a library of $n^2$ N-(substituted)-C-(substituted methyl)-oxazolidinones (III). For example, if ten different aryl bromides reagents are used in the first step and ten different halide reagents in the second step, 100 N-(substituted)-C-(substituted)-oxazolidinones (III) are obtained.

Each of the products (I, II, or III) produced above can be separated chromatographically and each separately evaluated as drug or antimicrobial candidates.

The process takes advantage of the ease of reaction of the nitrogen atom at the 3-position in C-(protected oxymethyl)-oxazolidinones which enables both arylation and alkylation sequences for substituting the N to be used. A further advantage is that in one or two steps, the protecting group can be removed and the hydroxyl group functionalized. In the same scheme, the oxygen substituent at the C-position methyl can be replaced with halo, thio, phenoxy, azido, or substituted nitrogen groups under standard Mitsunobu conditions (Mitsunobu, Synthesis 1 (1981)). Alternatively, the hydroxyl group can be first converted to a sulfonate, halo, or other such activating group.

Thus, the process involves essentially two steps, the first step is generating a first library of n N-(substituted)-C-hydroxymethyl-oxazolidinones from a C-protected oxazolidinone and the second step is O-functionalizing acylating the C-hydroxymethyl to generate a library of $n^2$ N-(substituted)-C-(substituted methyl)-oxazolidinones.

In a preferred embodiment, the first library comprises at least 10 different N-(substituted)-C-hydroxymethyl-oxazolidinones prepared by reacting C-(protected oxymethyl)-oxazolidinones with at least 10 different N-arylating reagents and the second library comprises at least 100 different N-(substituted)-C-(substituted)-oxazolidinones prepared by reacting the ten N-(substituted)-C-hydroxymethyl-oxazolidinones with at least ten different O-functionalizing acylating reagents. In other embodiments of the library, the substituted oxazolidinones comprise a plurality of molecules with N-position substitutions and a single substitution group at the C-position of the molecules or a plurality of molecules with C-position substitutions and a single substitution group at the N-position of the molecules. A further embodiment of the library can comprise substituted oxazolidinones with either N-position substitutions only (N-(substituted)-C-(methyl)-oxazolidinones) or C-position substitutions only (C-(substituted methyl)-oxazolidinones. The particular library embodiment chosen depends on the particular objectives of the drug or antimicrobial screening program.

In a preferred embodiment, the oxazolidinone is 2-oxazolidinone. In a further preferred embodiment as shown in Scheme 3 below, the C-(protected hydroxymethyl)-2-oxazolidinone is C-trityloxymethyl-2-oxazolidinone. The C-trityloxymethyl-2-oxazolidinone is N-arylated (N at position 3) with a mixture of n different aryl acyl, alkyl, aryl, heteroalkyl, heteroaryl, heterocycle, aryl sulfonyl, or phenacyl bromides, or other such bromides under Buchwald conditions (Yin and Buchwald, Org. Letts. 2: 1101-1104 (2000)) or simple alkylation under nitrogen to produce N-(substituted)-C-trityloxymethyl-2-oxazolidinones. The trityl (Tr) group is then removed by hydrogenation to produce a library of n N-(substituted)-C-hydroxymethyl-2-oxazolidinones.

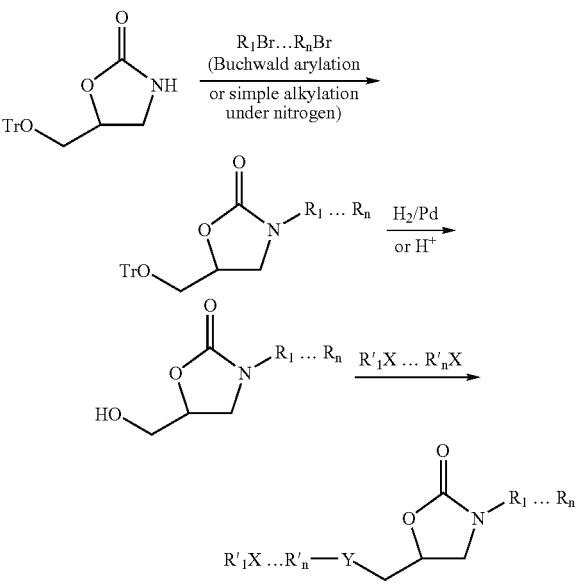

Scheme 3

In a further step, the N-(substituted)-C-hydroxymethyl-2-oxazolidinones are O-functionalized acylated with a mixture of n different acyl, alkyl, aryl, heteroalkyl, heteroaryl, heterocycle, phenacyl, aryl sulfonyl, amides thereof, or other such species halides, or the O of the hydroxymethyl is replaced by N-aryl, N-sulfonyl, N-sulfide, or other N-species, or the O is replaced by a thioalkyl, thioaryl, or other thio-species. This generates a library of $n^2$ N-(substituted)-C-(substituted methyl)-2-oxazolidinones. For example, if ten aryl bromides reagents are used in the first step and ten halide species reagents in the second step, a total of 100 N-(substituted)-C-(substituted methyl)-2-oxazolidinones are made. In one embodiment, the starting oxazolidinone is 4-(protected oxymethyl)-2-oxazolidinone, preferably 4-trityloxymethyl-oxazolidinone, and the n library comprises 3-(substituted)-4-hydroxymethyl-2-oxazolidinone and the $n^2$ library comprises 3-(substituted)-4-(substituted methyl)-2-oxazolidinone. In a preferred embodiment, the starting oxazolidinone is 5-(protected oxymethyl)-2-oxazolidinone, preferably 5-trityloxymethyl-oxazolidinone, and the n library comprises 3-(substituted)-5-hydroxymethyl-2-oxazolidinone and the $n^2$ library comprises 3-(substituted)-5-(substituted methyl)-2-oxazolidinone.

The novel process allows for the rapid synthesis of a plurality of substituted oxazolidinones including but not limited to 3-(substituted)-5-(substituted methyl)-oxazolidinones, 3-(substituted)-4-(substituted methyl)-oxazolidinones, 3-(substituted)-5-(substituted methyl)-2-oxazolidinones, 3-(substituted)-4-(substituted methyl)-2-oxazolidinones, 3-(substituted)-5-hydroxymethyl-oxazolidinones, 3-(substituted)-4-hydroxymethyl-oxazolidinones, 3-(substituted)-5-hydroxymethyl-2-oxazolidinones, and 3-(substituted)-4-hydroxymethyl-2-oxazolidinones. The number of substituted oxazolidinones synthesized by the novel process depends on the number of substituting reagents included in the process. Therefore, the use of substituting reagents such as sulfur, nitrogen, and oxygen nucleophiles on the primary hydroxyl group and the amine group of the oxazolidinones affords access to a plurality of families of optically active compounds in a single process which is fast and simple.

The substituted oxazolidinones produced by the above process can be separated using standard chromatography methods and the separated substituted oxazolidinones screened for biological activity including antimicrobial activity or for usefulness as a drug or an intermediate for synthesizing a drug. Technologies and methods for screening compounds in combinatorial libraries are well known in the art.

For any particular substituted oxazolidinone which has useful characteristics, biological activities, or which is a useful intermediate for the synthesis of other compounds, the above process for making the combinatorial library is modified to a process for making the particular substituted oxazolidinone. The modified process differs from the process for preparing the library in that the plurality of reagents shown in Scheme 3 and described above is replaced with the particular reagents which will result in the synthesis of the particular substituted oxazolidinone. Thus, the general method involves the following steps: (1) substituting the N-group of optically active C-protected oxazolidinone, preferably trityloxy-2-oxazolidione, by simple alkylation under nitrogen or N-arylating under Buchwald conditions to produce an N-substituted oxazolidinone, (2) removing the C-protecting group, and (3) substituting the hydrogen of the C-4 or C-5 hydroxymethyl with an alkylation, acylation, arylation, sulfonylation, or other such species halide, or substituting the hydroxy group with a thioalkyl, thioaryl, or other thio-group species to replace the O of the hydroxymethyl with S, or substituting the hydroxy group under conditions with an N-acyl, N-sulfonyl, N-sulfide, or other N-group species to replace the O of the hydroxymethyl with N. The above process enables particular substituted oxazolidinones of any one of the eight families (Families I to VIII) to be prepared.

When libraries comprising substituted oxazolidinones prepared according to the process of the present invention were tested for antimicrobial activity, many of the substituted oxazolidinones in the libraries with the genus structure were discovered to have antimicrobial activity against gram positive and Gram negative bacteria. In particular, many of the substituted oxazolidinones were found to be active against Gram positive bacteria such as those of the genera *Staphlococcus* and *Enterococcus* and Gram negative bacteria such as those of the genera *Escherichia* with 90 to 100% Minimum Inhibitory Concentrations ($MIC_{90-100}$) of less than 10 µg/mL. The discovery that many of the novel substituted oxazolidinones had antibacterial activity was surprising since the novel substituted oxazolidinones do not contain all three elements considered necessary for antibacterial activity. Thus, the novel substituted oxazolidinones represent an new class of antimicrobial agents which are active against a variety of bacteria, in particular, Gram positive bacteria such as *Staphylococcus aureus, Pseudomonas aeriginose*, pneumococci (*Streptococcus pneumoniae*), enterococci (*Enterococcus faecium, Enterococcus faecalis, Enterococcus gallinarum*), Groups A, B, C, and G streptococci, *Streptococcus oralis*, and *Streptococcus sanguis* and Gram negative bacteria such as *Escherichia coli*.

Preferably, the substituted oxazolidinones with antimicrobial activity are embraced by the species of Families I to VIII. Tables 2 and 3 show examples of substituted oxazolidinones produced as disclosed herein which have been shown to have antimicrobial activity. Tables 1 and 2 show the results of analyses of the antimicrobial activity for several of the substituted oxazolidinones. The substituted oxazolidinones which are particularly useful antimicrobials have an $MIC_{90-100}$ against at least one gram positive bacteria of about 300 µg/mL or less, preferably, of about 100 µg/mL or less, most preferably, of about 10 µg/mL or less. Because particular strains of these bacteria species have developed antibiotic resistance, the novel substituted oxazolidinones are particularly useful for use against the antibiotic resistant strains of bacteria such as those shown in Table 1.

To inhibit or prevent a bacterial infection from developing in a human or animal or to treat a bacterial infection in a human or animal patient, compositions comprising a carrier and one or more of the novel substituted oxazolidinones disclosed herein can be administered to the human or animal intravenously; by injection; orally by tablet, capsule, or liquid suspension; or topically.

For intravenous administration, one or more of the novel substituted oxazolidinones is dissolved in dimethyl sulfoxide or other pharmaceutically acceptable organic solvent, which is then diluted to about 5% (v/v) in a carrier which is a sterile isotonic solution. A suitable isotonic solution includes sodium citrate, citric acid, and dextrose wherein the $Na^+$ content is about 0.38 mg/mL (1.7 mEq/100 mL). Linezolid in the above isotonic solution has been approved for human use by the U.S. Food and Drug Administration. The intravenous solution can be applied as 15- to 20-minute infusions or by continuous infusion over an extended time period through a catheter surgically implanted through the patient's vein. In particular embodiments, the one or more novel substituted oxazolidinones is combined with one or more antibiotics or other antibacterial agents.

For injection, one or one or more of the novel substituted oxazolidinones is dissolved in dimethyl sulfoxide or other pharmaceutically acceptable organic solvent, which is then diluted to about 5% (v/v) in a carrier which is a sterile isotonic solution or sterile distilled water. The solution can be administered subcutaneously, intramuscularly, or peritoneally. In particular embodiments, one or more the substituted oxazolidinones is combined with one or more antibiotics or other antibacterial agents.

For oral administration, one or more of the novel substituted oxazolidinones is mixed with a pharmaceutically acceptable carrier and the mixture compressed into a tablet, which can be film coated, or encapsulated within a pharmaceutically acceptable capsule. For example, one or more of the novel oxazolidinones are admixed with a carrier which includes as the inactive ingredients: corn starch, microcrystalline cellulose, hydroxy propylcellulose, sodium starch glycolate, magnesium stearate, hydroxypropyl methylcellulose, polyethylene glycol, titanium dioxide, and carnauba wax. The admixture is formed into tablets or encapsulated in capsules. Each tablet or capsule contains about 0.1 mEq $Na^+$. Linezolid in a carrier which includes the above inactive ingredients has been approved for human use by the U.S. Food and Drug Administration. In particular embodiments, one or more of the substituted oxazolidinones is combined with one or more antibiotics or other antibacterial agents.

Alternatively, the novel substituted oxazolidinones are administered orally as a suspension. In this embodiment, one or more of the novel substituted oxazolidinones is provided in a pharmaceutically acceptable flavored granule or powder carrier for constitution into a suspension for oral administration. For example, one or more of the novel substituted oxazolidinones are admixed with a granule or powder which includes as the inactive ingredients: sucrose, citric acid, sodium citrate, microcrystalline cellulose, carboxy methyl cellulose sodium, aspartame, xanthan gum, mannitol, sodium benzoate, colloidal silicon dioxide, sodium chloride, and flavors. Linezolid in a granule or powder containing the above inactive ingredients has been approved for human use by the U.S. Food and Drug Administration. In particular embodiments, one or more of the substituted oxazolidinones is combined with one or more antibiotics or other antibacterial agents.

For topical administration, one or more of the substituted oxazolidinones can be provided in an ointment, a lotion, a cream, or a gel. In particular embodiments, one or more of the substituted oxazolidinones is combined with one or more steroids, one or more antibiotics or other antibacterial agents, or both.

The following examples are intended to promote a further understanding of the present invention.

EXAMPLE 1

This example illustrates the preparation of (S)-5-trityloxymethyl-2-oxazolidinone using the process disclosed in U.S. Pat. No. 6,288,239 B1 to Hollingsworth and Wang.

In a flask, (S)-3,4-dihydroxybutyramide (11.9 g, 0.10 moles) was dissolved in 50 mL of tetrahydrofuran (THF) to which 50 mL of dimethylformamide and 10 mL pyridine was added followed by 30.6 g (0.11 moles) of trityl chloride. A drying tube filled with calcium chloride was used to exclude moisture. The reaction mixture was stirred for 36 hours at room temperature. Afterwards, the reaction mixture was filtered to remove the solids. The liquid was concentrated under reduced pressure to remove most of the solvent. The concentrate was poured into ice water, stirred for about half an hour, and then the water layer was removed from the organic layer containing the 3-Hydroxy-4-trityloxy butyramide. The product was a semi-crystalline liquid which was dried in vacuo. Afterwards, the excess trityl chloride was washed away by tituration with hexane.

The 3-hydroxy-4-trityloxy butyramide (3.61 g, 0.01 moles) was dissolved in 30 mL THF. Fifteen mL of a 13% sodium hypochlorite solution was added and the mixture was stirred vigorously. Next, 1.6 g of sodium hydroxide dissolved in 10 mL of water was added. The reaction was stirred at 55-60° C. for eight hours after which time the conversion to 5-trityloxymethyl-2-oxazolidinone was completed as indicated by TLC and $^1$H-NMR spectroscopy. The organic layer was separated from the aqueous layer and saved. The aqueous layer was extracted three times with THF. The saved organic layer and the THF extracts were combined and then concentrated to remove the solvent. The residue was taken up in dichloromethane and the solution dried over sodium sulfate. Afterwards, the solution was concentrated to remove the solvent and the oxazolidinone was obtained as a white crystalline product (3.4 g, yield 95%). Normally, this crude product did not need further purification.

EXAMPLE 2

This comparative example illustrates the N-arylation of 5-trityloxymethyl-2-oxazolidinone to produce (S)-3-(2-nitro)phenyl-5-trityloxymethy)-2-oxazolidinone using the procedure disclosed in Shakespeare, Tetrahedron Lett. 40: 2035-2038 (1999).

To 36 mg of 5-trityloxymethyl-2-oxazolidinone, 30 mg (1.5 equivs) 1-bromo-2-nitrobenzene, 2.4 mg (0.1 equivs) palladium (II) acetate, 5.5 mg (0.1 equivs) 1,1'-bis(diphenylphosphino)-ferrocene, 16 mg (0.15 equivs) potassium t-butoxide, and 1 mL toluene were added under a nitrogen atmosphere. The mixture was heated at 110° C. for 14 hours after which time the mixture was resolved by thin-layer chromatography (TLC) comprising silica with dichloromethane as the eluant.

The TLC indicated complete conversion to a single product: (S)-3-(2-nitro)phenyl-5-trityloxymethyl-2-oxazolidinone. The mixture was cooled and diluted with dichloromethane. The dark brown organic solution was washed with 5% sodium carbonate, concentrated, and chromatographed on silica gel using dichloromethane as the eluant. The product (47 mg, 98%) was obtained as a pale yellow solid which crystallized from chloroform:methanol as off-white crystals with a melting point of 236-237° C. The product was analyzed by $^1$H-NMR, $^{13}$C NMR, IR, MS, and HRMS.

$^1$H-NMR (300 MHz, CDCl$_3$) δ 8.03 (dd, 1H, J=8.0, 2.1 Hz), 7.65 (td, 1H, J=8.0, 2.1 Hz), 7.46-7.53 (m, 6H), 7.44 (td, 1H, J=8.0, 2.1 Hz), 7.20-7.36 (m, 10H), 4.83 (m, 1H), 4.07 (t, 1H, J=8.5 Hz), 3.89 (t, 1H, J=8 Hz), 3.58 (dd, 1H, J=11.8, 4.5 Hz), 3.36 (dd, 1H, J=11.8, 4.5 Hz). $^{13}$C NMR (75 MHz, CDCl$_3$) δ 176.4, 143.5, 134.1, 131.7, 127.6, 87.5, 73.4, 64.0, 49.4. IR cm$^{-1}$ 3057, 2924, 1760, 1607, 1532, 1489, 1449, 1411, 1355. MS (electron impact) m/z 57, 71, 91, 105, 131, 165, 243, 259, 403, 463, 480 (M$^+$). HRMS (electron impact) analyzed for $C_{29}H_{24}N_2O_5$: theoretical MW 480.1685, observed MW 480.1683.

EXAMPLE 3

This example illustrates the preparation of a library of substituted 2-oxazolidinones, which are members of Family II, according to the process of the present invention. In this example, (S)-5-trityloxymethyl-2-oxazolidinone is N-acylated with 2,5-dimethoxyphenacyl bromide, detritylated, and then acylated with ten different acyl halides or anhydrides to produce a library of n=10 3-(2,5-dimethoxyphenacyl)-5-(substituted methyl)-2-oxazolidinones.

In the first step (FIG. 1A), (S)-3-(2,5-dimethocyphenacyl)-5-trityloxymethyl-2-oxazolidinone was produced in a reaction comprising (S)-5-trityloxymethyl-2-oxazolidinone and the aryl bromide: 2,5-dimethoxyphenacyl bromide. To a solution of 3.59 g (10 mmoles) of(S)-5-trityloxymethyl-2-oxazolidinone (MW 359.2) in 40 mL THF at 4° C., 400 mg (10 mmoles) NaH (MW 24) as a 60% suspension in hexane was added. The reaction mixture was stirred for about 10 minutes under nitrogen at 0° C. and then warmed up to room temperature and stirred for an additional two hours. Then, 2.59 g (10 mmoles) of 2-bromo-4'dimethoxyacetophenone (MW 259.1) was added and the reaction mixture stirred at room temperature for about eight hours. Afterwards, the reaction was quenched by adding 20 mL 20% NH$_4$Cl. The organic layer was removed and saved. The aqueous layer was extracted two times with 40 mL aliquots of THF. The THF extracts were combined with the saved organic layer and the mixture dried with 2.5 g anhydrous Na$_2$SO$_4$. The mixture was then concentrated in vacuo to provide a crude product. The crude product was purified by flash column chromatography using 40% EtOAc:Hexane followed by 60% EtOAc:Hexane. This produced 2.73 g (51% yield) of the (S)-3-(2,5-dimethocyphenacyl)-5-trityloxymethyl-2-oxazolidinone (product) (MW 537.6). The product was compared to the starting material by TLC using 40% EtOAC/Hexane as the solvent. The Rf of the starting material was 0.2 and the Rf of the product was 0.4.

Figure 1B:
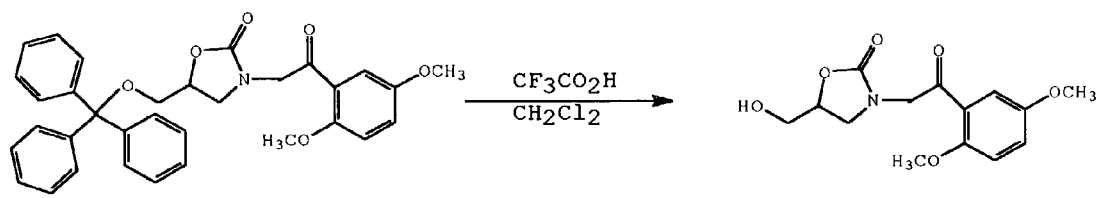
FIG. 1B shows the conversion of 3-(2,5-dimethoxyphenacyl)-5-trityloxymethyl-2-oxazolidinone to 3-(2,5-dimethoxyphenacyl)-5-hydroxymethyl-2-oxazolidinone.

In the second step (FIG. 1B), the trityl group was removed from the (S)-3-(2,5-dimethocyphenacyl)-5-trityloxymethyl-2-oxazolidinone. To 1.07 g (2.0 mmoles) of (S)-3-(2,5-dimethocyphenacyl)-5-trityloxymethyl-2-oxazolidinone in wet CH$_2$Cl$_2$ (8 mL CH$_2$Cl$_2$, 1 mL H$_2$O), 0.14 mL CF$_3$CO$_2$H (210 mg, 1.8 mmoles) (MW 114.02) was added and the reaction mixture stirred for about four hours. Afterwards, the reaction was quenched by adding 0.2 mL triethylamine and the reaction mixture concentrated in vacuo. The residue was purified by flash chromatography to produce 472 mg (80% yield) of (S)-3-(2,5-dimethocyphenacyl)-5-hydroxymethyl-2-oxazolidinone (product) (MW 295.29). The product was compared to the starting material by TLC using 80% EtOAC:Hexane as the solvent. The Rf of the starting material was 0.7 and the Rf of the product was 0.1.

Figure 1C:
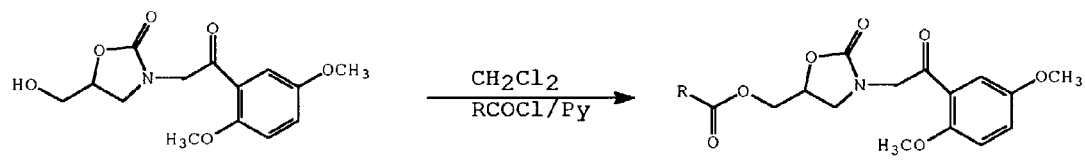
FIG. 1C shows the conversion of 3-(2,5-dimethoxyphenacyl)-5-hydroxymethyl-2-oxazolidinone to a library of ten 3-(2,5-dimethoxyphenacyl)-5-(substituted methyl)-2-oxazolidinones.
Figure 2:
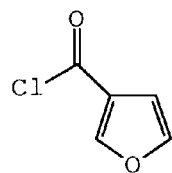
FIG. 2 shows the ten chlorides used in the O-functionalization.
Figure 2:
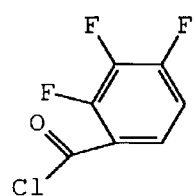
Figure 2:
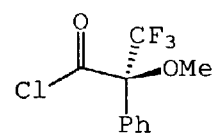
Figure 2:
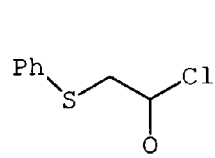
Figure 2:
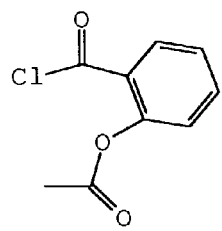
Figure 2:
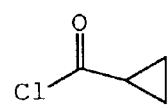
Figure 2:
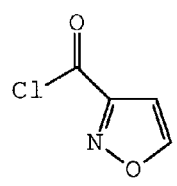
Figure 2:
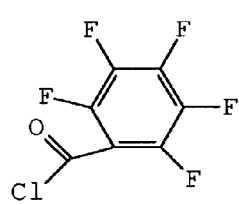
Figure 2:
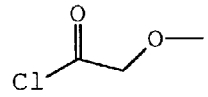
Figure 2:
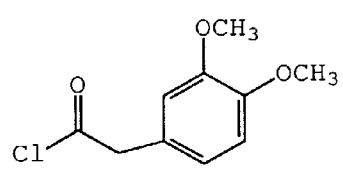

In the third step (FIG. 1C), the library of ten substituted 2-oxazolidinones was produced in a reaction comprising the (S)-3-(2,5-dimethocyphenacyl)-5-hydroxymethyl-2-oxazolidinone and the ten different acetyl chlorides shown in FIG. 2. To about 295 mg (1.0 mmoles) of (S)-3-(2,5-dimethocyphenacyl)-5-hydroxymethyl-2-oxazolidinone in dry CH$_2$Cl$_2$ (8 mL CH$_2$Cl$_2$), 1.0 equiv. (1.1 mmoles) of pyridine was added and the reaction mixture stirred at room temperature. To this reaction mixture was added 1.0 equiv. of a mixture of ten different acetyl chlorides. The reaction was stirred overnight at room temperature. Afterwards, TLC of an aliquot indicated that complete conversion of the (S)-3-(2,5-dimethocyphenacyl)-5-hydroxymethyl-2-oxazolidinone to (S)-3-(2,5-dimethocyphenacyl)-5-(substituted methyl)-2-oxazolidinone had occurred. Therefore, about 3 mL of 20% NH$_4$Cl was added to the reaction mixture and the organic layer removed and saved. The aqueous layer was extracted two times with 40 mL aliquots of CH$_2$Cl$_2$. The CH$_2$Cl$_2$ extracts were combined with the saved organic layer and the mixture dried with 2.5 g anhydrous Na$_2$SO$_4$. The mixture was then concentrated in vacuo to provide a crude product. The crude product was analyzed by $^1$H-NMR, $^{13}$C NMR, HPLC, and TLC using a EtOAc:hexane (2:1) solvent system.

Figure 3:
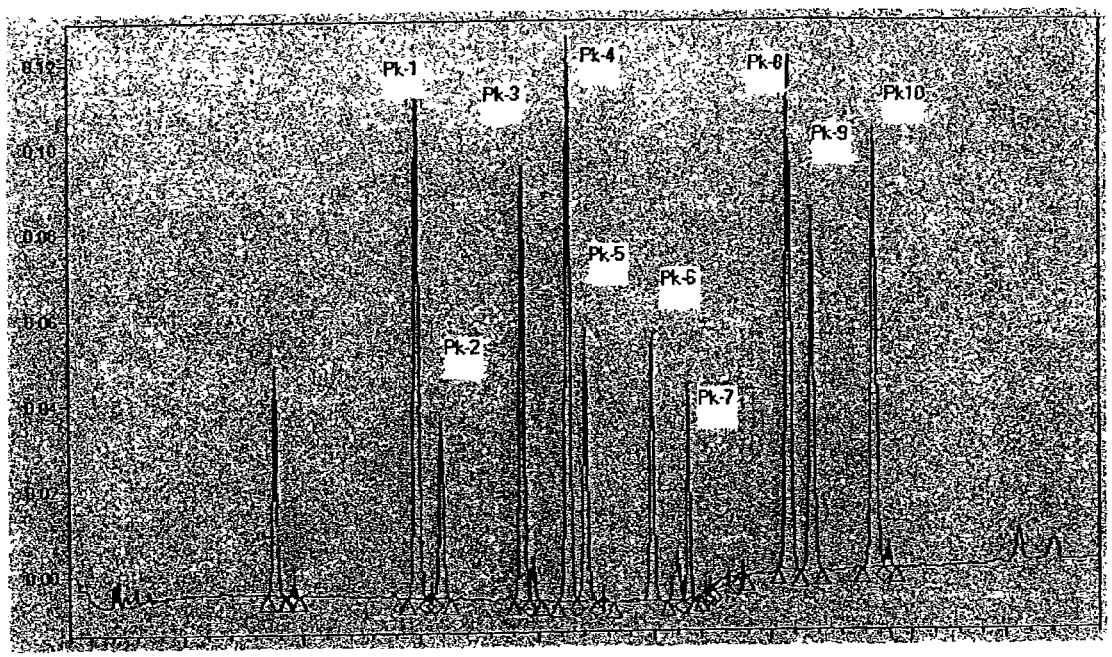
FIG. 3 shows an HPLC profile of the library of ten 3-(2,5-dimethoxyphenacyl)-5-(substituted methyl)-2-oxazolidinones prepared as shown in FIGS. 1A to 1C.
Figure 4:
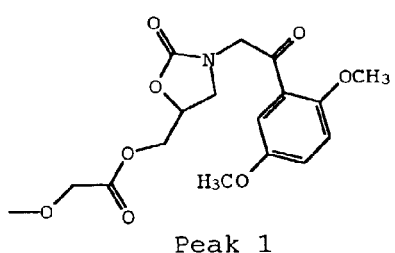
FIG. 4 shows the structure of the ten 3-(2,5-dimethoxyphenacyl)-5-(substituted methyl)-2-oxazolidinones identified in FIG. 3.
Figure 4:
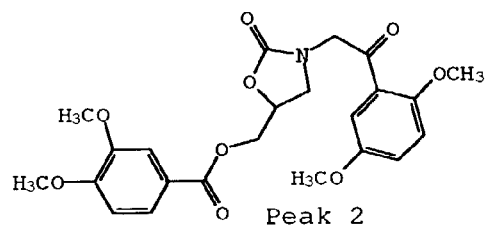
Figure 4:
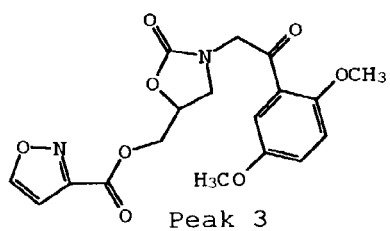
Figure 4:
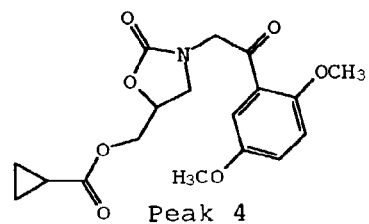
Figure 4:
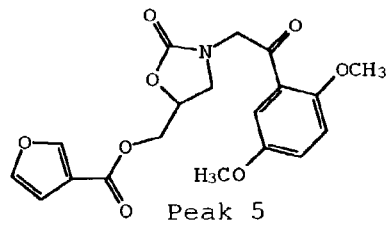
Figure 4:
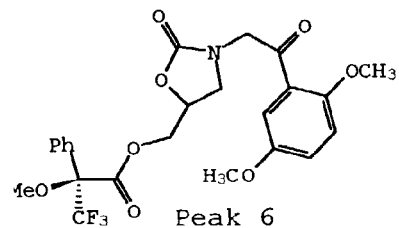
Figure 4:
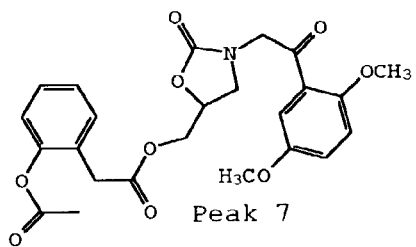
Figure 4:
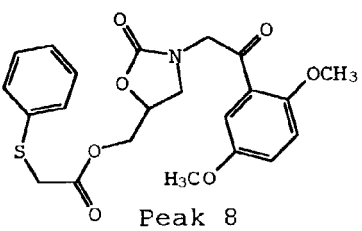
Figure 4:
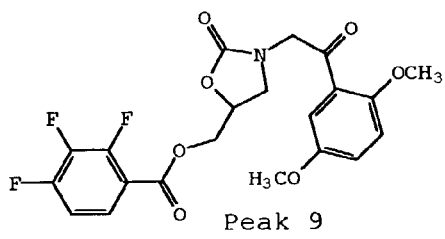
Figure 4:
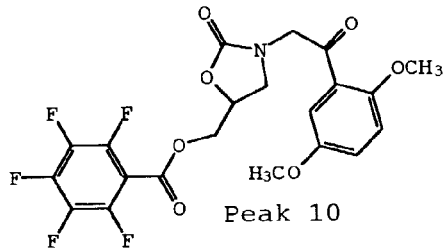

An HPLC profile of the (S)-3-(2,5-dimethocyphenacyl)-5-(substituted methyl)-2-oxazolidinone products made is shown in FIG. 3. The products represented by the peaks in the HPLC are shown in FIG. 4. This example illustrates the principle of the present invention. As shown by this example, providing n=10 acetyl halides in a single reaction produces 10 (S)-3-(2,5-dimethocyphenacyl)-5-(substituted methyl)-2-oxazolidinone products. If n=10 aryl bromides had been used as well to arylate the N at the 3-position, the process would have generated 100 (S)-3-(substituted)-5-(substituted methyl)-2-oxazolidinone products.

EXAMPLE 4

The substituted oxazolidinone (S)-3-(3,3-dimethyl-2-butone)-5-(4-nitro-benzenesulfonyloxymethyl)-2-oxazolidinone

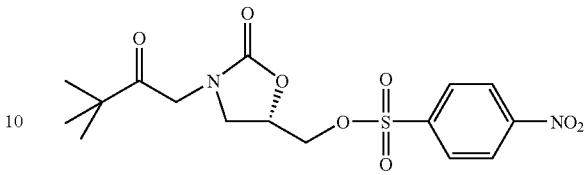

is prepared as follows.

In the first step, (S)-3-(3,3-dimethyl-2-butone)-5-trityloxymethyl-2-oxazolidinone is produced in a reaction comprising (S)-5-trityloxymethyl-2-oxazolidinone and BrCH$_2$COC(CH$_3$)$_3$. To a solution of about 10 mmoles of (S)-5-trityloxymethyl-2-oxazolidinone in 40 mL tetrahydrofuran (THF) at 4° C., 10 mmoles NaH as a 60% suspension in hexane is added. The reaction mixture is stirred for about 10 minutes under nitrogen at 0° C. and then warmed up to room temperature and stirred for an additional two hours. Then, about 10 mmoles of BrCH$_2$COC(CH$_3$)$_3$ is added and the reaction mixture stirred at room temperature for about eight hours. Afterwards, the reaction is quenched by adding 20 mL 20% NH$_4$Cl. The organic layer is removed and saved. The aqueous layer is extracted two times with 40 mL aliquots of THF. The THF extracts are combined with the saved organic layer and the mixture dried with 2.5 g anhydrous Na$_2$SO$_4$. The mixture is then concentrated in vacuo to provide (S)-3-(3,3-dimethyl-2-butone)-5-trityloxymethyl-2-oxazolidinone as a crude product. The crude product is purified by flash column chromatography using 40% EtOAc:Hexane followed by 60% EtOAc:Hexane. The product is compared to the starting material by TLC using 40% EtOAC/Hexane as the solvent.

In the second step, the trityl group is removed from the (S)-3-(3,3-dimethyl-2-butone)-5-trityloxymethyl-2-oxazolidinone. To about 2.0 mmoles of the crude product in wet CH$_2$Cl$_2$ (8 mL CH$_2$Cl$_2$, 1 mL H$_2$O), 0.14 mL CF$_3$CO$_2$H (1.8 mmoles) is added and the reaction mixture stirred for about four hours. Afterwards, the reaction is quenched by adding 0.2 mL triethylamine and the reaction mixture concentrated in vacuo. The residue is purified by flash chromatography to produce (S)-3-(3,3-dimethyl-2-butanone)-5-hydroxymethyl-2-oxazolidinone. The product can be compared to the starting material by TLC using 80% EtOAC:Hexane as the solvent to determine the yield.

In the third step, the (S)-3-(3,3-dimethyl-2-butone)-5-(4-nitro-benzenesulfonyloxymethyl)-2-oxazolidinone is produced in a reaction comprising the (S)-3-(3,3-dimethyl-2-butanone)-5-hydroxymethyl-2-oxazolidinone and nitrobenzenesulfonyl chloride. To about 1.0 mmoles of the ((S)-3-(3,3-dimethyl-2-butanone)-5-hydroxymethyl-2-oxazolidinone in dry CH$_2$Cl$_2$ (8 mL CH$_2$Cl$_2$), 1.0 equiv. (1.1 mmoles) of pyridine is added and the reaction mixture stirred at room temperature. To this reaction mixture is added 1.0 equiv. of compound nitrobenzenesulfonyl chloride. The reaction is stirred overnight at room temperature. Afterwards, an aliquot of the reaction is analyzed by TLC to determine whether complete conversion of the (S)-3-(3,3-dimethyl-2-butanone)-5-hydroxymethyl-2-oxazolidinone to the substituted oxazolidinone has occurred. Thereafter, about 3 mL of 20% NH$_4$Cl is added to the reaction mixture and the organic layer is removed and saved. The aqueous layer is extracted two times with 40 mL aliquots of CH$_2$Cl$_2$. The CH$_2$Cl$_2$ extracts are combined with the saved organic layer and the mixture is dried with 2.5 g anhydrous Na$_2$SO$_4$. The mixture is then concentrated in vacuo to provide a crude product of the substituted oxazolidinone. The crude product is analyzed by $^1$H-NMR, $^{13}$C NMR, HPLC, and TLC using a EtOAc:hexane (2:1) solvent system and is further purified by standard chromatography methods.

EXAMPLE 5

The substituted oxazolidinone (S)-3-(3,3-dimethyl-2-butone)-5-(4-isocyanobenzenesulfonyloxymethyl)-2-oxazolidinone

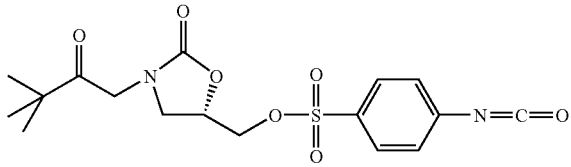

is prepared as follows.

(S)-3-(3,3-dimethyl-2-butone)-5-hydroxymethyl-2-oxazolidinone is prepared as in Example 4. Then the (S)-3-(3,3-dimethyl-2-butone)-5-(4-isocyanobenzenesulfonyloxymethyl)-2-oxazolidinone is produced in a reaction comprising the (S)-3-(3,3-dimethyl-2-butanone)-5-hydroxymethyl-2-oxazolidinone and isocyanobenzenesulfonyl chloride as follows.

To about 1.0 mmoles of the ((S)-3-(3,3-dimethyl-2-butanone)-5-hydroxymethyl-2-oxazolidinone in dry CH$_2$Cl$_2$ (8 mL CH$_2$Cl$_2$), 1.0 equiv. (1.1 mmoles) of pyridine is added and the reaction mixture stirred at room temperature. To this reaction mixture is added 1.0 equiv. of isocyanobenzenesulfonyl chloride. The reaction is stirred overnight at room temperature. Afterwards, an aliquot of the reaction is analyzed by TLC to determine whether complete conversion of the (S)-3-(3,3-dimethyl-2-butanone)-5-hydroxymethyl-2-oxazolidinone to the substituted oxazolidinone has occurred. Thereafter, about 3 mL of 20% NH$_4$Cl is added to the reaction mixture and the organic layer is removed and saved. The aqueous layer is extracted two times with 40 mL aliquots of CH$_2$Cl$_2$. The CH$_2$Cl$_2$ extracts are combined with the saved organic layer and the mixture is dried with 2.5 g anhydrous Na$_2$SO$_4$. The mixture is then concentrated in vacuo to provide a crude product of the substituted oxazolidinone. The crude product is analyzed by $^1$H-NMR, $^{13}$C NMR, HPLC, and TLC using a EtOAc:hexane (2:1) solvent system and is further purified by standard chromatography methods.

EXAMPLE 6

The substituted oxazolidinone (S)-3-(3,3-dimethyl-2-butone)-5-(7-chloro-2,1,3-benzoxadiazole-4-sulfonyloxymethyl)-2-oxazolidinone (34)

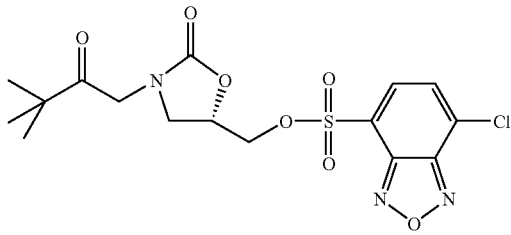

is prepared as follows.

(S)-3-(3,3-dimethyl-2-butone)-5-hydroxymethyl-2-oxazolidinone is prepared as in Example 4. The substituted oxazolidinone 34 is then produced in a reaction comprising the (S)-3-(3,3-dimethyl-2-butanone)-5-hydroxymethyl-2-oxazolidinone and 7-chloro-2,1,3-benzoxadiazole-4-sulfonyl chloride as follows.

To about 1.0 mmoles of the ((S)-3-(3,3-dimethyl-2-butanone)-5-hydroxymethyl-2-oxazolidinone in dry CH$_2$Cl$_2$ (8 mL CH$_2$Cl$_2$), 1.0 equiv. (1.1 mmoles) of pyridine is added and the reaction mixture stirred at room temperature. To this reaction mixture is added 1.0 equiv. of compound 7-chloro-2,1,3-benzoxadiazole-4-sulfonyl chloride. The reaction is stirred overnight at room temperature. Afterwards, an aliquot of the reaction is analyzed by TLC to determine whether complete conversion of the (S)-3-(3,3-dimethyl-2-butanone)-5-hydroxymethyl-2-oxazolidinone to the substituted oxazolidinone 34 has occurred. Thereafter, about 3 mL of 20% NH$_4$Cl is added to the reaction mixture and the organic layer is removed and saved. The aqueous layer is extracted two times with 40 mL aliquots of CH$_2$Cl$_2$. The CH$_2$Cl$_2$ extracts are combined with the saved organic layer and the mixture is dried with 2.5 g anhydrous Na$_2$SO$_4$. The mixture is then concentrated in vacuo to provide a crude product of the substituted oxazolidinone 34. The crude product is analyzed by $^1$H-NMR, $^{13}$C NMR, HPLC, and TLC using a EtOAc:hexane (2:1) solvent system and is further purified by standard chromatography methods.

EXAMPLE 7

The substituted oxazolidinone (S)-3-(3-butene-2-one)-5-(7-chloro-2,1,3-benzoxadiazole-4-sulfonyloxymethyl)-2-oxazolidinone

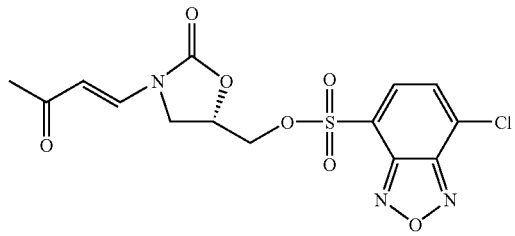

is prepared as follows.

In the first step, (S)-3-(3-butene-2-one)-5-trityloxymethyl-2-oxazolidinone is produced in a reaction comprising (S)-5-trityloxymethyl-2-oxazolidinone and BrCHCHCOCH$_3$. To a solution of about 10 mmoles of (S)-5-trityloxymethyl-2-oxazolidinone in 40 mL tetrahydrofuran (THF) at 4° C., 10 mmoles NaH as a 60% suspension in hexane is added. The reaction mixture was stirred for about 10 minutes under nitrogen at 0° C. and then warmed up to room temperature and stirred for an additional two hours. Then, about 10 mmoles of BrCHCHCOCH$_3$ is added and the reaction mixture stirred at room temperature for about eight hours. Afterwards, the reaction is quenched by adding 20 mL 20% NH$_4$Cl. The organic layer is removed and saved. The aqueous layer is extracted two times with 40 mL aliquots of THF. The THF extracts are combined with the saved organic layer and the mixture dried with 2.5 g anhydrous Na$_2$SO$_4$. The mixture is then concentrated in vacuo to provide (S)-3-(3-butene-2-one)-5-trityloxymethyl-2-oxazolidinone as a crude product. The crude product is purified by flash column chromatography using 40% EtOAc:Hexane followed by 60% EtOAc:Hexane. The product is compared to the starting material by TLC using 40% EtOAC/Hexane as the solvent.

In the second step, the trityl group is removed from the (S)-3-(3-butene-2-one)-5-trityloxymethyl-2-oxazolidinone as in Example 4 to produce (S)-3-(3-butene-2-one)-5-hydroxymethyl-2-oxazolidinone.

In the third step, the substituted oxazolidinone is produced in a reaction comprising the (S)-3-(3-butene-2-one)-5-hydroxymethyl-2-oxazolidinone and 7-chloro-2,1,3-benzoxadiazole-4-sulfonyl chloride. To about 1.0 mmoles of the ((S)-3-(3-butene-2-one)-5-hydroxymethyl-2-oxazolidinone in dry $CH_2Cl_2$ (8 mL $CH_2Cl_2$), 1.0 equiv. (1.1 mmoles) of pyridine is added and the reaction mixture stirred at room temperature. To this reaction mixture is added 1.0 equiv. of 7-chloro-2,1,3-benzoxadiazole-4-sulfonyl chloride. The reaction is stirred overnight at room temperature. Afterwards, an aliquot of the reaction is analyzed by TLC to determine whether complete conversion of the (S)-3-(3-butene-2-one)-5-hydroxymethyl-2-oxazolidinone to the substituted oxazolidinone has occurred. Thereafter, about 3 mL of 20% $NH_4Cl$ is added to the reaction mixture and the organic layer is removed and saved. The aqueous layer is extracted two times with 40 mL aliquots of $CH_2Cl_2$. The $CH_2Cl_2$ extracts are combined with the saved organic layer and the mixture is dried with 2.5 g anhydrous $Na_2SO_4$. The mixture is then concentrated in vacuo to provide a crude product of the substituted oxazolidinone. The crude product is analyzed by $^1$H-NMR, $^{13}$C NMR, HPLC, and TLC using an EtOAc:hexane (2:1) solvent system and is further purified by standard chromatography methods.

EXAMPLE 8

The substituted oxazolidinones were tested for antimicrobial activity as follows.

The following American Type Culture Collection (ATCC, 10801 University Boulevard, Manassas, Va.) quality control strains were selected for the initial screening of the antimicrobial properties of the substituted oxazolidinones as suggested by the NCCLS: *Enterococcus faecalis* 29212, *Escherichia coli* 25922, *Pseudomonas aeruginosa* 27853, and *Staphylococcus aureus* 29213. See, NCCLS document M7-A5. Methods for Dilution Antimicrobial Susceptibility Tests for Bacteria That Grow Aerobically; Approved Standard-Fifth Edition. Volume 20, Number 2. January 2000, (ISBN 1-56238-394-9) and Lorian V. Antibiotics. Laboratory Medicine. 4th ed. Baltimore: Williams and Wilkins, pp. 52-111 (1996). For subsequent testing, the following strains have been used: *Staphylococcus aureus* NRS4 (992; HIP5836; New Jersey) (Smith et al., New Engl. J. Med. 340: 493-501 (1999); Tenover et al., J. Clin. Microbiol. 36: 1020-1027 (1998)), *Staphylococcus aureus* NRS3 (963sm; HIP5827; Michigan) (Smith et al., ibid.; Tenover et al., ibid.), *Staphylococcus aureus* NRS103 (Becker) (Karakawa and Vann, Sem. Infect. Dis. 4: 285 (1982), *Staphylococcus aureus* NRS102 (Reynolds) Karakawa and Vann, ibid; McMurray et al., JID 162: 759-762 (1990)), *Staphylococcus epidermidis* NRS101 (ATCC 35984), *Streptococcus pneumoniae* (ATCC 49619), *Enterococcus faecalis* (ATCC 51299), and *Staphylococcus aureus* (ATCC 43300.

Stock cultures of these strains were obtained by seeding colonies from overnight streak plates (Tryptic Soy Agar II (TSAII) and 5% sheep's blood (SB) agar plates: Becton Dickinson, CA#2211261) into sterile Mueller-Hinton Broth (MHB)(Becton Dickinson, CA#211443) and growing the suspensions to mid-late log phase in 13 mL screw-cap tubes. Glycerol (Sigma, CA#G-6279) was sterilized by autoclaving for 15 minutes at 121° C. in 6 mL volumes, and then stored at 2-8° C. This was diluted to 20% in $dH_2O$, and then added 1:1 (250 µL:250 µL, 10% final glycerol concentration) to the logarithmically growing bacterial suspension of each strain. Tubes were frozen and stored at −70° C. Purity of the stock cultures was tested by thawing one tube of each strain in a water bath at 37° C. and plating them on TSAII with 5% SB. Plates were incubated overnight at 37° C. and colonies were examined for morphology. Growth curves and approximate CFU/mL were also obtained.

DMSO susceptibility determinations were performed as follows. DMSO (Alfa Aesar, CA#22914) was diluted to 2× the final starting concentration of 20% in MHB, pH 7.36 (this was the consistent pH value of MHB) (should be between 7.2-7.4 according to NCCLS). Two-fold serial dilutions were performed in 15 mL conical tubes and poured into sterile reservoirs. Using an 8-channel micropipetman, 50 µL from each reservoir was transferred to every well in the corresponding column (1-11) of a sterile 96-well, U-bottom microplate (Nalge Nunc, Intl., CA#262162). As a positive growth control, 50 µL of MHB alone was added to each well of Column 12. Bacteria were grown overnight on TSAII+5% SB, and 3-4 colonies were seeded into 6 mL of sterile MHB in 13 mL screw cap tubes. Tubes were grown at 35° C. to mid-log phase, and were diluted to an optical density of 0.12 at 625 nm (or approx. $1\times10^8$ CFU/mL), using 0.9% sterile saline. This solution was further diluted 1:100 with 0.9% sterile saline ($1\times10^6$ CFU/mL), and 50 µL was added to each well for a final inoculum of $1\times10^5$ CFU/mL. As a negative growth control, well H12 was inoculated only with 0.9% sterile saline. The plate was tightly fitted with sealing tape (Corning Costar, CA#3095) and was incubated for a period of 18 hours at 35° C., after which growth was observed. 2.5% DMSO was determined to be the smallest concentration of DMSO to exhibit no visual effects on bacterial growth as compared with the positive controls for all strains tested. This was confirmed by performing colony counts to assess cell viability in the presence of DMSO. For each strain, 10 µL was removed from one of the inoculated wells containing 2.5%, 0.15%, and 0% DMSO (after mixing). This was diluted 1:100000 in sterile 0.9% DMSO, plated on TSAII+5% SB, and grown overnight at 35° C. Plates were then observed for differences in the number of viable colonies (theoretically, each colony arises from a single cell) based on the varying concentrations of DMSO. No differences were observed.

High purity substituted oxazolidinones prepared according to the method of the present invention and a ZYVOX standard (ZYVOX is a trade name for linezolid available from Pharmacia Corporation) were provided by Synthon Corporation, Monmouth Junction, N.J. Compounds were dissolved at 10 mg/mL in DMSO, as after a dilution of approx. 39.0 to reach the desired final starting concentration of 256 µg/ml, the concentration of DMSO is approximately 2.5%. Compounds were then stored at room temperature (25° C.) in the dark.

Antimicrobial susceptibility screening was as follows. All compounds were initially screened for activity in duplicate at 256 µg/mL (2.5% DMSO), including ZYVOX, the positive control for antimicrobial activity. A single well of bacterially inoculated 2.5% DMSO served as a positive control for bacterial growth, while a well of DMSO inoculated with of 50 µL of sterile 0.9% saline served as a negative growth control. Controls were prepared on every microplate, so that 46 was the maximum number of compounds that were screened per plate. Broth was pipetted into sterile microcentrifuge tubes, to which the compounds were then added (1:19.53 dilution or 2× final concentration). Each tube was vortexed, and 50 µL was immediately transferred to the microplate wells for each strain. Solubility was assessed by visual observation. MB (medium broth solubility) was recorded if the solution appeared only slightly cloudy. LB (low broth solubility) was recorded if the solution was extremely cloudy, and especially if larger, clumpy precipitates formed. Bacteria were grown as described above, although absorbance was measured at 650 nm and bacteria were diluted to an initial OD of 0.12-0.15. Bacteria were then further diluted 1:100 with 0.9% sterile saline. Within 15 minutes of this final dilution, 50 µL of this suspension was added to each well for a final volume of 0.1 L, and a final bacterial concentration of $1\times10^5$ CFU/mL (except for the negative control well). Plates were grown as above and all observations were recorded.

Compounds exhibiting activity at this concentration were then screened for their MICs (minimum inhibitory concentration) in duplicate, at concentrations ranging from 256-0.25 µg/mL (columns 1-11) using the broth microdilution method. Two-fold dilutions were obtained using an 8-channel micropipetman and tips were changed between each column transfer, after mixing 10 times and expelling the maximum amount of fluid. The MIC was defined as the lowest concentration of test compound that inhibited visible growth after a period of 18 hours incubation at 35° C. Bacteria were prepared, and the microwell plates were incubated as described above. In addition, bacteria were routinely sampled before addition to the wells. From the pre-well concentration, samples were diluted 1:200 with 0.9% sterile saline. At this concentration, 100 µL was plated and the remaining sample was diluted 1:10. 100 µL of this was then also spread-plated onto TSAII+5% SB and grown overnight at 35° C. Colonies were counted and multiplied by the dilution factor to obtain starting CFU/mL. As a positive MIC control, ZYVOX was tested in parallel for each strain, and the dilution of 5% (2× final concentration) DMSO served as a positive growth control. To control for variation between the volume transferred by each tip of the 8-channel micropipetman, 5% (2× final concentration) DMSO was added to column 12 using the micropipetman.

All wells, but that of the negative control (H12), were inoculated with the same bacterial suspension resulting in a final starting concentration of $1\times10^5$ CFU/mL. The negative control was inoculated with 0.9% sterile saline.

At this time, a total of 1625 substituted oxazolidinones have been successfully screened for activity at 256 µg/mL (Compounds 1422, 1474, 147$, 1595 were absent). Of these, 71 were tested against *Staphylococcus aureus* (Gram positive), 60 were tested against *Enterococcus faecalis* (Gram positive), and one compound tested against *Escherichia coli* (Gram negative) have proven effective with MICs at or below 256 µg/mL.

Tables 1 and 2 show the antimicrobial activity for several of the substituted oxazolidinones. Table 1 further shows that several were also able to inhibit the growth of myeloid, erythroid, and megakaryocytic cells. Table 3 shows several substituted oxazolidinones which have been found to be particularly antimicrobial. In general, many of the substituted oxazolidinones were as effective as ZYVOX. Thus, the results show that many of the substituted oxazolidinones prepared according to the process herein have antimicrobial applications, in particular, as antimicrobial agents against drug resistant strains of gram positive bacteria.

TABLE 1

In Vitro Antimicrobial Test Results for Several Substituted Oxazolidinones

| | $MIC_{90-100}$ (µg/mL) | | | | | | | | Bone Marrow Cell Growth Inhibition ($IC_{50}$ µg/mL) | | |
|---|---|---|---|---|---|---|---|---|---|---|---|
| | SA | EF | MR SA | MR SA | VS EF | MR SA | Pen. R SA | Ref SA | Myeloid | Erythroid | Megakaryocytic |
| Strain | ATCC 29212 | ATCC 29213 | New Jersey | Michigan | ATCC 51299 | ATCC 43300 | Reynolds | Becker | | | |
| Compound | | | | | | | | | | | |
| 1687 | 2 | 2 | 2 | 2 | | | 3 | 3 | 20 | 0.01 | 6 |
| 1705 | 2 | 4 | 3 | 2 | 8 | 4 | 32 | 4 | 5 | 0.5 | 0.08 |
| 1715 | 2 | 4 | 3 | 3 | 8 | 4 | 32 | 8 | 5 | 0.7 | 0.08 |
| 1808 | 4-8 | 2 | 4 | 3 | 2 | 8 | 16 | 16 | | | |
| 1809 | 4-8 | 4 | 3 | 3 | 2 | 4 | 8 | 4 | | | |
| 2278 | 4 | 2 | 4 | 4 | | | 8 | 8 | | | |
| 2405 | 2 | 2 | 4 | 2 | | | 8 | 4 | | | |
| 2428 | 4 | 4 | 4-8 | 4-8 | | | 32 | 16 | | | |
| 1021 | 16-32 | 250 | 256 | 256 | >256 | 100 | | | 20 | 20 | 0.9 |
| 1192 | 4-8 | 250 | 256 | 256 | >256 | 128 | | | 5 | 0.05 | 0.6 |
| 126 | 8-16 | 250 | 256 | 256 | 256 | 256 | | | 5 | 0.02 | 9.0 |
| 207 | 64-125 | 250 | | | | | | | 0.8 | 0.2 | 3.0 |
| 253 | 8-16 | 250 | 256 | 256 | >256 | >256 | | | 30 | 7 | 10.0 |
| 971 | 4-8 | 250 | 256 | 256 | >256 | 100 | | | 40 | >0.01 | 30.0 |
| ZYVOX | 2 | 2 | 2 | 2 | 0.5 | 1 | 1 | 1 | 20 | 0.08 | 4 |

VR is vancomycin resistant, VS is vancomycin sensitive, MR is methicillin resistant, MS is methicillin sensitive, SA is *Staphylococcus aureus*, and EF is *Enterococcus faecalis*.

TABLE 2

| COMPOUND | COMPOUND # | MIC$_{(90-100)}$(ug/mL) SA-ATCC29213 | MIC$_{(90-100)}$(ug/mL) EF-ATCC 29212 |
|---|---|---|---|
| | 34 | 250 | |
| | 108 | 62.5 | |
| | 110 | 31.3 | |
| | 126 | 15.6 | |
| | 235 | 62.5 | |
| | 236 | 31.3 | |
| | 250 | 250 | |
| | 253 | 15.6 | |

TABLE 2-continued

| COMPOUND | COMPOUND # | MIC$_{(90-100)}$(ug/mL) SA-ATCC29213 | MIC$_{(90-100)}$(ug/mL) EF-ATCC 29212 |
| --- | --- | --- | --- |
| | 254 | 125 | |
| | 255 | 62.5 | 250 |
| | 260 | 250 | |
| | 266 | 15.6 | |
| | 272 | 250 | |
| | 276 | 125 | 250 |
| | 285 | 62.5 | 250 |
| | 291 | 250 | |

TABLE 2-continued

| COMPOUND | COMPOUND # | MIC$_{(90-100)}$(ug/mL) SA-ATCC29213 | MIC$_{(90-100)}$(ug/mL) EF-ATCC 29212 |
|---|---|---|---|
| [structure with pent-2-ynyl oxazolidinone and 4-nitrophenylsulfonate] | 294 | 31.3 | 250 |
| [structure with 3-methoxybenzyl oxazolidinone and chlorobenzofurazan sulfonate] | 323 | 250 | 125 |
| [structure with acetamido-methylthiazole sulfonate, oxazolidinone, and 2,4-dimethoxyphenacyl] | 324 | 62.5 | 250 |
| [structure with 4-nitrophenylsulfonate, oxazolidinone, and 2-furoyl] | 334 | 62.5 | |
| [structure with chlorobenzofurazan sulfonate, oxazolidinone, and 4-fluorophenacyl] B2-HP-K10 C$_{18}$H$_{13}$ClFN$_3$O$_7$S Exact Mass: 469.01 | 369 | 250 | 31.3 |
| [structure with 4-nitrophenylsulfonate, oxazolidinone, and ethyl acrylate] B51-HP-K2 C$_{15}$H$_{18}$N$_2$O$_9$S Exact Mass: 402.07 | 388 | 125 | |

TABLE 2-continued

| COMPOUND | COMPOUND # | MIC$_{(90-100)}$(ug/mL) SA-ATCC29213 | MIC$_{(90-100)}$(ug/mL) EF-ATCC 29212 |
|---|---|---|---|
| B2-HP-K10A<br>C$_{18}$H$_{13}$ClFN$_3$O$_7$S<br>Exact Mass: 469.01 | 401 | 250 | 62.5 |
|  | 533 | 125 |  |
|  | 589 | 125 |  |
|  | 669 | 62.5 |  |
|  | 674 | 250 | 125 |
|  | 695 | 62.5 |  |
|  | 771 | 15.6 |  |

TABLE 2-continued

| COMPOUND | COMPOUND # | MIC(90-100)(ug/mL) SA-ATCC29213 | MIC(90-100)(ug/mL) EF-ATCC 29212 |
|---|---|---|---|
| | 860 | 64 | |
| | 870 | 16 | |
| | 905 | 256 | |
| | 921 | 256 | |
| | 924 | 256 | |
| | 929 | 64 | |
| | 942 | 32 | |
| | 952 | 32 | |

TABLE 2-continued

| COMPOUND | COMPOUND # | MIC$_{(90\text{-}100)}$(ug/mL) SA-ATCC29213 | MIC$_{(90\text{-}100)}$(ug/mL) EF-ATCC 29212 |
| --- | --- | --- | --- |
| | 971 | 8 | |
| | 1001 | 64 | 125 |
| | 1021 | 32 | |
| | 1026 | 256 | |
| | 1058 | 256 | |
| | 1063 | 16 | |
| | 1066 | 256 | |

TABLE 2-continued
| COMPOUND | COMPOUND # | MIC(90-100)(ug/mL) SA-ATCC29213 | MIC(90-100)(ug/mL) EF-ATCC 29212 |
|---|---|---|---|
| 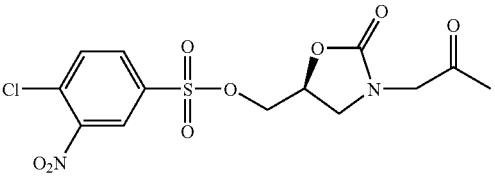 | 1081 | 256 | |
| 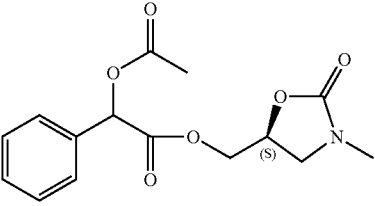 | 1097 | 32 | |
| 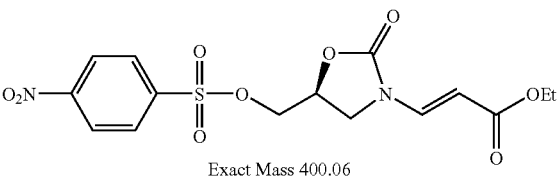 Exact Mass 400.06 | 1160 | 128 | |
| 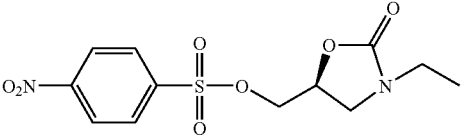 | 1192 | 8 | |
| 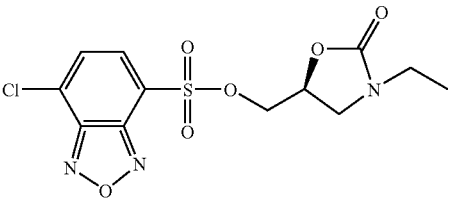 | 1196 | 256 | 128 |
| 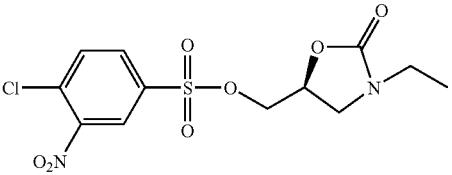 | 1210 | 256 | |
| 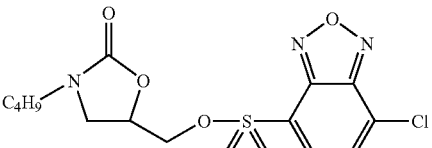 | 1411 | 64 | 128 |

TABLE 2-continued

| COMPOUND | COMPOUND # | MIC(90-100)(ug/mL) SA-ATCC29213 | MIC(90-100)(ug/mL) EF-ATCC 29212 |
| --- | --- | --- | --- |
| 2,5-dichlorothiophene-3-carboxylate linked to oxazolidinone-N-CH=CH-C(O)N(CH3)2<br>Exact Mass. 392.00 | 1629 | 256 | 64 |
| 2-phenylthiazole-4-carboxylate linked to oxazolidinone-N-CH=CH-C(O)N(CH3)2<br>Exact Mass. 401.10 | 1631 | 16 | 16 |
| 4-nitrobenzenesulfonate linked to oxazolidinone-N-CH=CH-C(O)N(CH3)2<br>Exact Mass. 399.07 | 1632 | 16 | 64 |
| N-(4-nitrophenyl)oxazolidinone-CH2-O-S-(4-nitrophenyl) | 1808 | 8 | 2 |
| N-(4-nitrophenyl)oxazolidinone-CH2-O-C(O)-O-(4-nitrophenyl) | 1809 | 8 | 4 |
| N-(4-nitrophenyl)oxazolidinone-CH2-O-(5-hydroxynaphthalen-1-yl) | 1960 | 32 | 8 |
| N-(4-nitrophenyl)oxazolidinone-CH2-O-julolidinyl | 1965 | 32 | 8 |

TABLE 2-continued

| COMPOUND | COMPOUND # | MIC(90-100)(ug/mL) SA-ATCC29213 | MIC(90-100)(ug/mL) EF-ATCC 29212 |
|---|---|---|---|
| (structure) | 1985 | 8 | 124 |
| (structure) | 1998 | 16 | 64 |
| Exact Mass: 405.06 | 2017 | 16 | 8 |
| Exact Mass: 437.99 | 2019 | 16 | 32 |
| Exact Mass: 450.01 | 2020 | 64 | 124 |
| Exact Mass: 338.06 | 2023 | 64 | 32 |
| Exact Mass: 368.07 | 2025 | 64 | 32 |

TABLE 3

| External ID | internal ID | Structure |
|---|---|---|
| SCC 001 | 126 | 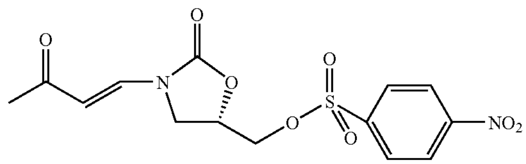 |
| SCC 002 | 207 | 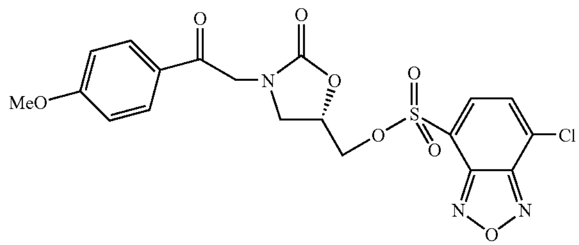 |
| SCC 003 | 253 | 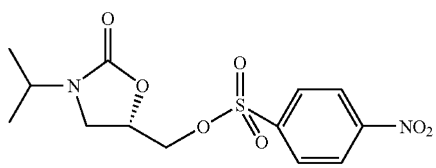 |
| SCC 004 | 971 | 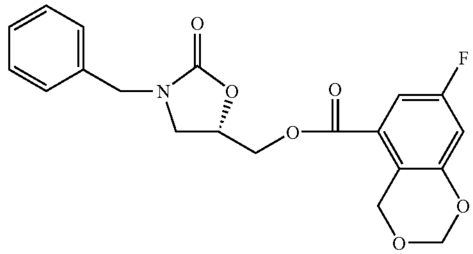 |
| SCC 005 | 1021 | 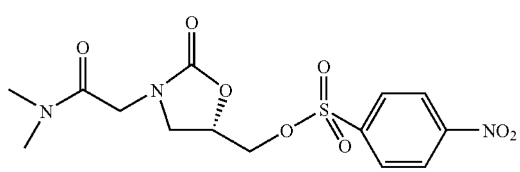 |
| SCC 006 | 1192 | 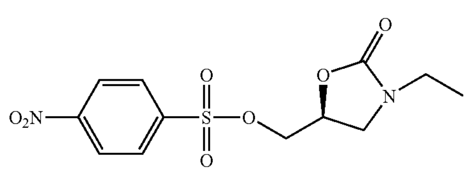 |
| SCC 007 | 1687 | 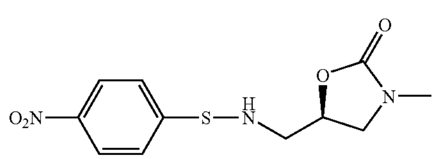 |
| SCC 008 | 1705 | 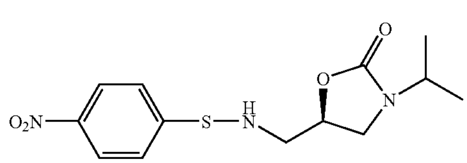 |

TABLE 3-continued

| External ID | internal ID | Structure |
| --- | --- | --- |
| SCC 009 | 1715 | 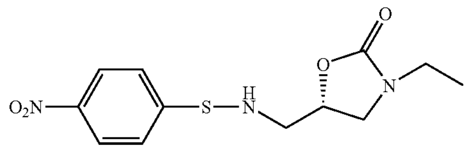 |
| SCC 010 | 1808 | 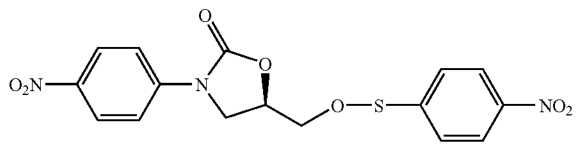 |
| SCC 011 | 1809 | 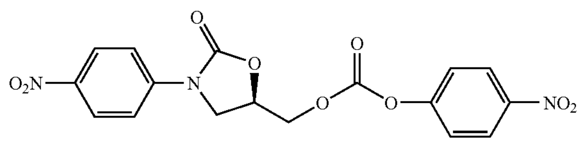 |
| SCC 012 | 2278 | 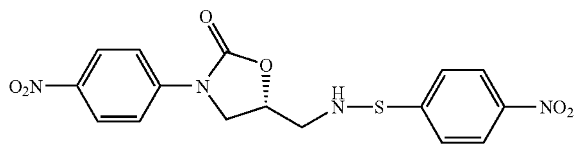 |
| SCC 013 | 2405 | 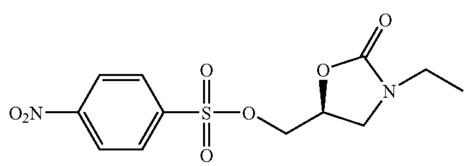 |
| SCC 014 | 2428 | 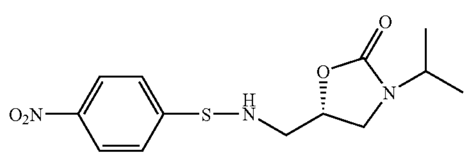 |
| SCC 015 | 2570 | 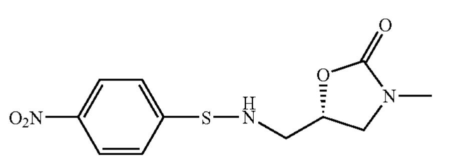 |
| Standard | Zyvox | 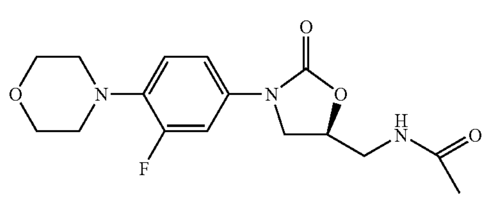 |

EXAMPLE 9

This example shows the synthesis of various examples of the substituted oxazolidinones.

A. Sulphonates and Esters

1. Synthesis of Precursors

N-Ethyl 5-hydroxymethyl-2-oxazolidinone

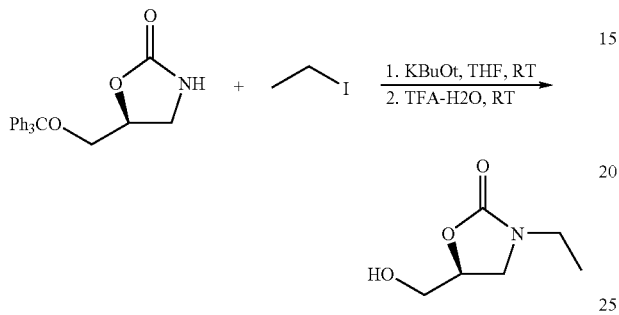

To a solution containing the oxazolidinone (5.0 g, 13.9 mmol) in dry THF (50 mL) was added potassium-t-butoxide (2.03 g, 18.1 mmol, 1.3 equiv) at RT and stirred under $N_2$ atm for 0.5 h. To this solution was added ethyl iodide (3.25 g, 20.8 mmol, 1.5 equiv) and stirred for 2 h after which TLC (1:1 hex-EtOAc) showed completion of reaction. The reaction was quenched by adding satd. $NH_4Cl$ solution. THF was removed on rotovap and residue diluted with $CH_2Cl_2$ (100 mL). Organic layer washed with brine and dried ($MgSO_4$). Removal of solvent gave a light yellow oil. This crude product was taken in $CH_2Cl_2$ (50 mL). Added trifluoroacetic acid (4.75 g, 41.7 mmol, 3.0 equiv)-water (1.0 g, 55.5 mmol, 4 equiv) dropwise and stirred for 2 h. The solvent was removed on rotovap and residue purified by flash column chromatography (silica gel, EtOAc) to get the product as a colorless oil (1.3 g, 66% in two steps).

$^1$H NMR (CDCl$_3$, 200 MHz): δ 4.6 (m, 1H), 4.1 (s, 1H), 3.88 (dd, 1H) 3.6 (m, 5H), 1.2 (t, 3H). $^{13}$C NMR (CDCl$_3$, 50 MHz): δ 157.86, 73.45, 62.69, 45.01, 38.59, 12.22.

A similar procedure was followed for the alkylation of the oxazolidinone with B12 (R&S), B38(R&S), B39, E11(R&S), E16(R&S), E81(R&S), G3(R&S), G4-oxa-C4, W14, W15, W17, W19 and W23.

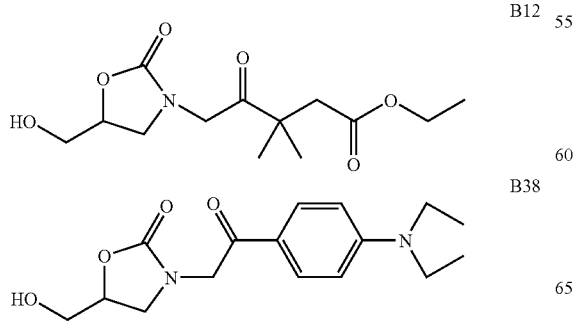

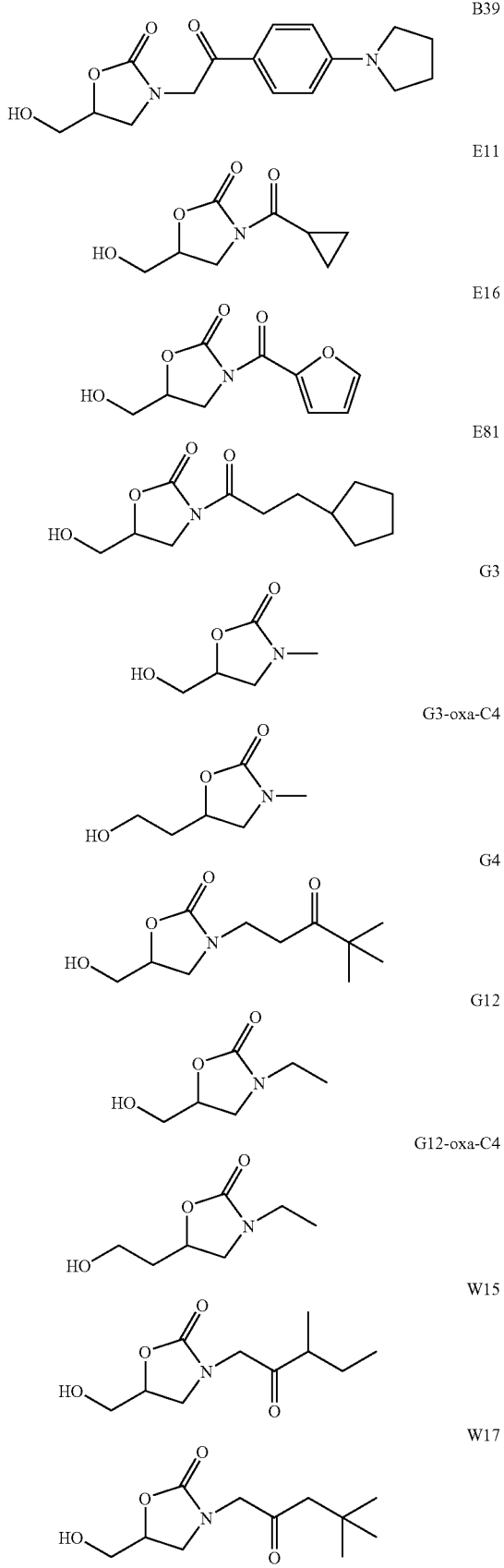

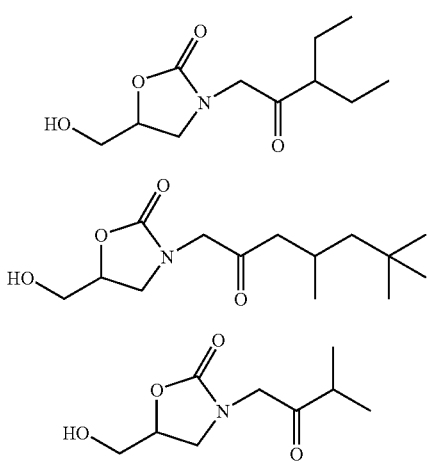

N-isopropyl-5-trityloxymethyl-2-oxazolidinone

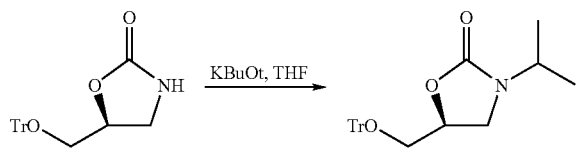

To a solution containing the oxazolidinone (15.0 g, 41.7 mmol) in dry THF (150 mL) was added potassium-t-butoxide (8.4 g, 75.0 mmol, 1.8 equiv) at RT and stirred under $N_2$ atm for 0.5 h. To this solution was added isopropyl iodide (7.8 g, 45.9 mmol, 1.1 equiv) and stirred at 70° C. for 15 h. The reaction was quenched by adding satd. $NH_4Cl$ solution. THF was removed on rotovap and residue diluted with $CH_2Cl_2$ (200 mL). Organic layer washed with brine and dried ($MgSO_4$). Removal of solvent gave a light yellow oil. The residue was purified by flash column chromatography (silica gel, hexane-EtOAc, 4:1) to get the product as a colorless solid (15.0 g, 90%).

$^1$H NMR (CDCl$_3$, 200 MHz): δ 7.3 (m, 15H), 4.56 (m, 1H), 4.1 (m, 1H), 3.3 (m, 4H), 1.1 (m, 6H). $^{13}$C NMR (CDCl$_3$, 50 MHz): δ 157.0, 143.4, 128.6, 127.9, 127.2, 86.8, 71.9, 64.0, 44.6, 41.6, 19.8, 19.6.

Synthesis of ethyl (2-bromo)-t-butyl ketone (Class G4):

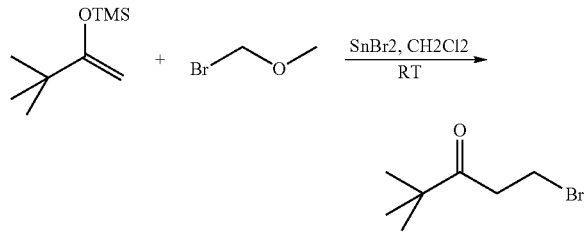

To a suspension of SnBr$_2$ (242 mg, 5 mol %) in CH$_2$Cl$_2$ (5.0 mL) was added pinacolone trimethylsilyl enol ether (3.0 g, 17.4 mmol) in CH$_2$Cl$_2$ (2.0 mL) followed by bromomethyl methylether (3.26 g, 26.1 mmol, 2.1 mL, 1.5 equiv) in CH$_2$Cl$_2$ (2.0 mL). Stirred at RT for 3.5 h after which TLC showed complete conversion. The solvent was removed on rotovap to get an orange yellow liquid. The crude product was passed through a short pad of silica packed in hexane and the product was eluted with 5% EtOAc-hexanes as a pale yellow liquid (2.65 g, 79%).

$^1$H NMR(CDCl$_3$, 200 MHz): δ 3.54 (t, 2H), 3.06 (t, 2H), 1.12 (s, 9H). $^{13}$C NMR (CDCl$_3$, 50 MHz): δ 212.4, 43.9, 39.6, 26.0.

Homologation of t-butylacetyl chloride

t-Butylacetyl chloride (4.0 g, 29.7 mmol) was added dropwise to a solution of trimethylsilyldiazomethane (37.1 mL, 74.3 mmol) in CH$_3$CN-THF (100 mL, 1:1) at 0° C. added the t-butylacetyl chloride (4.0 g, 29.7 mmol) dropwise and then refrigerated for 40 h. Solvent was removed on rotovap and residue diluted with CH$_2$Cl$_2$ (100 mL). Washed with satd. NaHCO$_3$ (50 mL) solution followed by brine, dried (MgSO$_4$) and concentrated to an yellow liquid (4.5 g). This product was taken in THF (25 mL) and cooled to 0° C. and added HBr (48%) (8.4 g, 104.0 mmol, 3.5 equiv) dropwise. After the addition, reaction mixture stirred at that temp for 30 min. Diluted with CH$_2$Cl$_2$ (75 mL) and washed with satd. NaHCO$_3$ (50 mL) followed by brine, dried (MgSO$_4$) and concentrated to an yellow liquid. Purified by column chromatography (silica gel) and the product was eluted with 2-4% EtOAc-hexane. Pale yellow liquid (3.3 g, 82.5%).

$_1$H NMR (CDCl$_3$, 200 MHz): δ 3.84 (s, 2H), 2.48(s, 2H), 0.98(s, 9H). $^{13}$C NMR (CDCl$_3$, 50 MHz): δ 200.8, 51.7, 36.2, 31.1, 29.4.

Following a similar procedure W14, W15, W19, W23 were prepared from corresponding acid chlorides.

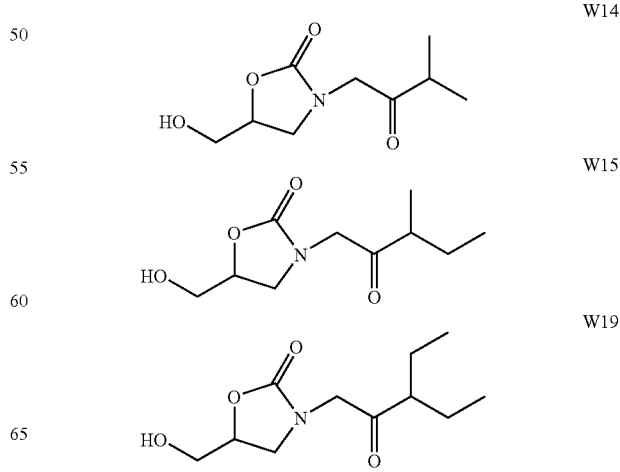

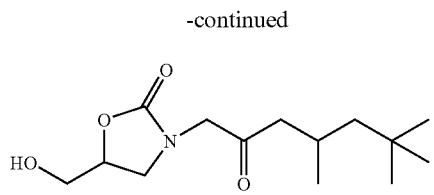

Synthesis of C4-Oxazolidinone
4,4-dibenzylamino-1,3-(S)butanediol

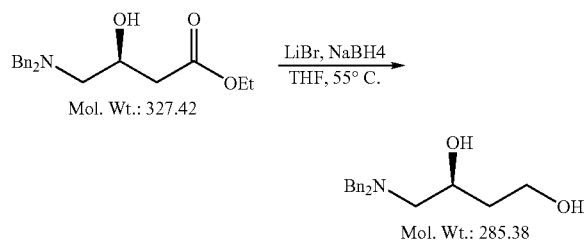

R.B charged with LiBr (14.8 g, 170.8 mmol, 4.0 equiv), NaBH₄ (6.37 g, 170.8 mmol, 4.0 equiv) and THF (125 mL) and stirred at 50° C. for 2 h. Added the ester (14.0 g, 42.7 mmol, 1.0 equiv) in THF (25 mL) slowly and stirring continued for 2 h (TLC no SM). Reaction mixture cooled to RT and added satd. NH₄Cl dropwise (cool in ice-bath) till no gas evolution. Most of the THF was removed on rotovap and residue diluted with EtOAc (250 mL). Washed with brine, dried (MgSO₄) and concentrated to a colorless oil and purified by column chromatography (70% EA-hexane). Product obtained as a colorless syrup (yield: 9.2 g, 77%).

$^1$H NMR (CDCl₃, 200 MHz): δ 7.2(m, 10H), 3.8 (m, 6H), 3.4 (d, 2H), 2.4 (m, 2H), 1.6 (m, 2H). $^{13}$C NMR (CDCl₃, 50 MHz): δ 138.3, 128.9, 128.3, 127.2, 66.8, 60.7, 59.5, 58.4, 36.3.

4-Amino-1,3-(S)butanediol

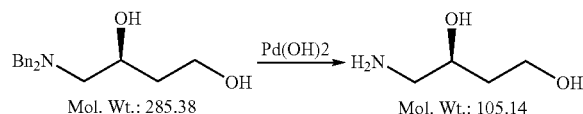

THF-MeOH (30+40 mL) suspension containing the diol (9.0 g, 31.5 mmol) and wet Pd(OH)₂ (10%, 3.5 g) was hydrogenated under 40 psi (2.81 kgf/cm²) for 20 h. The solution warmed and the hot solution filtered through a short pad of celite. Washed several times with methanol (towards the end few drops of TEA added). Removal of solvent gave a colorless oil (3.3 g, quantitative).

4-(Benzyloxycarbonyl)-amino-1,3-(S)butanediol

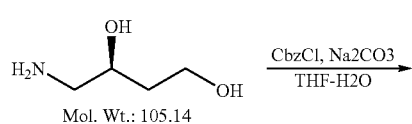

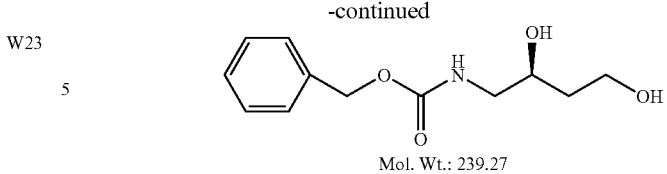

R. B. charged with the amine (3.3 g, 31.3 mmol, 1.0 equiv) and THF-H₂O (20+40 mL). Added Na₂CO₃ (4.0 g, 37.8 mmol, 1.2 equiv) and cooled to 5° C. Added CbzCl (6.45 g, 37.8 mmol, 5.4 mL, 1.2 equiv) dropwise keeping temp. below 5° C. and stirred at that temp. for 3 h. Diluted with water (100 mL) and extracted into EtOAc (3×100 mL). Washed with brine, dried (MgSO₄) and concentrated to a colorless oil which solidified on keeping (9.0 g).

$^1$H NMR (CDCl₃, 200 MHz): δ 7.2(s, 5H), 5.6 (s, 1H), 5.0 (s, 2H), 3.5 (m, 7H), 1.6 (m, 2H). $^{13}$C NMR (CDCl₃, 50 MHz): δ 157.1, 136.2, 128.4, 128.0, 127.9, 70.2, 66.8, 60.4, 46.9, 35.7.

4-(Benzyloxycarbonyl)-amino-1 (O-trityl)-3-(S)butanediol

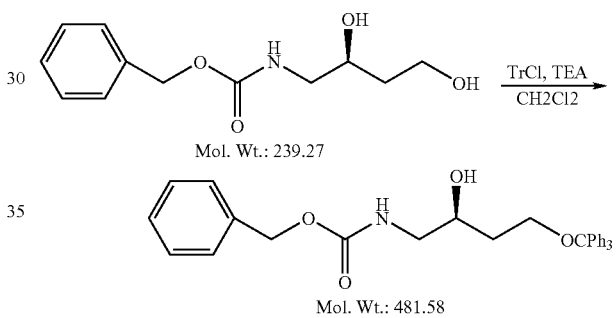

Reaction mix. containing the crude diol (~9.0 g, 31.5 mmol, 1.0 equiv), TrCl (10.5 g, 37.6 mmol, 1.2 equiv) and TEA (7.96 g, 78.6 mmol, 2.5 equiv) in CH₂Cl₂ (100 mL) stirred at RT for 21 h. The reaction mixture washed with water, brine and dried (MgSO₄) and concentrated to a pale yellow oil (20.0 g).

5-trityloxyethyl-2-oxazolidinone

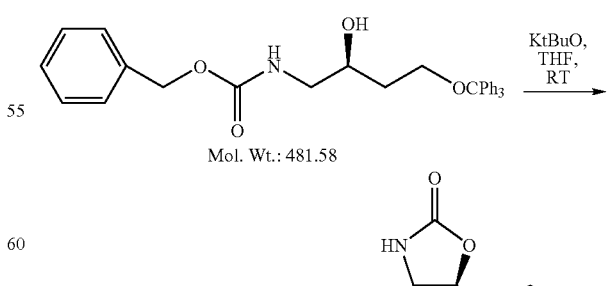

The above crude product (20 g, ~31.5 mmol based on purity) taken in anhydrous THF (150 mL) and treated with KtBuO (7.84 g, 70 mmol, 2.2 equiv) and stirred at RT for 7 h. Diluted with water (100 mL), bulk of the THF removed on rotovap. Residue extracted with EtOAc (3×100 mL), washed with brine, dried (MgSO4) and concentrated to a light brown oil. Purified by column chromatography (40% EtOAc-hexane) to get a pale yellow foamy oil which solidifies (10.7 g, 91% in three steps).

$^1$H NMR (CDCl$_3$, 200 MHz): δ 7.25 (m, 15H), 5.75 (s, 1H), 4.8 (m, 1H), 3.6 (t, 1H), 3.2 (t, 3H), 2.0 (m, 2H). $^{13}$C NMR (CDCl$_3$, 50 MHz): δ 159.6, 143.8, 128.5, 127.8, 127.0, 86.9, 75.0, 59.3, 46.0, 35.2.

N-(4-nitrophenyl)-5-trityloxymethyl-2-oxazolidinone

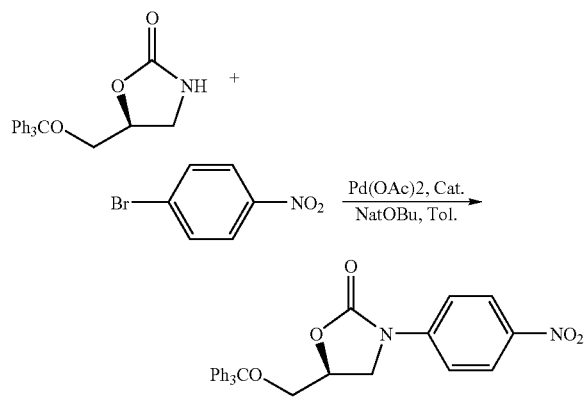

The reaction mixture containing the oxazolidinone (5.0 g, 13.9 mmol), 4-bromonitrobenzene (4.2 g, 20.8 mmol, 1.5 equiv), 1,1' bis(diphenylphosphinoferrocene) (0.77 g, 1.39 mmol, 0.1 equiv), Pd(OAc)$_2$ (0.31 g, 1.39 mmol, 0.1 equiv) and sodium-t-butoxide (2.0 g, 20.8 mmol, 1.5 equiv) in dry toluene (130 mL) was stirred under N$_2$ atm at 110° C. for 8 h. The solvent was removed on rotovap and the dark residue was chromatographed on silica gel using 30% EtOAc-hexane to get the product as a dark yellow foamy solid (2.7 g, 41%).

$^1$H NMR (CDCl$_3$, 200 MHz): δ 8.2 (d, 2H), 7.6 (d, 2H), 7.2 (m, 15H), 4.8 (m, 1H), 4.2 (t, 1H), 3.9 (m, 1H), 3.8 (dd, 1H), 3.4 (dd, 1H). $^{13}$C NMR (CDCl$_3$, 50 MHz): δ 155, 145, 144, 129.5, 129.3, 129, 126, 118, 87, 72, 64, 47.

2. Synthesis of Library-Sulphonates and Esters

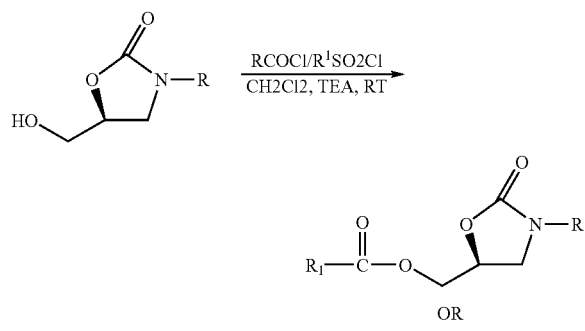

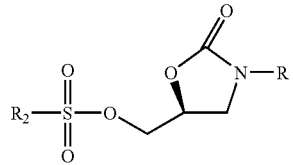

0.1 mM solution of the oxazolidinone in CH$_2$Cl$_2$ (25 mL) was prepared. From the above std. soln. syringed out 1.0 mL each (0.10 mmol) into 3 mL capped vials. Added triethylamine, 28 µL/vial (0.2 mmol, 2.0 equiv). Added 1.0 mL (0.10 mmol) of the stock solution (0.10 mM) of acid/sulphonyl chlorides into respective vials. The vial capped, the solution mixed well and kept aside at RT (20 h). All compounds purified by prep. TLC. (EtOAc-hexane). Silica gel band containing the product was taken in CH$_3$CN (15.0 mL). Filtered and washed with more CH$_3$CN (3 mL), and solvent removed on rotovap. The product obtained was transferred to small vials using CH$_2$Cl$_2$, all samples air dried and finally dried in vacuo. All samples were analyzed by LCMS.

Oxazolidinones and Sulphonyl/Acid Chlorides Used:

B12: K2, K4, K5, K8, K9, K10, K11, E112

B12 (R): K2, K10, K21, K22, K23, K83, E112

B38: K00, K0, K1, K2, K3, K4, K5, K6, K7, K8, K9, K10, K11, E0, E1, E4, E7, E8, E9, E10, E11, E15, E16, E112 B38 (R): K10, E112, E117, E120, E124, E136, E154,

B39: K00, K0, K1, K2, K3, K4, K5, K6, K7, K8, K9, K10, K11, E0, E1, E4, E7, E8, E9, E10, E11, E15, E16, E112

E11: K2, K4, K5, K8, K9, K10, K11, E112

E11 (R): K2, K10, K21, K22, K23, K83, E112

E16: K00, K0, K1, K2, K3, K4, K5, K6, K7, K8, K9, K10, K11, E14, E0, E1, E4, E7, E8, E9, E10, E11, E15, E16, E112

E16 (R): K2, K10, K21, K22, K23, K83, E8, E112

E81: K4, K5, K8, K9, K10, K11, E112

E81 (R): K2, K10, K21, K22, K23, K83, E112

G4: K2, K4, K5, K8, K10, K11, K21, K22, K23, K27, K30, K52, K54, K55, K56, K59, K60, K66, K83, K90, K91, K92, K93, K94, K95, K96, K97, E4, E11, E81, E82, E90, E107, E112, E113, E117, E159, E164, E168

G4 (R): K10, K21, K22, K23, K83,

G5: K00, K0, K1, K2, K3, K4, K5, K8, K9, K10, K11, K12, K21, K22, K23, K27, K30, K52, K54, K55, K56, K59, K60, K66, K83, K90, K91, K92, K93, K94, K95, K96, K97, K98, K99, K100, K101, K102, K117, E8, E11, E81, E82, E90, E107, E112, E113, E117, E120, E124, E136, E154, E159, E164, E168, E183, E184

G5 (R): K10, K11, K12, K21, K22, K23, K83

G9 (R): K2, K90, K91, K92, K93, K94, K95, K96, K97, K98, K99, K100, K101, K102, K117,

G12: K00, K0, K1, K2, K3, K4, K5, K8, K9, K10, K11, K12, K21, K22, K23, K27, K30, K52, K54, K55, K56, K59, K60, K66, K83, K90, K91, K92, K93, K94, K95, K96, K97, K98, K99, K100, K101, K102, K104, K105, K106, K107, K109, K110, K110, K112, K113, K114, K115, K117,

G12 (R): K2, K101, K102, K117, E112, E183, E184

G13 (R): K00, K0, K1, K2, K3, K4, K5, K8, K9, K10, K11, K12, K21, K22, K23, K27, K30, K52, K54, K55, K56, K59, K60, K66, K83, K90, K91, K92, K93, K94, K95, K96, K97, K98, K99, K100, K101, K102, K104, K105, K106, K107, K109, K110, K112, K113, K114, K115, E112, E183

W14: K101, K102, K104, K105, K106, K107, K109, K110, K112, K113, K114, K115, E112, E183

W15: K10, K21, K22, K23, K83, E8, E11, E81, E82, E90, E107, E112, E113, E117, E120, E124, E136, E154, E159, E164, E168

W17: K2, K4, K9, K10, K11, K12, K21, K27, K29, K30, K31, K52, K53, K54, K55, K56, K59, K60, K61, K66, K70 E8, E11, E81, E82, E90, E107, E112, E113, E159, E164, E168

W19: K10, K11, K12, K21, K22, K23, K83 E8, E11, E81, E82, E90, E107, E112, E113, E117, E120, E124, E136, E154, E157, E159, E164, E168

W23: K2, K4, K9, K10, K11, K21, K22, K23, K27, K29, K30, K31, K52, K53, K54, K55, K56, K59, K60, K61, K66, K70, K83, E8, E11, E81, E82, E90, E107, E112, E113, E117, E120, E124, E136, E154, E157, E159, E164, E168

G12-oxa-C4: K2, K10, K11, K93, K95, K96, K97, K100, K101, K102, K104, K105, K106, K107, K109, K110, K112, K115, K117, E183, E184

G3-oxa-C4: K2, K10, K11, K93, K95, K96, K97, K100, K101, K102, K104, K105, K106, K107, K109, K110, K112, K115, K117, E183, E184

Amines

A. Amides and Sulphonamides

1. Synthesis of Precursors (5R)-methanesulphonyloxymethyl-3-[(1R)-phenyl-ethyl-oxazolidine-2-one)

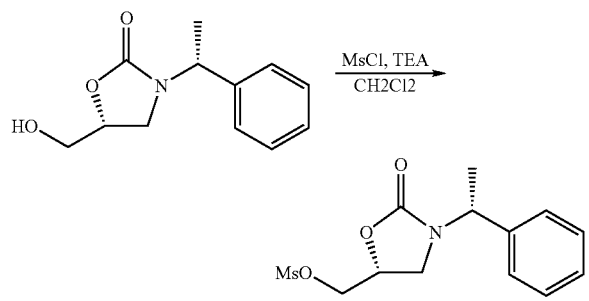

To an ice-cooled solution of the oxazolidinone (5.0 g, 22.6 mmol, 1.0 equiv) in CH$_2$Cl$_2$ (50 mL) was added TEA (4.57 g, 45.1 mmol, 2.0 equiv) followed by MsCl (3.36 g, 29.3 mmol, 1.3 equiv) dropwise and then stirred for 2 h. Diluted with CH$_2$Cl$_2$ (50 mL), washed with water (25 mL), brine, dried (MgSO$_4$) and concentrated to get an oil which solidified on keeping (6.5 g, 97%).

$^1$H NMR (CDCl$_3$, 200 MHz): δ 7.4 (s, 5H), 5.25 (m, 1H), 4.7 (m, 1H), 4.4 (m, 2H), 3.4 (m, 2H), 3.15 (s, 3H), 1.65 (d, 3H). $^{13}$C NMR (CDCl$_3$, 50 MHz): δ 156.1, 138.9, 128.5, 127.8, 126.7, 69.8, 68.8, 51.5, 41.3, 37.4, 16.0.

(5R)-Azidomethyl-3-[(1R)-phenylethyl-oxazolidine-2-one)

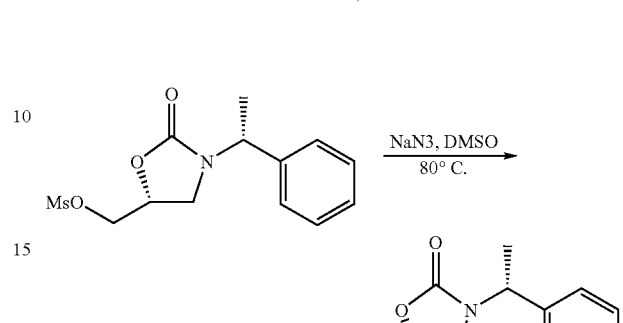

Reaction mixture containing the mesylate (6.5 g, 21.7 mmol) and NaN$_3$ (2.12 g, 32.6 mmol, 1.5 equiv) in DMSO (60 mL) was stirred at 80° C. for 3 h under N$_2$ atm. Then cooled to RT, diluted with water (100 mL) and CH$_2$Cl$_2$ (150 mL). Organic layer washed with brine, dried (MgSO$_4$) and concentrated to a pale yellow liquid. Crude product filtered through a short pad of silica using 40% EtOAc-hexane. Colorless oil which crystallized on keeping (5.0 g, 94%).

$^1$H NMR (CDCl$_3$, 200 MHz): δ 7.4 (s, 5H), 5.3 (m, 1H), 4.6 (m, 1H), 3.4 (m, 4H), 1.66 (d, 3H). $^{13}$C NMR (CDCl$_3$, 50 MHz): δ 156.4, 139.0, 128.6, 127.8, 126.8, 71.1, 53.1, 51.4, 42.3, 16.0

(5R)-Aminomethyl-3-[(1R)-phenylethyl-oxazolidine-2-one)

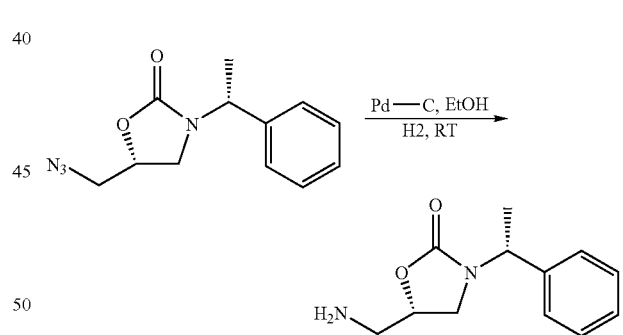

R.B charged with Pd—C (10%, 500 mg) and ethanol (10 mL). Added oxazolidinone (2.0 g) in ethanol (10 mL). Flushed with H$_2$ three times and stirred under H$_2$ overnight (17 h). Filtered through a short celite pad and washed with methanol. Solvent removed on rotovap to a light orange oil. Purified by silica gel column (20-50% MeOH in EtOAc) to get a light orange oil which solidifies on keeping (1.1 g, 62%).

$^1$H NMR (CDCl$_3$, 200 MHz): δ 7.4 (s, 5H), 5.3 (m, 1H), 4.6 (m, 1H), 3.4 (m, 2H), 3.1 (t, 2H), 2.8 (s, 2H), 1.66 (d, 3H). $^{13}$C NMR (CDCl$_3$, 50 MHz): δ 157.1, 139.4, 128.6, 127.8, 126.9, 73.7, 58.0, 51.4, 42.6, 16.2.

Amines belonging to classes G3, G5, G9, G12, B38 (both isomers), G3-oxa-C4, G12-oxa-C4 were prepared in a similar manner.

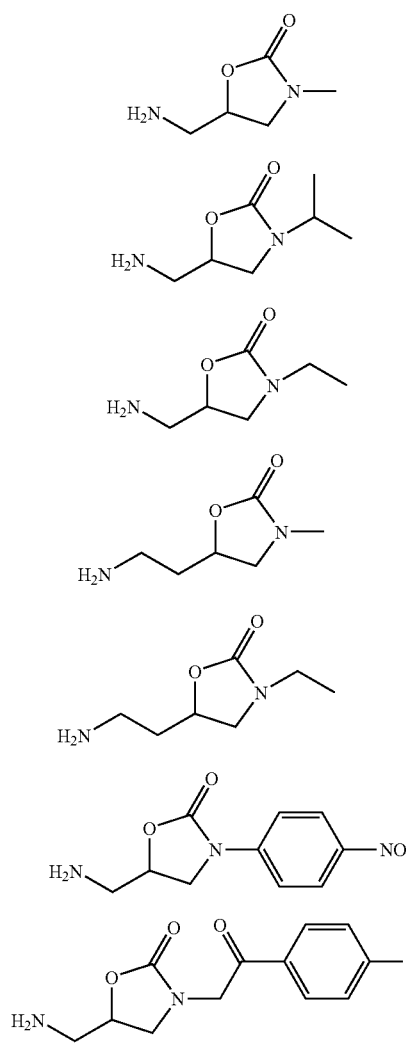

2. Library-Synthesis

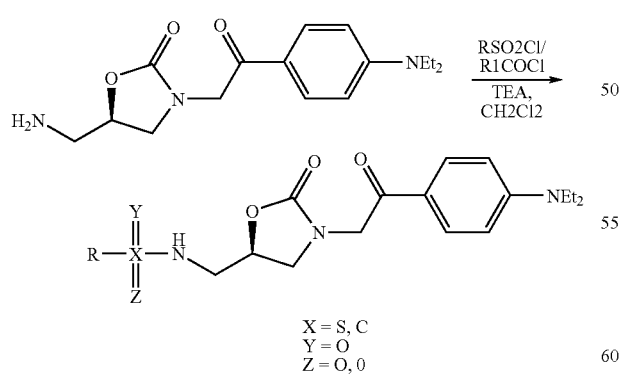

0.1 mM Solution of the oxazolidinone in CH$_2$Cl$_2$ (25 mL) was prepared. From the above std. soln. syringed out 1.0 mL each (0.10 mmol) into 3 mL capped vials. Added triethylamine, 28 μL/vial (0.2 mmol, 2.0 equiv). Added 1.0 mL (0.10 mmol) of the stock solution (0.10 mM) of acid/sulphonyl chlorides into respective vials. The vial capped, the solution mixed well and kept aside at RT (20 h). All compounds purified by prep. TLC. (EtOAc-hexane). Silica gel band containing the product was taken in CH$_3$CN (15.0 mL). Filtered and washed with more CH$_3$CN (3 mL), and solvent removed on rotovap. The product obtained was transferred to small vials using CH$_2$Cl$_2$, all samples air dried and finally dried in vacuo. All samples were analyzed by LCMS.

Other Amines used for the library:

G3(R), G5(R), G5 (S), G12(R), G9(R), G9(S), G13(S).

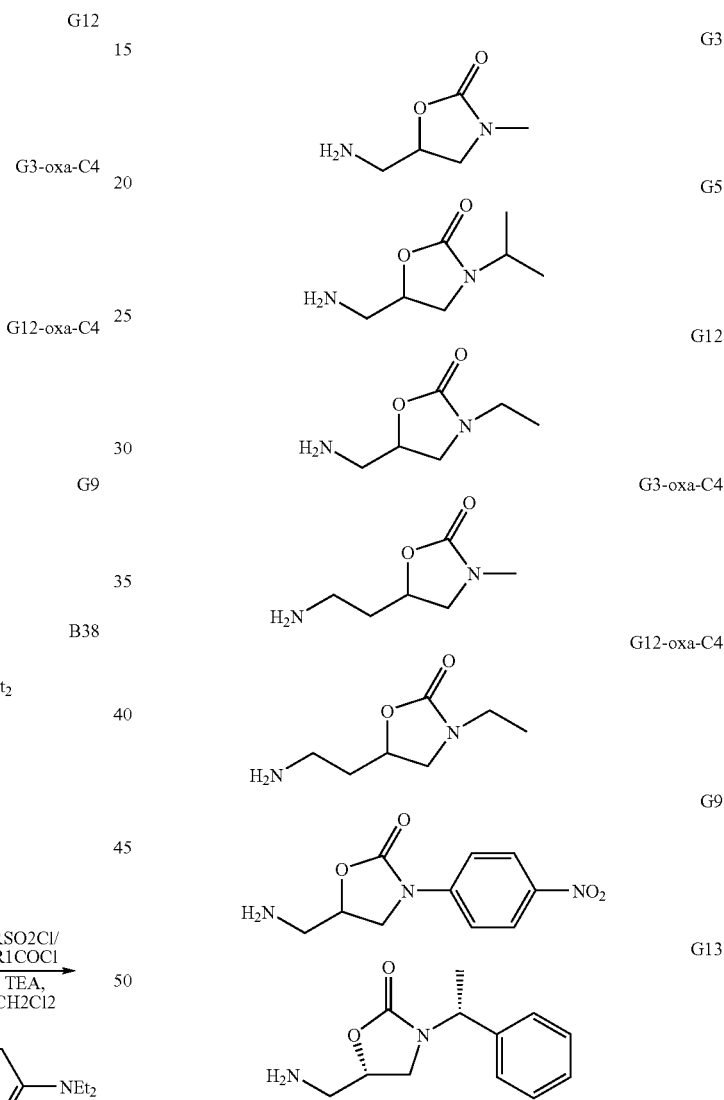

Sulphonyl/acid chlorides used:

B38: K1, K9, K10, K11, K21, K22, K23, K83, E112

G12-oxa-C4: K2, K93, K95, K96, K97, K99, K100, K101, K102, K117, E183, E184

G12: K2, K93, K95, K96, K97, K99, K100, K101, K102, K117, E183, E184

G9(R): E183, E184

G9(S): E183, E184

G5: K00, K0, K1, K2, K3, K4, K5, K8, K10, K11, K12, K21, K22, K23, K83, K90, K91, K92, K93, K94, K95, K96, K97, K98, K99, K100, K101, K102, K117, E183, E112, E184

G5(R): K2, K93, K95, K96, K97, K99, K100, K101, K102, K117, E183, E184

G3(R): K2, K93, K95, K96, K97, K100, K101, K102, K117, E183, E184

G13(R): K00, K0, K1, K2, K5, K9, K10, K11, K12, K21, K22, K23, K52, K60, K83, K90, K91, K92, K93, K94, K95, K96, K97, K98, K99, K100, K101, K102, E183,

B. Urea Type Compounds

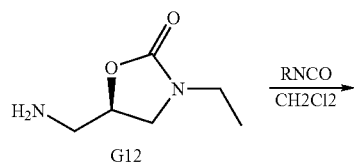

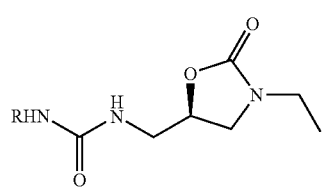

Oxazolidinone (0.1 mmol, 14 mg) in $CH_2Cl_2$ (1.0 mL) treated with the respective isocyante (0.1 mmol). In cases where the solution was not homogeneous 0.5 mL THF was also added. Reaction mixture kept at RT for 16 h and purified by prep. TLC (hexane-EtOAc). All products were analyzed by LCMS.

Other amines used for the library: G12(R), G12(S), G5(S), G9(R), G9(S),

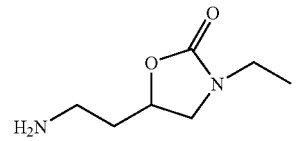

Isocyanates Used for the Library:

G12(R): DD2, DD3, DD4, DD5, DD6, DD7

G12: DD2, DD3, DD4, DD5, DD6, DD7

G5: DD2, DD3, DD4, DD5, DD6, DD7

G5(R): DD2, DD3, DD4, DD5, DD6, DD7

G12-oxa-C4: DD2, DD3, DD4, DD5, DD6, DD7

G9(R): DD2, DD3, DD4, DD5, DD6, DD7

G9(S): DD2, DD3, DD4, DD5, DD6, DD7

G3: DD2, DD3, DD4, DD5, DD6, DD7

C. Sulphenyl Compounds 0.1 mM solution of the oxazolidinone in $CH_2Cl_2$ (5 mL) was prepared. From the above std. soln. syringed out 1.0 mL each (0.10 mmol) into 3 mL capped vials. Added triethylamine, 28 µL/vial (0.2 mmol, 2.0 equiv). Added 1.0 mL (0.10 mmol) of the stock solution (0.10 mM) of sulphenyl chlorides into respective vials. The vial capped, the solution mixed well and kept aside at RT (20 h). All compounds purified by prep. TLC (EtOAc-hexane). Silica gel band containing the product was taken in $CH_3CN$ (15.0 mL). Filtered and washed with more $CH_3CN$ (3 mL), and solvent removed on rotovap. The product obtained was transferred to small vials using $CH_2Cl_2$, all samples air dried and finally dried in vacuo. All samples were analyzed by LCMS.

Amines used for the library: G5, G12, G9, G9(R), G12-oxa-C4

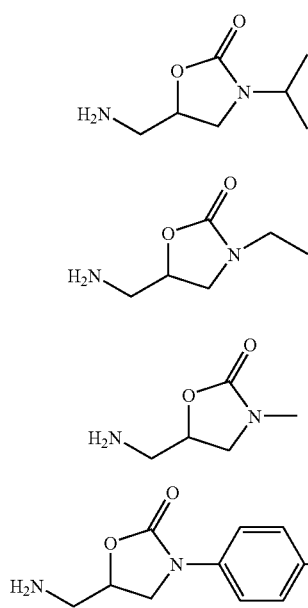

Oxazolidinones and sulphenyl chlorides used:

G5: BB3, BB5, BB7, BB9

G5(R): BB3, BB5, BB7, BB9

G12: BB3, BB5, BB7, BB9

G12(R): BB3, BB5, BB7, BB9

G9: BB3, BB5, BB7, BB9

G9(R): BB3, BB5, BB7, BB9

G12-oxa-C4: BB3, BB5, BB7, BB9

D. Substituted Aryl Amines-Buchwald Coupling

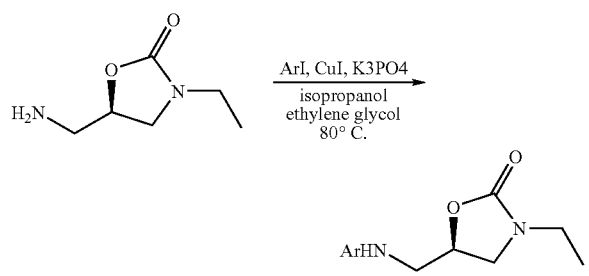

The reaction mixture containing the aminooxazolidinone (50 mg, 0.35 mmol), CuI (3.3 mg, 5 mol %), $K_3PO_4$ (148.6 mg, 0.70 mmol, 2 equiv), ethyleneglycol (43.4 mg, 0.70 mmol) and the aryl iodide (0.52 mmol, 1.5 equiv) in isopropanol (1.5 mL) was stirred at 70° C. for 24 h. Reaction mixture was cooled and filtered. Filtrate purified by prep. TLC. Products were analyzed by LCMS.

Other amines used for library: G5(R), G9(R), G9(S), G12 (R)

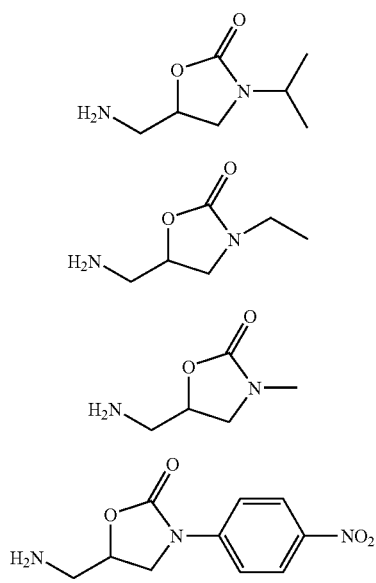

Oxazolidinones and Aryl Iodides Used:

G9(S): AA6, AA7, AA9, AA11, AA12 AA16, AA17, AA18, AA26, AA35

G9(R): AA6, AA7, AA9, AA16, AA17, AA18, AA26, AA35

G12(R): AA6, AA7, AA9, AA16, AA17, AA18, AA26, AA27, AA35

G12(S): AA6, AA7, AA9, AA16, AA17, AA18, AA26, AA35

G5(R): AA6, AA7, AA9, AA16, AA17, AA18, AA26, AA35

Ether Derivatives

5-Tosyloxymethyl-N-isopropyl-2-oxazolidinone

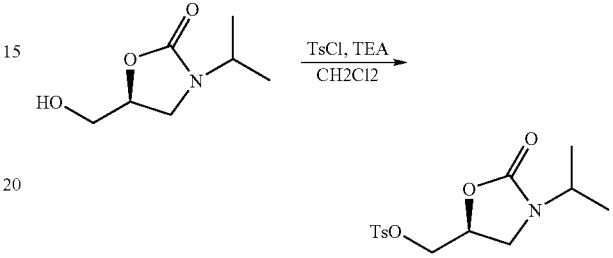

$CH_2Cl_2$ (25 mL) solution containing the oxazolidinone (2.3 g, 14.4 mmol, 1.0 equiv) was cooled in ice-bath. Added TEA (3.65 g, 36.1 mmol, 2.5 equiv) followed by TsCl (4.1 g, 21.5 mmol, 1.5 equiv) in small portions. Stirring continued at 0° C-RT (7 h). Diluted with more $CH_2Cl_2$ (50 mL), washed with 1N HCl (50 mL), water, brine, dried ($MgSO_4$) and concentrated to a brown liquid. Crude product passed through a silica gel column (60% EtOAc-hexane) to get the product as a colorless solid (4.3 g, 96%).

$^1$H NMR ($CDCl_3$, 200 MHz): δ 7.5 (ABq, 4H), 4.6 (m, 1H), 4.0 (m, 3H), 3.5 (t, 1H), 3.3 (dd, 1H), 2.39 (s, 3H), 1.2 (m, 6H). $^{13}$C NMR ($CDCl_3$, 50 MHz): δ 155.8, 145.2, 131.9, 129.9, 127.7, 69.5, 68.7, 44.7, 40.9, 21.4, 19.4, 19.3.

Library Synthesis

Method 1

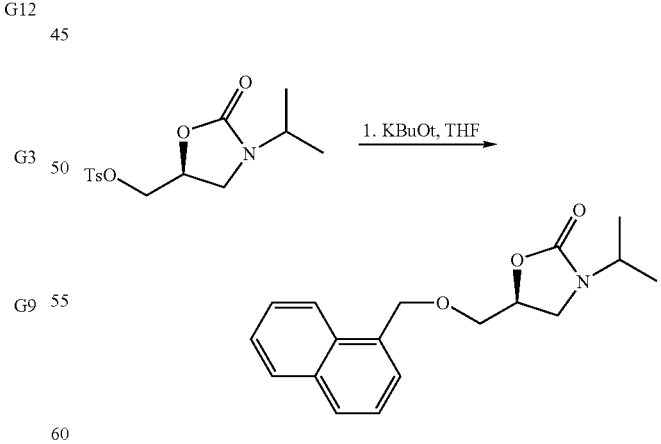

3.0 mL vial charged with 1-naphthol (12.7 mg, 0.09 mmol, 1.1 equiv) and THF (1.0 mL). Added KtBuO (13.4 mg, 0.12 mmol, 1.5 equiv). Stirred for 30 min. at RT. Added the tosylate (25 mg, 0.08 mmol, 1.0 equiv) in THF (1 mL). Stirred at RT for 2.0 h. Purified by prep. TLC (EtOAc-hexane) to get the pure product. Analyzed by LCMS.

Other Libraries Synthesized

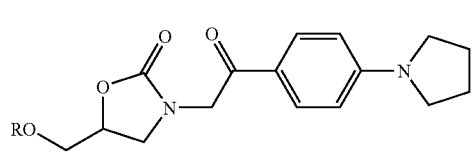
B39

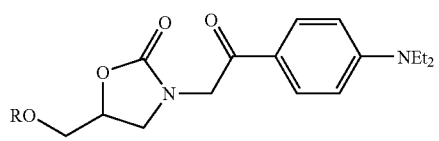
B38

Method 2

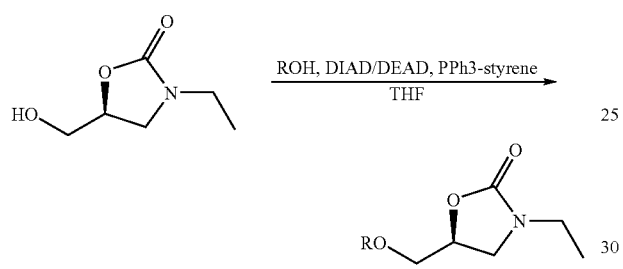

To a solution containing the oxazolidinone (14.4 mg, 0.1 mmol), PPh₃-polystyrene (120 mg, 1.2 equiv, loading 1.0 mmol/g), phenol (0.1 mmol, 1.0 equiv) and CH₂Cl₂ (1.0 mL). Added DIAD/DEAD (1.2 equiv) in THF (1.0 mL) slowly. Stirred gently for 24 h. The crude product was purified by prep. TLC (hexane-EtOAc).

Other libraries synthesized: G9, G5

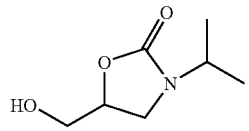
G5

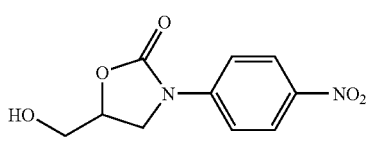
G9

Alcohols/phenols used:

B38: M1, M2, M3, M4, M5, M6, M14, M37, M38,

B39: M3, MS, M35, M38

G5: M39, M42, M43, M44, M45, M46, M47

G12(S): M1, M2, M3, M4, M5, M6, M11, M13, M14, M24, M30, M34, M35, M37, M38, M39, M40, M41, M42, M43, M44, M45, M46, M47

G12(R): M40, M41

G9(R): M1, M2, M3, M4, M5, M6, M11, M13, M14, M24, M30, M34, M35, M37, M38, M39, M40, M41,

Sulphonylchlorides (K):

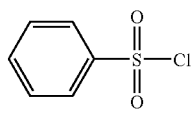
K0

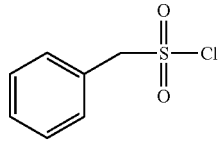
K00

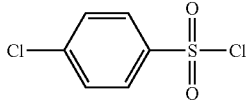
K1

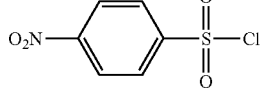
K2

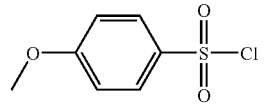
K3

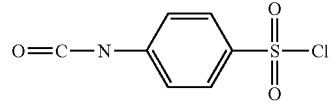
K4

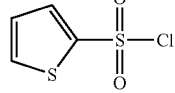
K5

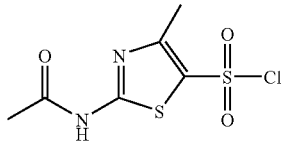
K6

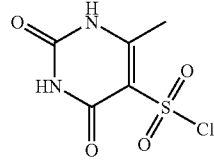
K7

K8

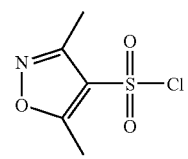
K9

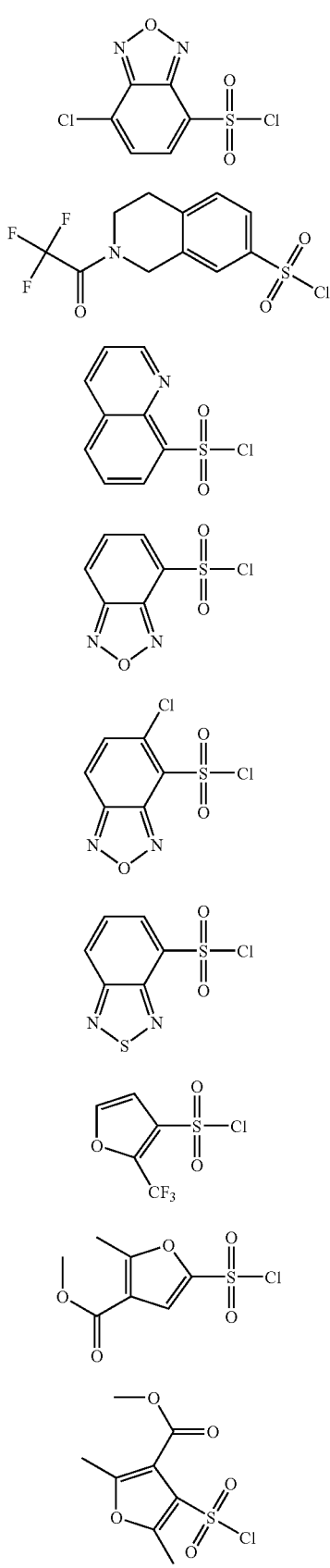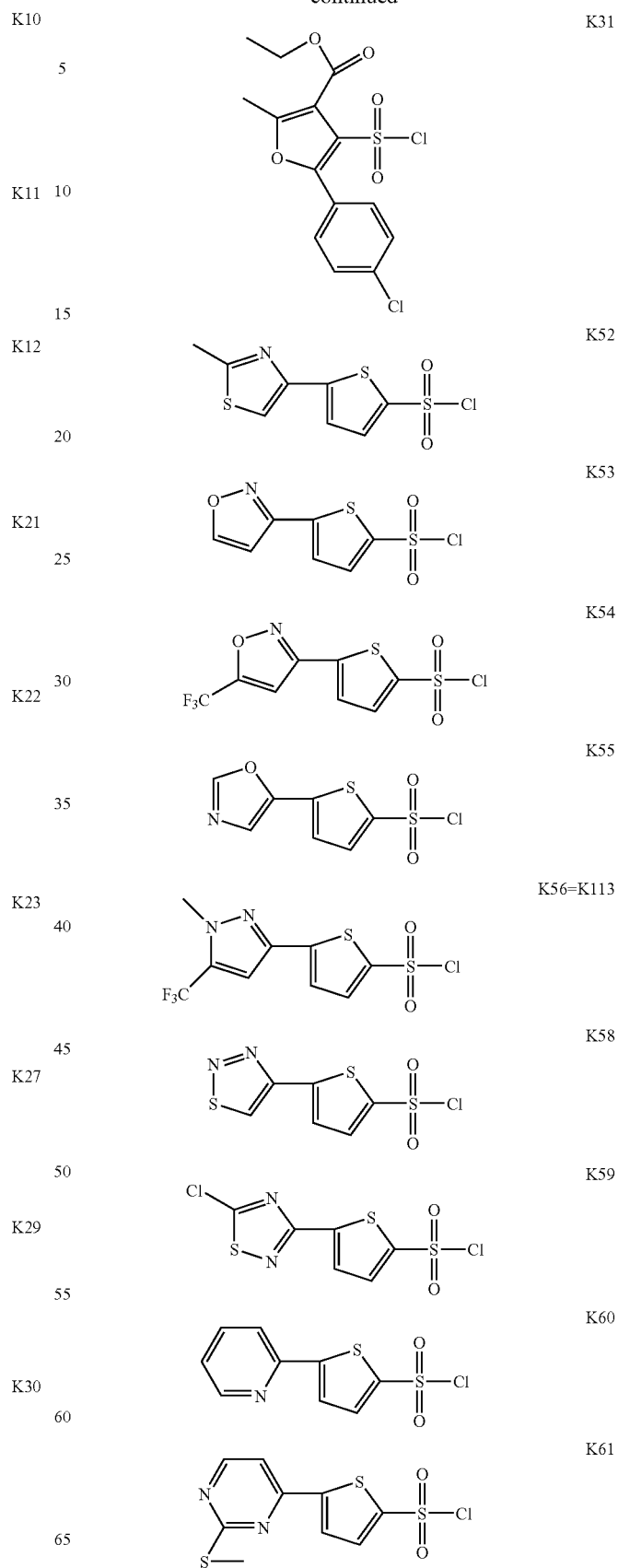

-continued

K66

K69

K70

K71

K72

K73

K76

K83

K90

K91

K92

-continued

K93

K94

K95

K96

K97

K98

K99

K100

K101

-continued
K102 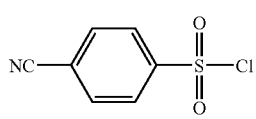
K103 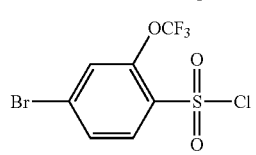
K104 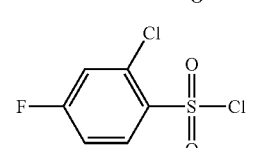
K105 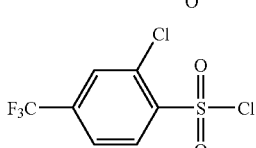
K106 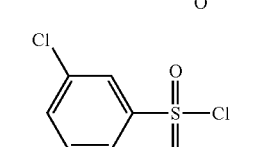
K107 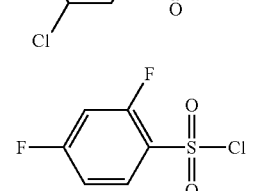
K108 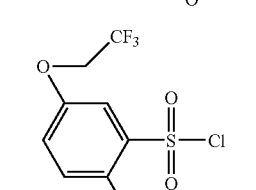
K109 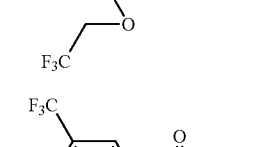
K110 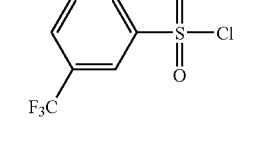
K111=K56 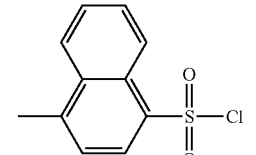
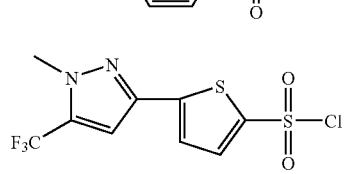
-continued
K112 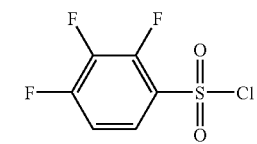
K113 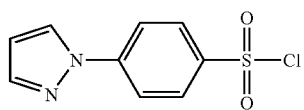
K114 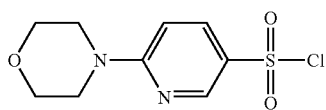
K115 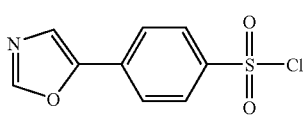
K116 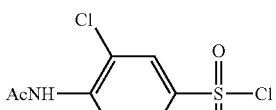
K117 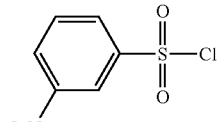
Acid Chlorides (E):
E0 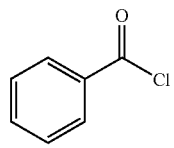
E00 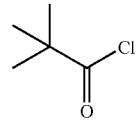
E1 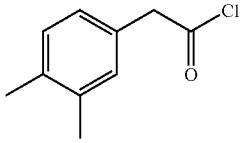
E2 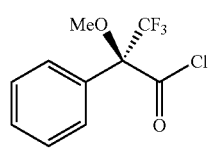

-continued
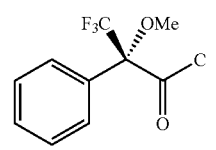
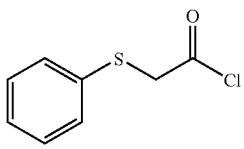
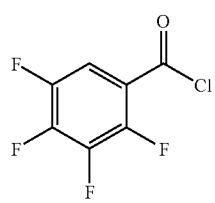
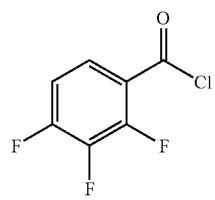
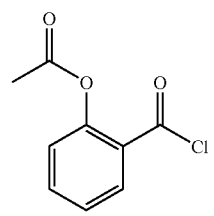
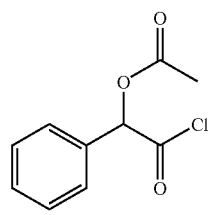
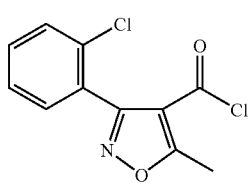
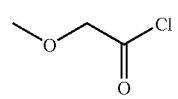
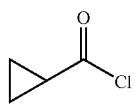
E3
E4
E5
E6
E7
E8
E9
E10
E11
-continued
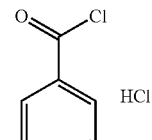
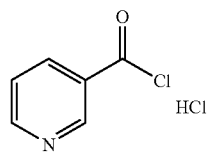
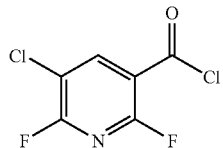
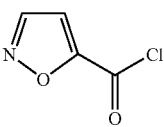
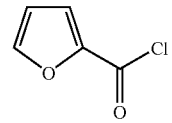
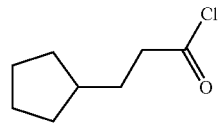
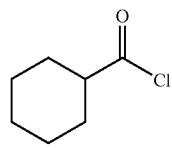
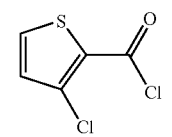
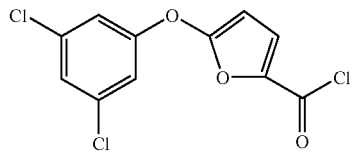
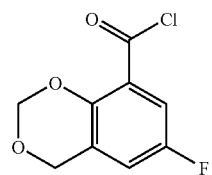
E12
E13
E14
E15
E16
E81
E82
E90
E107
E112

-continued
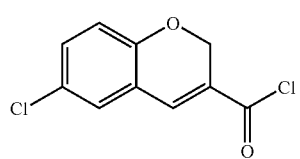
E113
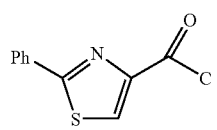
E117
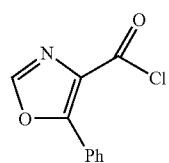
E120
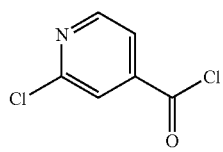
E124
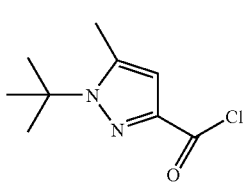
E136
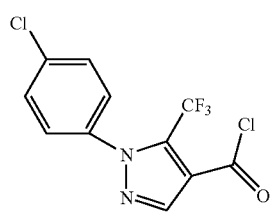
E154
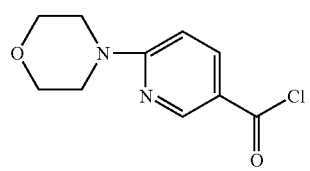
E157
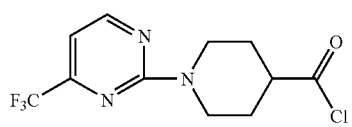
E159
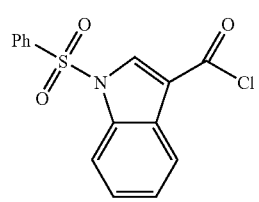
E164
-continued
E168
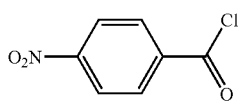
E183
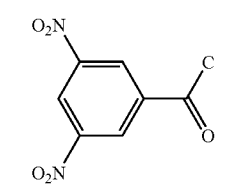
E184
Phenols (M):
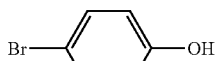
M1
M2
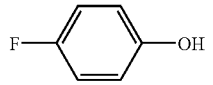
M3
M4
M5
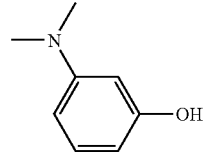
M6
M7
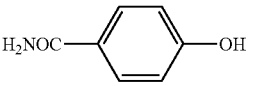
M8

-continued
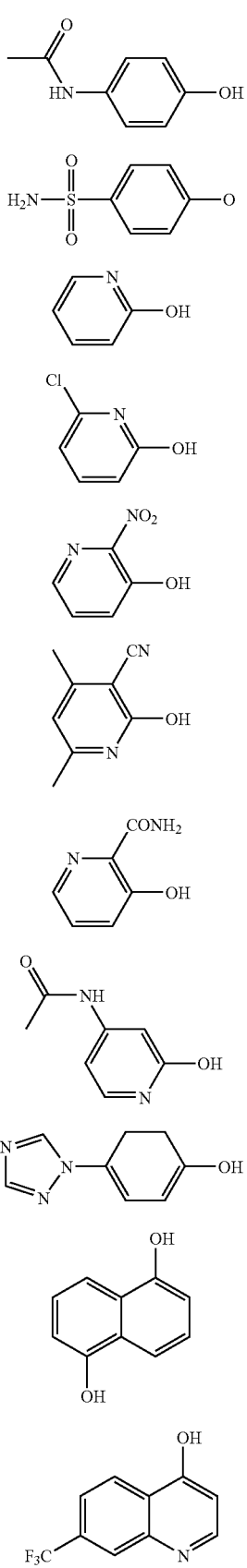
M9
M10
M11
M12
M13
M14
M15
M16
M24
M30
M34
-continued
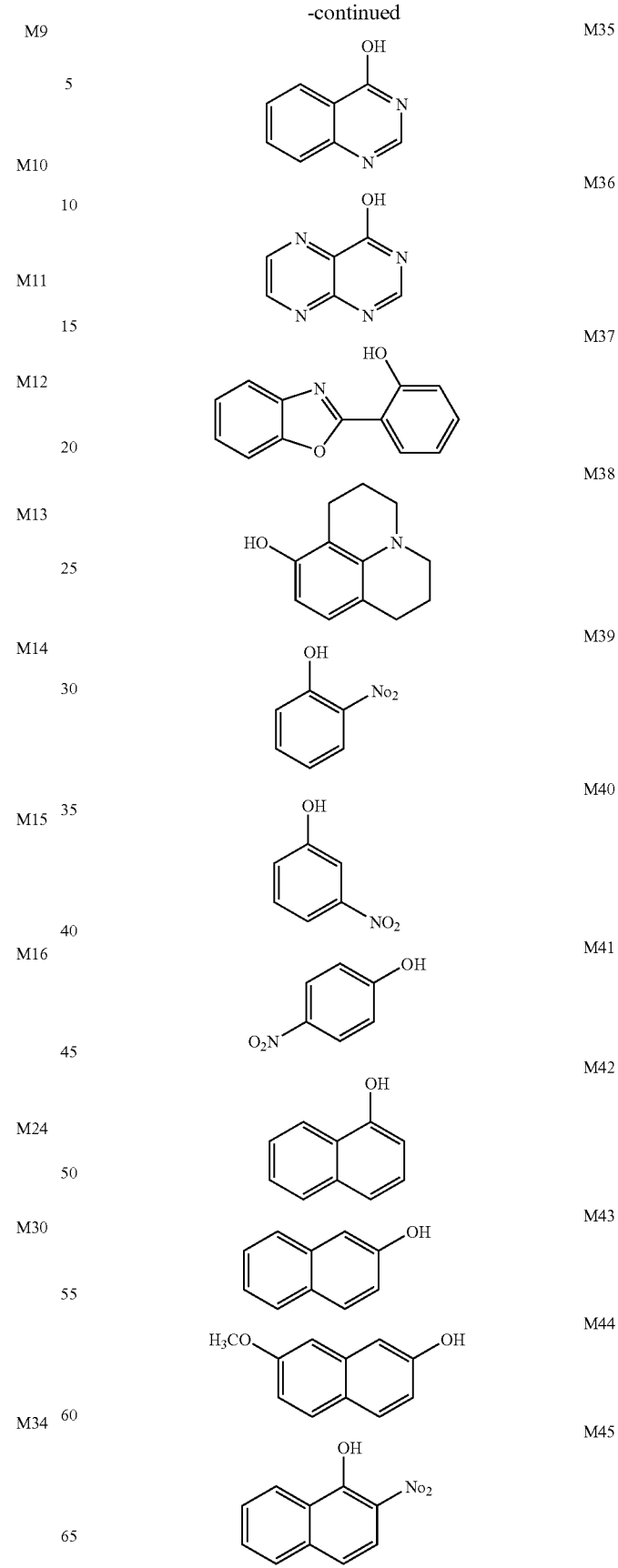
M35
M36
M37
M38
M39
M40
M41
M42
M43
M44
M45

-continued
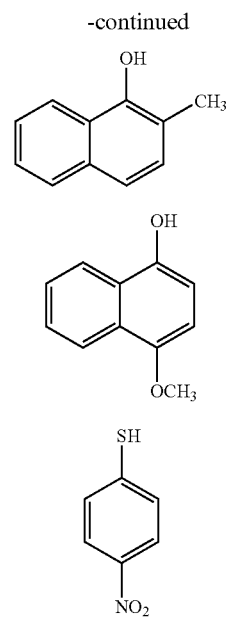
Aryl Iodides (AA):
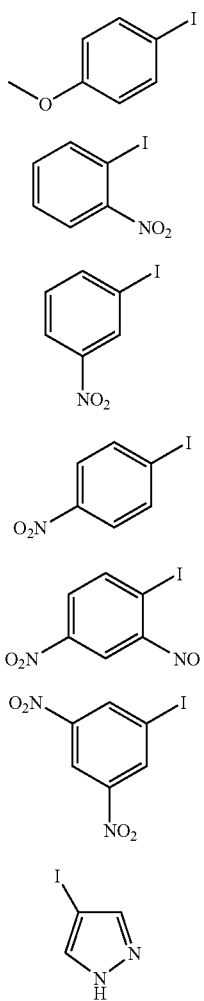
-continued
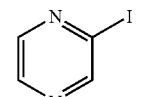
Sulphenyl Chlorides (BB), Isocyantes (DD)

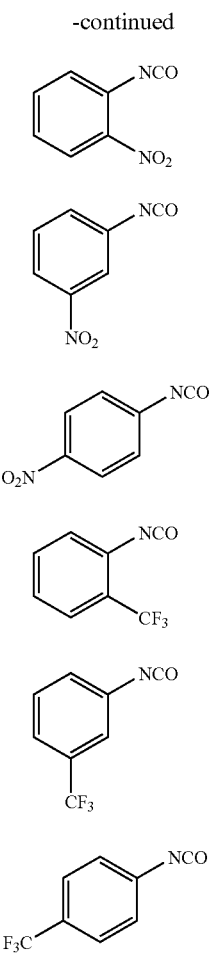

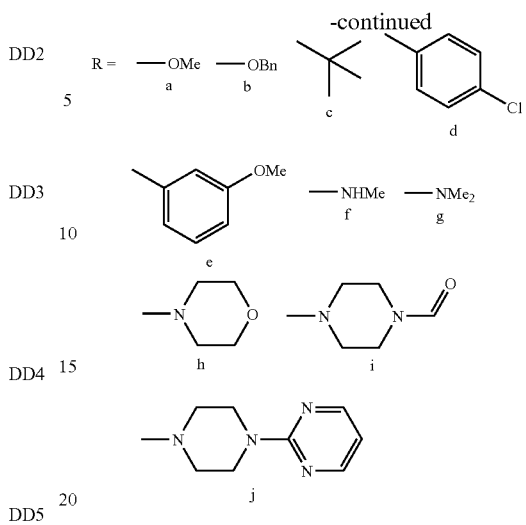

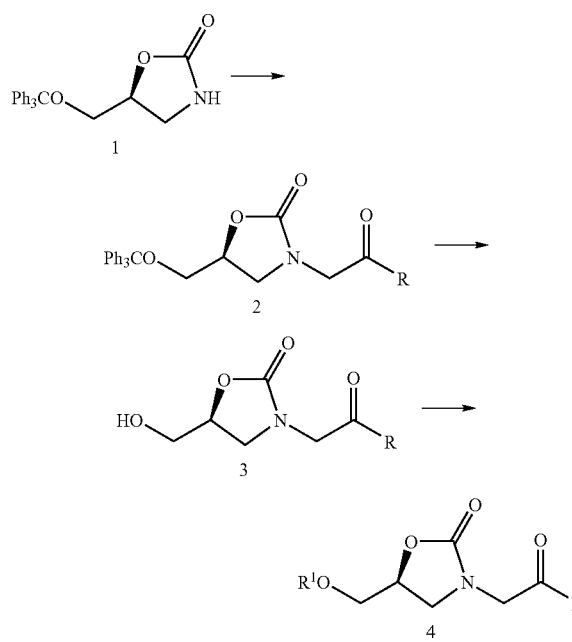

Scheme 1

Experimental

1. Preparation of the Precursors of Libraries.

General Methods. Column chromatography was performed on silica gel. TLC was performed on silica gel GF254. NMR spectra were recorded with an Varian VXR-200 NMR spectrometer $^1$H NMR and $^{13}$C NMR spectra were recorded at either 200 MHz or 50 MHz. LC-MS was carried out at PE-Sciex AP150EX single quadrapole instrument.

Typical Reactions for preparation of the alcohols (3):

Method A:

A solution of t-BuOK (50 mL, 50 mmol, 1 M) in THF was dropped into a solution of starting material 1 (18 g, 50 mmol) in dry THF (120 mL) under nitrogen at rt in 5 min. The mixture was stirred for 10 min at rt. Methyl bromoacetate (7.65 g, 50 mmol) was dropped into the flask in 5 min. The mixture was stirred for 1 h at rt. 10% NH$_4$Cl (20 mL) and hexanes (40 mL) were added, respectively. The organic phase is separated. The solvents were evaporated to give a crude product, without purification for next step. The crude product was dissolve into DCM (100 mL). Water (1.8 mL, 100 mmol) and TFA (8.55 g, 75 mmol) were added to the flask. The mixture was stirred for 2 h at rt. Removal of volatile materials gave a residue, which was co-evaporated with CH3CN (2×60 mL) to remove the trace water. Column chromatography purification (1:1 ethyl acetate/hexanes, then ethyl acetate) afforded a pure product (3a) (5.2 g, 55%). NMR: $\delta_H$ 3.4-4.1 (7H, m), 3.66 (3H, s), 4.5-4.7 (1H, m) ppm, $\delta_C$: 44.98, 46.10, 52.17, 62.61, 74.08, 158.20 (C=O), 168.92 (C=O, ester) ppm.

3b: yield: 36%, NMR: $\delta_H$ 2.9 (1H, br,s), 3.46-3.86 (4H, m), 4.02 (2H, s,), 4.54-4.70 (1H, m), 5.14 (2H, s), 7.2-7.3 (5H, m) ppm.

3e: yield: 8.1%. $\delta_H$ 2.5 (1H, br), 3.51-3.94 (4H, m), 3.79 (3H, s), 4.67 (2H, s), 4.5-4.7 (1H, m), 7.1-7.5 (4H, m) ppm.

Method B:

NaH (0.4 g, 10 mmol, 60%) was added in portions into a solution of starting material 1 (3.59 g, 10 mmol) in dry THF (40 mL) under nitrogen at rt in 10 min. The mixture was stirred for 1 h at rt. Bromopinacolone (1.79 g, 10 mL) was dropped into the flask in 10 min. The mixture was stirred overnight at rt. 10% NH$_4$Cl (10 mL) and hexanes (20 mL) were added, respectively. The organic phase is separated. The solvents were evaporated to give a crude product, without purification for next step. The crude product was dissolve into DCM (30 mL). Water (0.36 mL, 20 mmol) and TFA (1.71 g, 15 mmol) were added to the flask. The mixture was stirred for 1 h at rt. Removal of volatile materials gave a residue, which was co-evaporated with $CH_3CN$ (2×30 mL) to remove the trace water. Column chromatography purification (3:1 ethyl acetate/hexanes, then ethyl acetate) afforded a pure product (3c) (1.68 g, 78%). NMR: $\delta_H$ 1.14 (9H, s), 3.36-3.9 (6H, m), 4.18 (2H, s), 4.54-4.7 (1H, m) ppm, $\delta_C$: 26.08, 43.10, 46.30, 48.21, 63.11, 74.05, 158.45 (C=O), 209.60 (C=O, ketone) ppm.

3d: yield: 8.1%. $\delta_H$ 2.5 (1H, br), 3.56-3.9 (4H, m), 4.66 (2H, s), 4.5-4.7 (1H, m) 7.43, 7.47, 7.84, 7.88 (4H, AB) ppm.

Method C:

A solution of t-BuOK (10 mL, 10 mmol, 1 M) in THF was dropped into a solution of starting material 1 (3.59 g, 10 mmol) in dry THF (40 mL) under nitrogen at rt in 5 min. The mixture was stirred for 1 h at rt. A solution of methyl bromoacetamide (1.52 g, 10 mL) in THF was dropped into the flask in 10 min. The mixture was stirred overnight at rt. Con. $NH_4Cl$ (5 mL) and brine (5 mL) were added, respectively. The organic phase is separated. The solvents were evaporated to give a crude product. Flash column chromatography (hexanes/ethyl acetate 1:1) gave a pure product. To a solution of the pure material in DCM (30 mL) was added TFA (1.71 g, 15 mmol) and water (0.36 g). The mixture was stirred for 1 h at rt. Removal of volatile materials gave a residue, which was partitioned in water (50 mL) and t-BuOMe (20 mL). The separated aqueous layer was washed with t-BuOMe (20 mL). Water was evaporated to give a residue, which was co-evaporated with $CH_3CN$ (2×30 mL) to remove the trace water. A product (3f) (0.91 g, 48%) obtained, without further purification for next step.

3 g: yield: 99%. $\delta_H$ 2.91, 2.96 (6H, 2 s), 3.5-3.9 (4H, m), 3.92-4.16 (2H, AB), 4.41 (1H, br), 4.5-4.7 (1H, m) ppm.

3 h: yield: 74%. $\delta_H$ 3.25-3.61 (13H, m), 4.04 (2H, s), 4.5-4.7 (1H, m) ppm.

3i: yield: 99%.

3j: yield: 81%.

2. Preparation of Libraries:

A. Parallel Synthesis:

Typical reaction procedures (Reaction scales might be various accordingly):

Library 4-esters: To a solution of an acyl chloride (E) (0.1 mmol) in dry DCM (1 mL) were add a solution of 3 (0.1 mmol, 0.1 M) in DCM and triethyl amine (20.2 mg, 0.2 mmol). The mixture was standing overnight at rt. The reaction was completed. The product was purified with preparative TLC.

Library 4-sulfonates: To a solution of a sulfonyl chloride (K) (0.1 mmol) in dry DCM (1 mL) were add a solution of 3 (0.1 mmol, 0.1 M) in DCM and triethyl amine (20.2 mg, 0.2 mmol). The mixture was standing overnight at rt. The reaction was completed. The product was purified with preparative TLC.

Library 4-ethers: To a mixture of 3 (0.1 mmol), a phenol (M) (0.1 mmol) and $Ph_3P$-polystyrene (0.1 g, 0.1 mmol $Ph_3P$) in dry DCM (1 mL) was add a solution of DEAD (1 mL, 0.1 M). The mixture was standing at rt for three days. The reaction was completed. The product was purified with preparative TLC.

Libraries:

(1) 4a-Esters:

| Entry | MW | mMol |
|---|---|---|
| E0 | 140.57 | 0.1 |
| E1 | 182.65 | 0.1 |
| E2 | 252.62 | 0.1 |
| E3 | 252.62 | 0.1 |
| E4 | 186.66 | 0.1 |
| E5 | 212.53 | 0.1 |
| E6 | 194.54 | 0.1 |
| E7 | 198.60 | 0.1 |
| E8 | 212.63 | 0.1 |
| E9 | 256.08 | 0.1 |
| E12 | 178.02 | 0.1 |
| E13 | 178.02 | 0.1 |
| E14 | 211.98 | 0.1 |
| E15 | 131.52 | 0.1 |
| E16 | 130.53 | 0.1 |
| E17 | 130.53 | 0.1 |
| E37 | 274.08 | 0.1 |
| E40 | 154.60 | 0.1 |
| E49 | 190.63 | 0.1 |
| E55 | 175.03 | 0.1 |
| E90 | 181.04 | 0.1 |
| E92 | 215.48 | 0.1 |
| E99 | 216.73 | 0.1 |
| E113 | 229.06 | 0.1 |
| E117 | 223.68 | 0.1 |
| E120 | 207.61 | 0.1 |
| E124 | 176.00 | 0.1 |
| E136 | 200.67 | 0.1 |
| E154 | 309.07 | 0.1 |
| E157 | 226.66 | 0.1 |
| E159 | 293.67 | 0.1 |
| E164 | 319.76 | 0.1 |
| E168 | 192.60 | 0.1 |

(2) 4a-Sulfonates:

| Entry | MW | mMol |
|---|---|---|
| K0 | 190.65 | 0.1 |
| K00 | 190.65 | 0.1 |
| K1 | 211.07 | 0.1 |
| K2 | 221.62 | 0.1 |
| K3 | 206.65 | 0.1 |
| K5 | 182.65 | 0.1 |
| K6 | 254.71 | 0.1 |
| K8 | 290.65 | 0.1 |
| K9 | 195.62 | 0.1 |
| K10 | 253.06 | 0.1 |
| K11 | 327.71 | 0.1 |
| K12 | 227.67 | 0.1 |
| K16 | 438.33 | 0.1 |
| K17 | 180.62 | 0.1 |
| K21 | 218.62 | 0.1 |
| K23 | 234.69 | 0.1 |
| K29 | 238.65 | 0.1 |
| K30 | 252.67 | 0.1 |
| K31 | 363.21 | 0.1 |
| K52 | 279.79 | 0.1 |
| K53 | 249.70 | 0.1 |
| K54 | 317.69 | 0.1 |
| K55 | 249.70 | 0.1 |
| K56 | 330.74 | 0.1 |
| K59 | 301.12 | 0.1 |
| K60 | 259.74 | 0.1 |
| K61 | 306.82 | 0.1 |
| K66 | 237.66 | 0.1 |
| K70 | 256.71 | 0.1 |
| K76 | 262.72 | 0.1 |
| K83 | 234.69 | 0.1 |
| K90 | 194.61 | 0.1 |
| K91 | 255.52 | 0.1 |

-continued

| Entry | MW | mMol |
|---|---|---|
| K92 | 232.73 | 0.1 |
| K93 | 244.62 | 0.1 |
| K94 | 245.51 | 0.1 |
| K96 | 256.06 | 0.1 |
| K97 | 289.62 | 0.1 |
| K98 | 302.86 | 0.1 |
| K100 | 235.65 | 0.1 |
| K101 | 217.63 | 0.1 |
| K102 | 201.63 | 0.1 |
| K104 | 229.06 | 0.1 |
| K105 | 279.07 | 0.1 |
| K106 | 245.51 | 0.1 |
| K107 | 212.60 | 0.1 |
| K109 | 312.62 | 0.1 |
| K110 | 240.71 | 0.1 |
| K111 | 330.74 | 0.1 |
| K112 | 230.59 | 0.1 |
| K113 | 242.69 | 0.1 |
| K114 | 262.72 | 0.1 |
| K115 | 243.67 | 0.1 |

(3) 4a-Ethers:

| Materials | MW | mMol |
|---|---|---|
| M1 | 173 | 0.1 |
| M2 | 128.55 | 0.1 |
| M3 | 112.10 | 0.1 |
| M5 | 162.11 | 0.1 |
| M6 | 137.18 | 0.1 |
| M11 | 95.1 | 0.1 |
| M14 | 148.16 | 0.1 |
| M24 | 161.16 | 0.1 |
| M25 | 349.23 | 0.1 |
| M30 | 160.17 | 0.1 |
| M34 | 213.15 | 0.1 |
| M35 | 146.14 | 0.1 |
| M37 | 211.21 | 0.1 |
| M38 | 189.25 | 0.1 |

(4) 4b-Sulfonates:

| Entry | MW | mMol |
|---|---|---|
| K0 | 190.65 | 0.1 |
| K00 | 190.65 | 0.1 |
| K1 | 211.07 | 0.1 |
| K2 | 221.62 | 0.1 |
| K3 | 206.65 | 0.1 |
| K5 | 182.65 | 0.1 |
| K6 | 254.71 | 0.1 |
| K8 | 290.65 | 0.1 |
| K10 | 253.06 | 0.1 |
| K11 | 327.71 | 0.1 |
| K12 | 227.67 | 0.1 |
| K21 | 218.62 | 0.1 |
| K23 | 234.69 | 0.1 |
| K56 | 330.74 | 0.1 |
| K70 | 256.71 | 0.1 |
| K76 | 262.72 | 0.1 |
| K83 | 234.69 | 0.1 |
| K90 | 194.61 | 0.1 |
| K91 | 255.52 | 0.1 |
| K92 | 232.73 | 0.1 |
| K93 | 244.62 | 0.1 |
| K94 | 245.51 | 0.1 |
| K96 | 256.06 | 0.1 |
| K97 | 289.62 | 0.1 |
| K98 | 302.86 | 0.1 |
| K100 | 235.65 | 0.1 |

-continued

| Entry | MW | mMol |
|---|---|---|
| K101 | 221.62 | 0.1 |
| K102 | 201.63 | 0.1 |
| K104 | 229.06 | 0.1 |
| K105 | 279.07 | 0.1 |
| K106 | 245.51 | 0.1 |
| K107 | 212.60 | 0.1 |
| K109 | 312.62 | 0.1 |
| K110 | 240.71 | 0.1 |
| K111 | 330.74 | 0.1 |
| K112 | 230.59 | 0.1 |
| K113 | 242.69 | 0.1 |
| K114 | 262.72 | 0.1 |
| K115 | 243.67 | 0.1 |

(5) 4c-Esters:

| Entry | MW | mMol |
|---|---|---|
| E0 | 140.57 | 0.25 |
| E00 | 120.58 | 0.25 |
| E1 | 182.65 | 0.25 |
| E2 | 252.62 | 0.20 |
| E4 | 186.66 | 0.25 |
| E5 | 212.53 | 0.25 |
| E6 | 194.54 | 0.25 |
| E7 | 198.60 | 0.25 |
| E8 | 212.63 | 0.25 |
| E10 | 108.52 | 0.25 |
| E11 | 104.53 | 0.25 |
| E12 | 178.02 | 0.25 |
| E13 | 178.02 | 0.25 |
| E14 | 211.98 | 0.25 |
| E15 | 131.52 | 0.25 |
| E16 | 130.53 | 0.25 |

(6) 4c-sulfonates:

| Entry | MW | mMol |
|---|---|---|
| K0 | 190.65 | 0.15 |
| K00 | 190.65 | 0.15 |
| K1 | 211.07 | 0.15 |
| K2 | 221.62 | 0.15 |
| K3 | 206.65 | 0.15 |
| K4 | 217.63 | 0.15 |
| K5 | 182.65 | 0.15 |
| K6 | 254.72 | 0.15 |
| K8 | 290.65 | 0.15 |
| K9 | 195.62 | 0.15 |
| K10 | 253.06 | 0.15 |
| K11 | 327.71 | 0.15 |
| K12 | 227.67 | 0.15 |

(7) 4d-esters:

| Entry | MW | mMol |
|---|---|---|
| E7 | 198.60 | 0.09 |
| E10 | 108.52 | 0.09 |
| E11 | 104.53 | 0.09 |
| E15 | 131.52 | 0.09 |

(8) 4d-sulfonates:

| Entry | MW | mMol |
|---|---|---|
| K5 | 182.65 | 0.09 |
| K8 | 290.65 | 0.09 |
| K10 | 253.06 | 0.09 |
| K11 | 327.71 | 0.09 |

(9) 4e-esters:

| Entry | MW | mMol |
|---|---|---|
| E0 | 140.57 | 0.075 |
| E1 | 182.65 | 0.075 |
| E4 | 186.66 | 0.075 |
| E8 | 212.63 | 0.075 |
| E7 | 198.60 | 0.075 |
| E10 | 108.52 | 0.075 |
| E11 | 104.53 | 0.075 |
| E15 | 131.52 | 0.075 |
| E16 | 130.53 | 0.075 |

(10) 4e-sulfonates:

| Entry | MW | mMol |
|---|---|---|
| K0 | 190.65 | 0.075 |
| K00 | 190.65 | 0.075 |
| K1 | 211.07 | 0.075 |
| K2 | 221.62 | 0.075 |
| K3 | 206.65 | 0.075 |
| K4 | 217.63 | 0.075 |
| K5 | 182.65 | 0.075 |
| K6 | 254.72 | 0.075 |
| K8 | 290.65 | 0.075 |
| K9 | 195.62 | 0.075 |
| K10 | 253.06 | 0.075 |
| K11 | 327.71 | 0.075 |
| K12 | 227.67 | 0.075 |

(11) 4f-esters:

| Entry | MW | Wt/V | mMol |
|---|---|---|---|
| E183 | 185.56 | | 0.1 |
| E184 | 230.56 | | 0.1 |

(12) 4f-sulfonates:

| Entry | MW | Wt/V | mMol |
|---|---|---|---|
| K2 | 221.62 | | 0.1 |
| K96 | 256.06 | | 0.1 |
| K101 | 221.62 | | 0.1 |
| K106 | 245.51 | | 0.1 |
| K117 | 221.62 | | 0.1 |

(13) 4 g-sulfonates:

| Entry | MW | Wt/V | mMol |
|---|---|---|---|
| K0 | 190.65 | | 0.1 |
| K00 | 190.65 | | 0.1 |
| K1 | 211.07 | | 0.1 |
| K2 | 221.62 | | 0.1 |
| K4 | 217.63 | | 0.1 |
| K5 | 182.65 | | 0.1 |
| K6 | 254.71 | | 0.1 |
| K8 | 290.65 | | 0.1 |
| K10 | 253.06 | | 0.1 |
| K11 | 327.71 | | 0.1 |
| K12 | 227.67 | | 0.1 |
| K19 | 229.09 | | 0.1 |
| K21 | 218.62 | | 0.1 |
| K22 | 253.07 | | 0.1 |
| K23 | 234.69 | | 0.1 |
| K30 | 252.67 | | 0.1 |
| K52 | 279.79 | | 0.1 |
| K54 | 317.69 | | 0.1 |
| K55 | 249.70 | | 0.1 |
| K56 | 330.74 | | 0.1 |
| K59 | 301.12 | | 0.1 |
| K60 | 259.74 | | 0.1 |
| K66 | 237.66 | | 0.1 |
| K69 | 181.60 | | 0.1 |
| K70 | 256.71 | | 0.1 |
| K76 | 262.72 | | 0.1 |
| K83 | 234.69 | | 0.1 |
| K90 | 194.61 | | 0.1 |
| K91 | 255.52 | | 0.1 |
| K92 | 232.73 | | 0.1 |
| K93 | 244.62 | | 0.1 |
| K94 | 245.51 | | 0.1 |
| K95 | 266.62 | | 0.1 |
| K96 | 256.06 | | 0.1 |
| K97 | 289.62 | | 0.1 |
| K98 | 302.86 | | 0.1 |
| K99 | 266.57 | | 0.1 |
| K100 | 235.65 | | 0.1 |
| K101 | 217.63 | | 0.1 |
| K104 | 229.06 | | 0.1 |
| K105 | 279.07 | | 0.1 |
| K106 | 245.51 | | 0.1 |
| K107 | 212.60 | | 0.1 |
| K109 | 312.62 | | 0.1 |
| K110 | 240.71 | | 0.1 |
| K111 | 330.74 | | 0.1 |
| K112 | 230.59 | | 0.1 |
| K113 | 242.69 | | 0.1 |
| K115 | 243.67 | | 0.1 |

(14) 4 h-esters:

| Entry | MW | mMol |
|---|---|---|
| E0 | 140.57 | 0.1 |
| E1 | 182.65 | 0.1 |
| E2 | 252.62 | 0.1 |
| E3 | 252.62 | 0.1 |
| E4 | 186.66 | 0.1 |
| E5 | 212.53 | 0.1 |
| E6 | 194.54 | 0.1 |
| E7 | 198.60 | 0.1 |
| E8 | 212.63 | 0.1 |
| E9 | 256.08 | 0.1 |
| E12 | 178.02 | 0.1 |
| E13 | 178.02 | 0.1 |
| E14 | 211.98 | 0.1 |
| E15 | 131.52 | 0.1 |
| E16 | 130.53 | 0.1 |
| E17 | 130.53 | 0.1 |
| E37 | 274.08 | 0.1 |
| E40 | 154.60 | 0.1 |

-continued

| Entry | MW | mMol |
|---|---|---|
| E49 | 190.63 | 0.1 |
| E55 | 175.03 | 0.1 |
| E90 | 181.04 | 0.1 |
| E92 | 215.48 | 0.1 |
| E99 | 216.73 | 0.1 |
| E113 | 229.06 | 0.1 |
| E117 | 223.68 | 0.1 |
| E120 | 207.61 | 0.1 |
| E124 | 176.00 | 0.1 |
| E136 | 200.67 | 0.1 |
| E154 | 309.07 | 0.1 |
| E157 | 226.66 | 0.1 |
| E159 | 293.67 | 0.1 |
| E164 | 319.76 | 0.1 |
| E168 | 192.60 | 0.1 |

(15) 4 h-sulfonates:

| Entry | MW | Wt/V | mMol |
|---|---|---|---|
| K0 | 190.65 | | 0.1 |
| K00 | 190.65 | | 0.1 |
| K1 | 211.07 | | 0.1 |
| K2 | 221.62 | | 0.1 |
| K3 | 206.65 | | 0.1 |
| K4 | 217.63 | | 0.1 |
| K5 | 182.65 | | 0.1 |
| K6 | 254.71 | | 0.1 |
| K8 | 290.65 | | 0.1 |
| K9 | 195.62 | | 0.1 |
| K10 | 253.06 | | 0.1 |
| K11 | 327.71 | | 0.1 |
| K12 | 227.67 | | 0.1 |
| K19 | 229.09 | | 0.1 |
| K21 | 218.62 | | 0.1 |
| K23 | 234.69 | | 0.1 |
| K27 | 247.95 | | 0.1 |
| K30 | 252.67 | | 0.1 |
| K52 | 279.79 | | 0.1 |
| K53 | 249.70 | | 0.1 |
| K54 | 317.69 | | 0.1 |
| K55 | 249.70 | | 0.1 |
| K56 | 330.74 | | 0.1 |
| K59 | 301.12 | | 0.1 |
| K60 | 259.74 | | 0.1 |
| K61 | 306.82 | | 0.1 |
| K66 | 237.66 | | 0.1 |
| K69 | 181.60 | | 0.1 |
| K70 | 256.71 | | 0.1 |
| K76 | 262.72 | | 0.1 |
| K83 | 234.69 | | 0.1 |

(16) 4 h-Ethers:

| Materials | MW | Wt/V | mMol |
|---|---|---|---|
| M1 | 173 | | 0.1 |
| M2 | 128.55 | | 0.1 |
| M3 | 112.10 | | 0.1 |
| M5 | 162.11 | | 0.1 |
| M6 | 137.18 | | 0.1 |
| M14 | 148.16 | | 0.1 |
| M24 | 161.16 | | 0.1 |
| M34 | 213.15 | | 0.1 |
| M35 | 146.14 | | 0.1 |

(17) 4l-Sulfonates:

| Entry | MW | Wt/V | mMol |
|---|---|---|---|
| K0 | 190.65 | | 0.1 |
| K00 | 190.65 | | 0.1 |
| K1 | 211.07 | | 0.1 |
| K2 | 221.62 | | 0.1 |
| K3 | 206.65 | | 0.1 |
| K5 | 182.65 | | 0.1 |
| K6 | 254.71 | | 0.1 |
| K8 | 290.65 | | 0.1 |
| K10 | 253.06 | | 0.1 |
| K11 | 327.71 | | 0.1 |
| K12 | 227.67 | | 0.1 |
| K16 | 438.33 | | 0.1 |
| K19 | 229.09 | | 0.1 |
| K21 | 218.62 | | 0.1 |
| K22 | 253.07 | | 0.1 |
| K23 | 234.69 | | 0.1 |
| K52 | 279.79 | | 0.1 |
| K60 | 259.74 | | 0.1 |
| K70 | 256.71 | | 0.1 |
| K76 | 262.72 | | 0.1 |
| K83 | 234.69 | | 0.1 |
| K90 | 194.61 | | 0.1 |
| K91 | 255.52 | | 0.1 |
| K92 | 232.73 | | 0.1 |
| K93 | 244.62 | | 0.1 |
| K94 | 245.51 | | 0.1 |
| K96 | 256.06 | | 0.1 |
| K97 | 289.62 | | 0.1 |
| K98 | 302.86 | | 0.1 |
| K100 | 235.65 | | 0.1 |
| K101 | 221.62 | | 0.1 |
| K102 | 201.63 | | 0.1 |
| K104 | 229.06 | | 0.1 |
| K105 | 279.07 | | 0.1 |
| K106 | 245.51 | | 0.1 |
| K107 | 212.60 | | 0.1 |
| K109 | 312.62 | | 0.1 |
| K110 | 240.71 | | 0.1 |
| K111 | 330.74 | | 0.1 |
| K112 | 230.59 | | 0.1 |
| K113 | 242.69 | | 0.1 |
| K115 | 243.67 | | 0.1 |

(18) 4j-Sulfonates:

| Entry | MW | Wt/V | mMol |
|---|---|---|---|
| K0 | 190.65 | | 0.1 |
| K1 | 211.07 | | 0.1 |
| K2 | 221.62 | | 0.1 |
| K3 | 206.65 | | 0.1 |
| K8 | 290.65 | | 0.1 |
| K21 | 218.62 | | 0.1 |
| K60 | 259.74 | | 0.1 |
| K70 | 256.71 | | 0.1 |
| K83 | 234.69 | | 0.1 |
| K90 | 194.61 | | 0.1 |
| K91 | 255.52 | | 0.1 |
| K93 | 244.62 | | 0.1 |
| K94 | 245.51 | | 0.1 |
| K97 | 289.62 | | 0.1 |
| K98 | 302.86 | | 0.1 |
| K100 | 235.65 | | 0.1 |
| K101 | 221.62 | | 0.1 |
| K102 | 201.63 | | 0.1 |

B. Combinatorial Synthesis.

Procedure: To a solution of 3c (4.0 mmol), DMAP (9.8 mg, 0.08 mmol), pyridine (576.8 mg. 8.0 mmol) in $CH_2Cl_2$ (15 mL) was drop a solution of the acyl chlorides in $CH_2Cl_2$ (5 mL) into the flask in 5 min. The mixture was stirred at rt. for 24 h, washed with 1 N NaHCO$_3$ and dried over Na$_2$SO$_4$. Removal of the solvents gave a crude product (1.35 g). The products were separated with HPLC (4.6×25 cm, C-18 Column; flow rate: 1.0 mL/min; 0 min: H$_2$O(70), CH$_3$CN(12), CH$_3$OH (18); 20 min: H$_2$O(50), CH$_3$CN(20), CH$_3$OH (30); 22 min: H$_2$O(50), CH$_3$CN(O), CH$_3$OH (50); 55 min: H$_2$O (17), CH$_3$CN(O), CH$_3$OH (83); post run; 10 min).

(19) 4c-esters:

| Entry | MW | mMol |
|---|---|---|
| E0 | 140.57 | 0.25 mmol |
| E00 | 120.58 | 0.25 mmol |
| E1 | 182.65 | 0.25 mmol |
| E2 | 252.62 | 0.25 mmol |
| E4 | 186.66 | 0.25 mmol |
| E5 | 212.53 | 0.25 mmol |
| E6 | 194.54 | 0.25 mmol |
| E7 | 198.60 | 0.25 mmol |
| E8 | 212.63 | 0.25 mmol |
| E10 | 108.52 | 0.25 mmol |
| E11 | 104.53 | 0.25 mmol |
| E12 | 178.02 | 0.25 mmol |
| E13 | 178.02 | 0.25 mmol |
| E14 | 211.98 | 0.25 mmol |
| E15 | 131.52 | 0.25 mmol |
| E16 | 130.53 | 0.25 mmol |

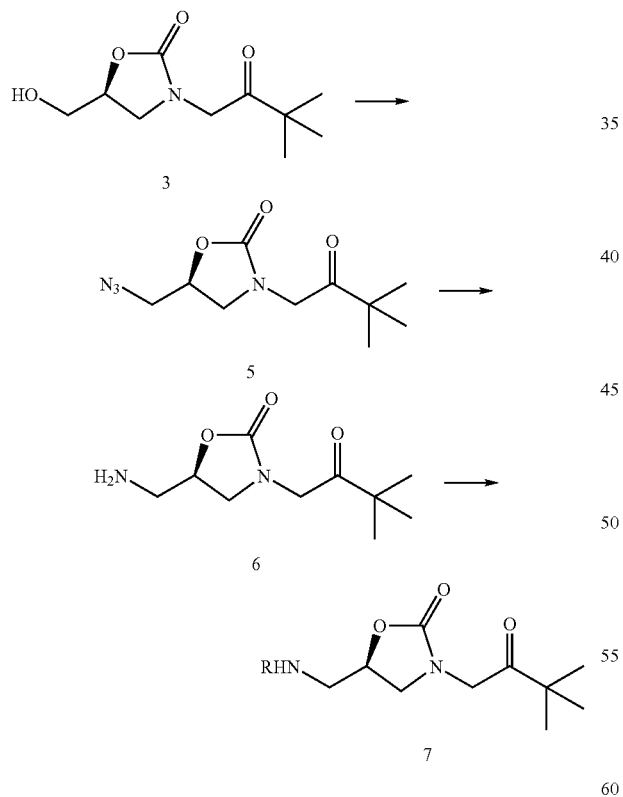

Scheme 2

1. Preparation of Precursors of Libraries:

Azide 5: To a solution of 3c (0.52 g, 2.4 mmol) and Ph$_3$P (0.79 g, 3.0 mmol) in THF was dropped DEAD (0.56 g, 3.2 mmol) and DPPA (0.83 g, 3.0 mmol) at 0° C., respectively. The mixture was allowed to warm to rt. The mixture was stirred at rt for 2 h. Removal of volatile materials gave a residue, which was purified by column chromatography to afford a pure product (5) (0.5 g, 87%).

Amine 6: To a solution of 5 (0.48 g, 2.0 mmol) in THF was added Ph$_3$P (0.63 g, 2.4 mmol) at rt. The mixture was stirred at rt overnight. Removal of volatile materials gave a residue. 90% MeOH (20 mL) was added to the flask. The solution was stirred at rt for 2 h. Removal of the solvents gave a residue, which was purified by column chromatography to afford a pure product (6) (0.2 g, 47%). $\delta_H$ 1.17 (9H, s), 1.41 (2H, br), 2.8-3.2 (2H, m), 3.2-3.6 (2H, m), 4.07, 4.16, 4.22, 4.31 (2H, AB), 4.48-4.64 (1H, m) ppm.

2. Preparation of Libraries (Parallel Synthesis):

Procedure: To a solution of a sulfonyl chloride (K) (0.1 mmol) in dry DCM (1 mL) were add a solution of 6 (0.1 mmol, 0.1 M) in DCM and triethyl amine (20.2 mg, 0.2 mmol). The mixture was standing at rt for 6 h. The reaction was completed. The product was purified with preparative TLC.

(20) Library 7-Sulfonamides:

| Entry | Materials MW | Wt/V | mMol |
|---|---|---|---|
| K2 | 221.62 | mg | 0.1 |
| K4 | 217.63 | mg | 0.1 |
| K5 | 182.65 | mg | 0.1 |
| K8 | 290.65 | mg | 0.1 |
| K9 | 195.62 | mg | 0.1 |
| K10 | 253.06 | mg | 0.1 |
| K11 | 327.71 | mg | 0.1 |
| K12 | 227.67 | mg | 0.1 |
| K21 | 218.62 | mg | 0.1 |
| K22 | 253.06 | mg | 0.1 |
| K23 | 234.68 | mg | 0.1 |
| K83 | 234.68 | mg | 0.1 |

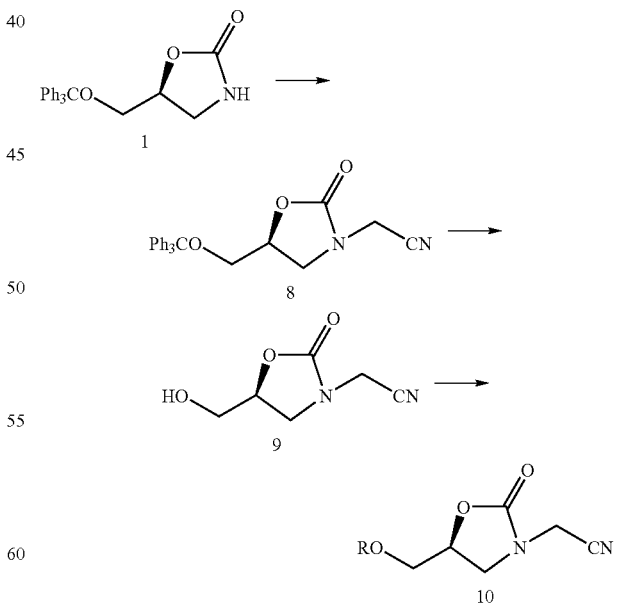

Scheme 3

1. Preparation of precursors of libraries:

Alcohol 9: A solution of t-BuOK (10 mL, 10 mmol, 1 M) in THF was dropped into a solution of starting material 1 (3.59 g, 10 mmol) in dry THF (40 mL) under nitrogen at rt in 5 min. The mixture was stirred for 10 min at rt. Bromoacetonitrile (1.2 g, 10 mmol) was dropped into the flask in 5 min. The mixture was stirred for 1 h at rt. 10% NH$_4$Cl (20 mL) and hexanes (40 mL) were added, respectively. The organic phase is separated. The solvents were evaporated to give a crude product, without purification for next step. The crude product was dissolve into DCM (30 mL). Water (0.36 mL, 20 mmol) and TFA (1.71 g, 15 mmol) were added to the flask. The mixture was stirred for 2 h at rt. Removal of volatile materials gave a residue, which was co-evaporated with CH$_3$CN (2×30 mL) to remove the trace water. Column chromatography purification (1:1 ethyl acetate/hexanes, then ethyl acetate) afforded a pure product (9) (0.59 g, 38%). $\delta_H$ 2.49 (1H, br), 3.35-3.66 (4H, m), 4.36 (1H, s), 4.5-4.7 (1H, m) ppm.

2. Preparation of Libraries (Parallel Synthesis):

Procedure: (1) Esters: To a solution of an acyl chloride (E) (0.1 mmol) in dry DCM (1 mL) were add a solution of 9 (0.1 mmol, 0.1 M) in N-methylmorpholine and triethyl amine (20.2 mg, 0.2 mmol). The mixture was standing overnight at rt. The reaction was completed. The product was purified with preparative TLC.

(21) Library 10-Esters:

| Entry | MW | Wt/V | mMol |
|-------|--------|------|------|
| E183  | 185.56 |      | 0.1  |
| E184  | 230.56 |      | 0.1  |

(2) Sulfonates: To a solution of a sulfonyl chloride (K) (0.1 mmol) in dry DCM (1 mL) were add a solution of 9 (0.1 mmol, 0.1 M) in N-methylmorpholine and triethyl amine (20.2 mg, 0.2 mmol). The mixture was standing at rt for 6 h. The reaction was completed.

The product was purified with preparative TLC.

(22) Library 10-Sulfonates:

| Entry | MW | Wt/V | mMol |
|-------|--------|------|------|
| K2    | 221.62 |      | 0.1  |
| K96   | 256.06 |      | 0.1  |
| K101  | 221.62 |      | 0.1  |
| K106  | 245.51 |      | 0.1  |
| K117  | 221.62 |      | 0.1  |

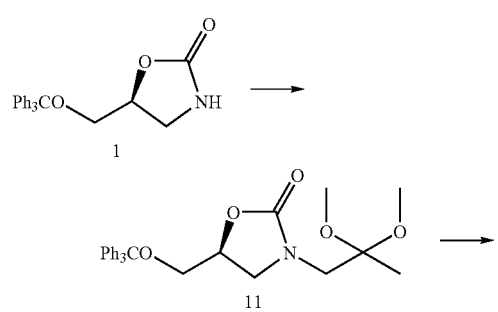

Scheme 4

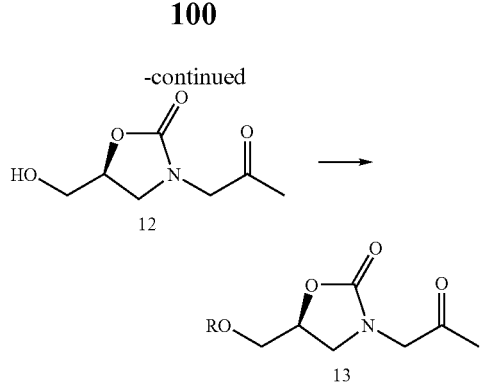

1. Preparation of Precursors of Libraries:

Compound 11: NaH (0.44 g, 11 mmol, 60%) was added in portions into a solution of starting material 1 (3.59 g, 10 mmol) in dry HMPA (30 mL) under nitrogen at rt in 10 min. The mixture was stirred for 1 h at rt. (MeO)$_2$CCH$_3$CH$_2$Br (1.83 g, 10 mL) was dropped into the flask in 10 min. The mixture was stirred overnight at rt, then heated to 80° C. for two days. The reaction was cooled down to rt. Con. NH$_4$Cl (10 mL) and brine (10 mL) were added. The mixture was extracted by t-BuOMe (2×30 mL). The organic phase was dried over Na$_2$SO$_4$. was separated. Removal of volatile materials gave a residue, which was purified by column chromatography (4:1 ethyl acetate/hexanes) to afford a pure product (11) (2.0 g, 45%). $\delta_H$ 1.25 (3H, s), 3.1-3.7 (6H, m), 3.18 (6H, s), 4.5-4.7 (1H, m) ppm.

Compound 12: To a solution 11 (1.8 g, 3.9 mmol) in DCM (20 mL) was added TFA (1.71 g, 15 mmol) and water (0.36 g). The mixture was stirred for 1 h at rt. Removal of volatile materials gave a residue, which was partitioned in water (30 mL) and t-BuOMe (20 mL). The separated aqueous layer was washed with t-BuOMe (20 mL). Water was evaporated to give a residue, which was co-evaporated with CH$_3$CN (2×30 mL) to remove the trace water. A product (12) (0.43 g, 64%) obtained, without further purification for next step. $\delta_H$ 2.15 (3H, s), 3.47-3.90 (5H, m), 4.06 (1H, s), 4.59-4.72 (1H, m) ppm.

2. Preparation of Libraries (Parallel Synthesis):

Sulfonates: To a solution of a sulfonyl chloride (K) (0.1 mmol) in dry DCM (1 mL) were add a solution of 12 (0.1 mmol, 0.1 M) in DCM and triethyl amine (20.2 mg, 0.2 mmol). The mixture was standing overnight at rt. The reaction was completed. The product was purified with preparative TLC.

(23) Library 13-Sulfonates:

| Entry | MW | Wt/V | mMol |
|-------|--------|------|------|
| K2    | 221.62 |      | 0.1  |
| K5    | 182.65 |      | 0.1  |
| K6    | 254.71 |      | 0.1  |
| K10   | 253.06 |      | 0.1  |
| K11   | 327.71 |      | 0.1  |
| K12   | 227.67 |      | 0.1  |
| K19   | 229.09 |      | 0.1  |
| K21   | 218.62 |      | 0.1  |
| K22   | 253.07 |      | 0.1  |
| K23   | 234.69 |      | 0.1  |
| K54   | 317.69 |      | 0.1  |
| K60   | 259.74 |      | 0.1  |
| K83   | 234.69 |      | 0.1  |
| K90   | 194.61 |      | 0.1  |

-continued

| Entry | MW | Wt/V | mMol |
|---|---|---|---|
| K91 | 255.52 | | 0.1 |
| K92 | 232.73 | | 0.1 |
| K93 | 244.62 | | 0.1 |
| K94 | 245.51 | | 0.1 |
| K96 | 256.06 | | 0.1 |
| K97 | 289.62 | | 0.1 |
| K98 | 302.86 | | 0.1 |
| K99 | 266.57 | | 0.1 |
| K100 | 235.65 | | 0.1 |
| K101 | 217.63 | | 0.1 |
| K102 | 201.63 | | 0.1 |

Reaction Procedure:

Amine Compound Synthesis:

Method 1:

a). Alkylation:

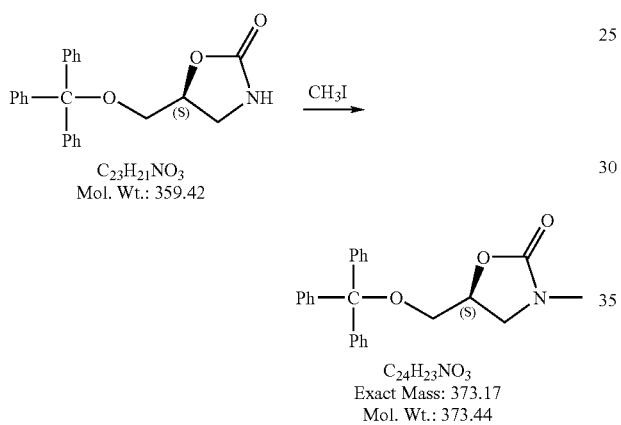

$C_{23}H_{21}NO_3$
Mol. Wt.: 359.42

$C_{24}H_{23}NO_3$
Exact Mass: 373.17
Mol. Wt.: 373.44

| Materials | d | MW | Wt/V | mMol |
|---|---|---|---|---|
| SM | | 359.42 | 14.8 g | 41 |
| 60% NaH | | 24 | 2.0 g | 50 |
| G3 | 2.28 | 141.94 | 3.6 mL | 61.5 |
| THF | | | 140 mL | |

Procedure:
1. To a solution of oxazolidinone and THF, sodium hydride power was added under N2 protection, and ice bath.
2. The mixture was stirred for half hour at 0° C., then let it warm up to room temperature.
3. G3 was added into the solution slowly, and the reaction was stirred for overnight.
4. The reaction was quenched with water and extracted with Ethyl acetate/hexane mixture. The combined organic layer was washed with NH₄Cl, brine and dried over Na₂SO₄.
5. The organic solvents were removed by water Rota-vap and the crude residue was carried on next step without purification.

b). Deprotection:

$C_{24}H_{23}NO_3$
Exact Mass: 373.17
Mol. Wt.: 373.44

$C_5H_9NO_3$
Exact Mass: 131.06
Mol. Wt.: 131.13

| Materials | d | MW | Wt/V | mMol | equiv |
|---|---|---|---|---|---|
| SM | | 373.17 | crude | 41 | |
| TFA | 1.48 | 114.02 | 4.7 mL | 62 | 1.5 |
| water | | 18 | 1.5 mL | 82 | 2.0 |
| CH₂Cl₂ | | | 10 ml | | |

Procedure:
1. The mixture was stirred for 3 h at room temperature.
2. The reaction was quenched by three drops of triethyl amine and dried over Na₂SO₄.
3. The solvents were removed by Rota-vap and the residue was purified by column chromatography. The elute solvents: 2/1=hexane/EtOAc to 1/2=hexane/EtOAc, then use pure EtOAc.

c). Tosylation and Azidelation:

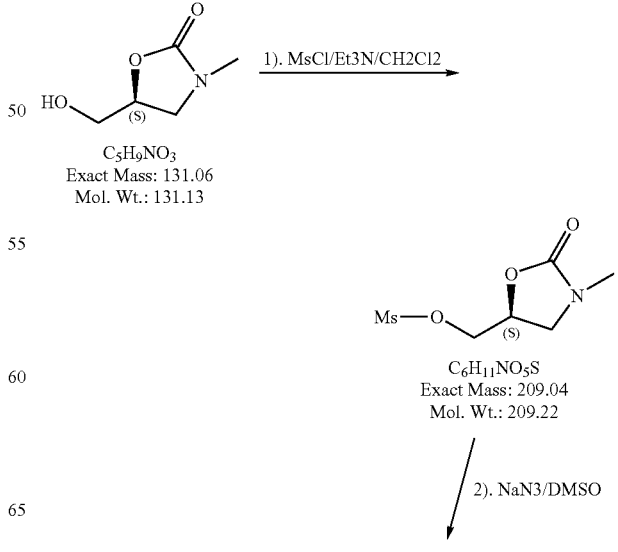

$C_5H_9NO_3$
Exact Mass: 131.06
Mol. Wt.: 131.13

$C_6H_{11}NO_5S$
Exact Mass: 209.04
Mol. Wt.: 209.22

-continued

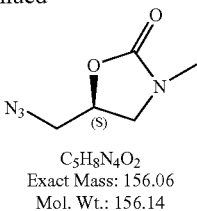

C₅H₈N₄O₂
Exact Mass: 156.06
Mol. Wt.: 156.14

| Materials | d | MW | Wt/V | mMol | Equiv |
|---|---|---|---|---|---|
| SM | | 131.13 | 3.93 | 30 | 1 |
| MsCl | 1.48 | 114.55 | 3.01 | 39 | 1.3 |
| Et₃N | | 101 | 5.8 mL | 42 | 1.4 |
| CH₂Cl₂ | | | | | |
| THF | | | | | |
| DMSO | | | | | |
| NaN₃ | | 65 | 3.1 g | 48 | 1.6 |

Procedure:

1). Starting material was treated with methanesulfonyl chloride in the presence of triethylamine in methylene chloride.

2) The reaction mixture was stirred at ice bath for 3 hours.

3). The reaction was washed with water and the organic layer was dried over Na₂SO₄

4). The organic solvent was removed to give the residue, which was treated with sodium azide in DMSO, 5) The result solution was heated up to 80° C. for two hours, then diluted with water and extracted with methylene chloride.

6). The organic layer was dried over Na₂SO₄

7). The solvent was removed and the crude was purified by flash column chromatography to afford azide compound.

d). Hydrogenation

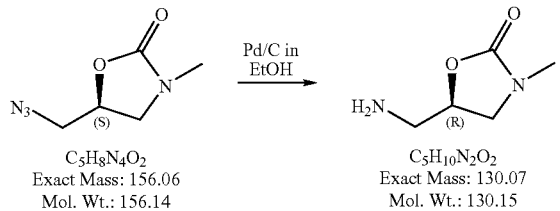

C₅H₈N₄O₂
Exact Mass: 156.06
Mol. Wt.: 156.14

C₅H₁₀N₂O₂
Exact Mass: 130.07
Mol. Wt.: 130.15

Oxazolidinone: 3.4 g

Pd—C (10%): 800 mg

EtOH: 30 mL
1. Hydrogenation bottle was charged with azide compound and EtOH.
2. Flushed with N₂
3. Pd—C was deactivated with two drops of water then added into the reaction mixture.
4. Reaction was run for overnight under hydrogenater with 30 Psi (2 atmosphere)
5. TLC showed complete conversion and the reaction mixture was filtered under water pump.
6. The residue (2.46 g) was obtained and used to carry on next step without purification.

Library Design:
Oxazolidinones: RC2, SP40 (0.08 nM) in CH₂Cl₂
Acid chlorides: E0, E2, E8, E92, E124, E154, E157, E159, E117, E120, E164, E136

Parallel Synthesis Procedure:

1). Oxazolidinones (0.16 nM) were made and transferred into small vials.

2). To those vials Et₃N (1.5 equiv) was added.

3). After 20 mins, acid chlorides or sulfonyl chlorides were added into the reaction vials.

4). The compounds were isolated by CombiFlash, sq 16× open access purification system.

Library:
Oxazolidinones: RC2, SP40 (0.08 nM) in CH₂Cl₂
Sulfonyl chlorides: K2, K3, K4, K10, K21, K22, K23, K83, K90, K91, K92, K93, K94, K95, K96, K97, K98, K99, K100

Parallel Synthesis Procedure:

1). Oxazolidinones (0.16 nM) were made and transferred into small vials.

2). To those vials Et3N (1.5 equiv) was added.

3). After 20 mins, acid chlorides or sulfonyl chlorides were added into the reaction vials.

4). The compounds were isolated by para-TLC (2/1=EtOAC/Hexane).

Nitrogen linkage library compound synthesis

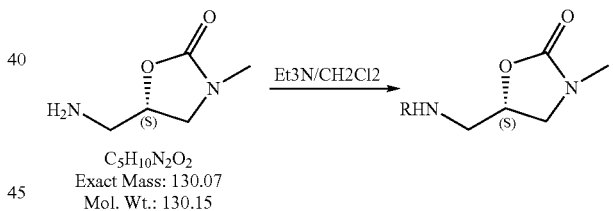

C₅H₁₀N₂O₂
Exact Mass: 130.07
Mol. Wt.: 130.15

Library Design:
Oxazolidinone: amine
Acid Chloride: E0, E2, E8, E92, E124, E154, E157, E159, E117, E120, E164, E136
Sulfonyl chlorides: K2, K3, K4, K10, K21, K22, K23, K83, K90, K91, K92, K93, K94, K95, K96, K97, K98, K100

Parallel Synthesis Procedure:

1). Oxazolidinones (0.01 nM) were made and transferred into small vials.

2). To those vials Et3N (1.5 equiv) was added.

3). After 20 mins, acid chlorides or sulfonyl chlorides were added into the reaction vials.

4). The compounds were isolated by para-TLC (2/1 EtOAC/Hexane).

Library:

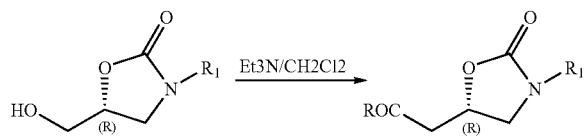

Oxazolidinones: SG3, SC3, and SC5 (0.08 nM) in $CH_2Cl_2$
Acid chlorides: E0, E2, E8, E92, E124, E154, E157, E159, E117, E120, E164, E136

Parallel Synthesis Procedure:

1). Oxazolidinones (0.16 nM) were made and transferred into small vials.
2). To those vials Et3N (1.5 equiv) was added.
3). After 20 mins, acid chlorides or sulfonyl chlorides were added into the reaction vials.
4). The compounds were isolated by para-TLC (2/1 EtOAC/Hexane).

Ether Type of Linkages:

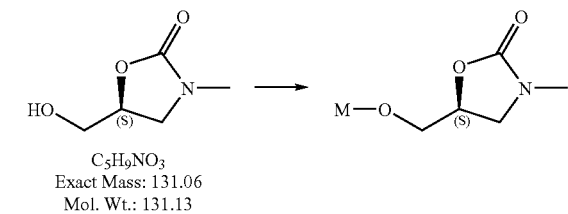

$C_5H_9NO_3$
Exact Mass: 131.06
Mol. Wt.: 131.13

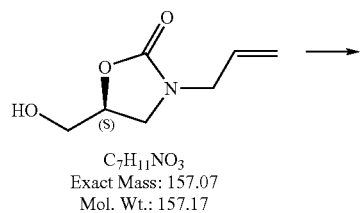

$C_7H_{11}NO_3$
Exact Mass: 157.07
Mol. Wt.: 157.17

Library Design:
Oxazolidinones: SG3, SC5
M compounds: M1, M2, M3, M4, M5, M6, M6, M11, M14, M14, M24, M30 M34, M35, M37, M38 DEAD=0.10 nM in THF (MW 174

$Ph_3P$-polystyrene 1 mmol/g 100 mg for each compound 0.1 mMol

THF 1 mL

Procedure:
1. The vials were charged with starting material, THF, $CH_2Cl_2$ and $Ph_3P$-polystrene.
2. A solution of DEAD was added into the reaction mixture.
3. The reactions were stand for overnight.
4. Separated by pre-TLC.

N-Aryl linkage:

Using Buchwald Reaction:

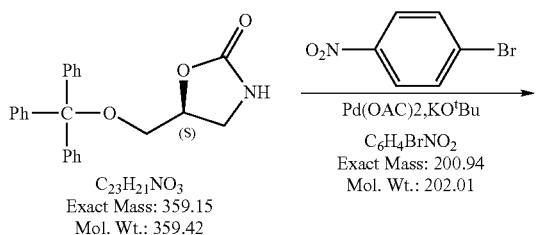

$C_{23}H_{21}NO_3$
Exact Mass: 359.15
Mol. Wt.: 359.42

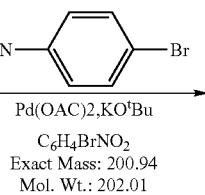

$C_6H_4BrNO_2$
Exact Mass: 200.94
Mol. Wt.: 202.01

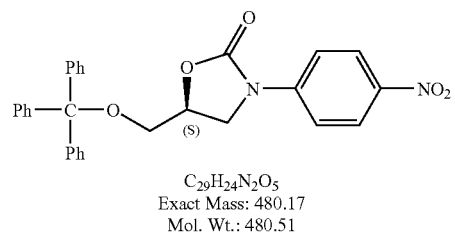

$C_{29}H_{24}N_2O_5$
Exact Mass: 480.17
Mol. Wt.: 480.51

| Materials | d | MW | Wt/V | mMol equiv |
|---|---|---|---|---|
| SM | | 359.42 | 1.0 g | 2.7 | 1 |
| Bromo compound | | 202.01 | 0.76 g | 3.7 | 1.3 |
| Palladium(II) acetate | | 224.49 | 82 mg | 0.36 | 0.13 |
| sodium t-butoxide | | 96.11 | 0.4 g | 4.16 | 1.5 |
| Ferrocene | | 554.40 | 155 mg | 0.27 | 0.1 |
| Toluene | | | 140 mL | | |

Procedure:

1. A 100 mL flask loaded with oxazolidinone, bromo compound, palladium(II) acetate, 1,1'-bis(diphenylphosphino)-ferrocene and sodium t-butoxide and flashed by N2 protection for 10 mins.
2. Toluene was added and heated up to 110° C. for overnight and then diluted with dichloromethane after it cooled down to room temperature.

Buchwald Reaction:

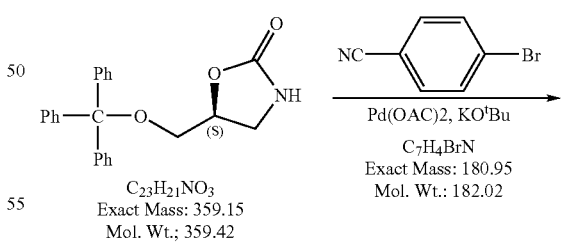

$C_{23}H_{21}NO_3$
Exact Mass: 359.15
Mol. Wt.; 359.42

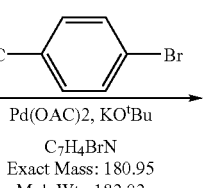

$C_7H_4BrN$
Exact Mass: 180.95
Mol. Wt.: 182.02

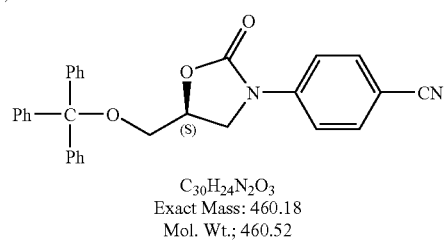

$C_{30}H_{24}N_2O_3$
Exact Mass: 460.18
Mol. Wt.; 460.52

| Materials | d | MW | Wt/V | mMol | equiv |
|---|---|---|---|---|---|
| SM | | 359.42 | 6.0 g | 16.7 | 1 |
| Bromo compound | | 182.12 | 3.65 g | 20 | 1.2 |
| Palladium(II) acetate | | 224.49 | 487 mg | 2.2 | 0.13 |
| sodium t-butoxide | | 96.11 | 2.4 g | 25 | 1.5 |
| Ferrocene | | 554.40 | 926 mg | 1.67 | 0.1 |
| Toluene | | | 140 mL | | |

Procedure:
1. A 100 mL Round flask was loaded with oxazolidinone, bromo compound, palladium(II) acetate, 1,1'-bis(diphenylphosphino)-ferrocene and sodium t-butoxide and flashed by $N_2$ protection for 10 mins.
2. Toluene was added and heated up to 110° C. for overnight and then cool down to room temperature, diluted with dichloromethane.
3. filtered by celite.
4. Separated by column. EtOAc/Hexane=4 elute solvent.

Synthesis of 3-trityloxy-2-hydroxy-propylamine

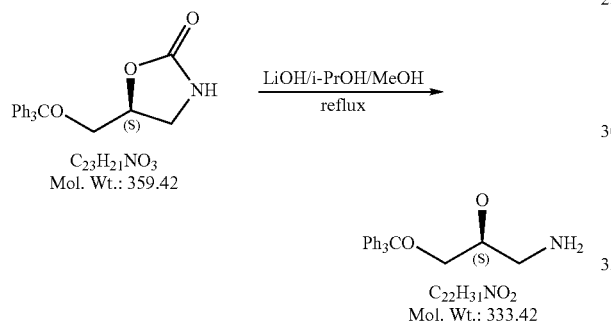

Procedure:
1. To a 500 mL Round flask was charged with 18 g SM and 90 mL of isopropyl alcohol 10 mL of MeOH then 50 mL of LiOH saturated solution.
2. The mixture was heated under reflux overnight at ~70° C.
3. Cool down to room temperature and solvents were removed on Rota-vap.
4. Extract with EtOAc (1×50 mL, and 1×50 mL).
5. The combined EtOAc layers was washed with saturated NaCl, and dried with anhydrous $Na_2SO_4$.
6. The solid was filtered and solution was divided into three parts and concentrated them separately.
Total 18.05 g, 100% yield was obtained.

Amine Oxazolidinone Formation:

Method 2:

a). Hydrazine Formation:

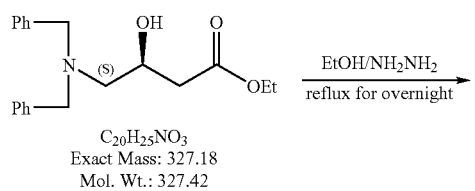

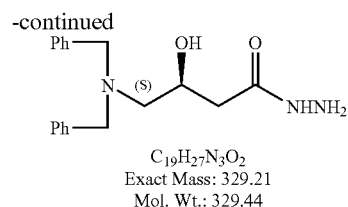

| Materials | d | MW | Wt/V | mMol | Equiv |
|---|---|---|---|---|---|
| SM | | 327.18 | 5.7 g | 17.42 | 1 |
| EtOH | | | 10 mL | | |
| hydrazine | 32 | | 3 mL | 26 | 1.5 |

1. To a round flask was Loaded hydrazine, EtOH and ester.
2. The reaction was heated up to reflux for overnight.
3. The solvents were removed by water rota-vap.
4. NMR showed there is no ester.

b). Curtius Rearrangement:

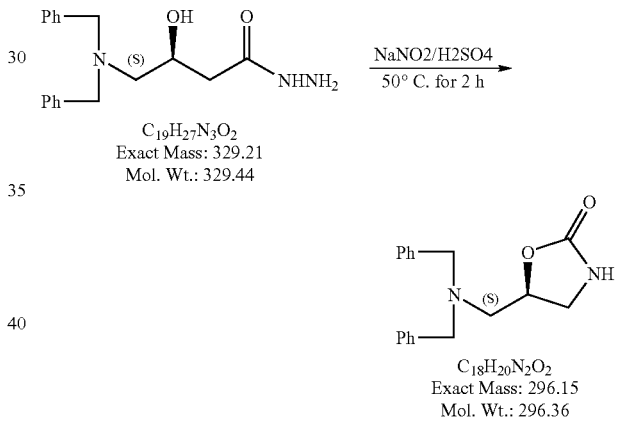

| Materials | d | MW | Wt/V | mMol | Equiv |
|---|---|---|---|---|---|
| SM | | 329.44 | | 17.4 | 1 |
| $H_2SO_4$ | | 98 | 2.04 g | 20.8 | 1.2 |
| $NaNO_2$ | | 69 | 2.4 | 34.8 | 2 |
| water | | | 17 mL | | |

Procedure:
1). The hydrazide compound was dissolved in water (17 mL).
2). To the reaction mixture, concentrated sulfuric acid (2.04 g) diluted in water (10 mL) was added into the stirred solution.
3). The mixture was cooled in the ice bath and then NaNO2 was added.
4). The reaction mixture was stirred at 50° C. for 2 hrs.

Buchwald Reaction:

*Org. Lett.*, Vol. 2, No. 8, 2000

Pd-Catalyzed Amination of Activated Aryl Halides:

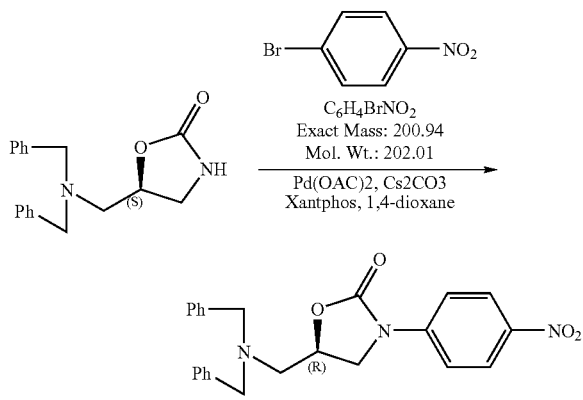

| Materials | d | MW | Wt/V | mMol | equiv |
|---|---|---|---|---|---|
| SM | | 359.42 | 454 mg | 1.26 | 1 |
| Bromo compound | | 202 | 305 mg | 1.5 | 1.2 |
| Pd(OAC)2 | | 224.49 | 2.9 mg | 0.013 | 0.01 |
| Cesium carbonate | | 325.82 | 575 mg | 1.8 | 1.4 |
| Xantphos | | 578.63 | 10 mg | 0.018 | 0.015 |
| 1,4-dioxane | | | 3 mL | | |

Procedure:

1. A 10 mL Round flask was loaded with oxazolidinone, bromo compound, palladium(II) acetate, Xantphos and Cesium carbonate.
2. The flask was back-filled $N_2$ for 10 mins.
3. 1,4-dioxane was added and heated up to 100° C. for overnight and then cool down to room temperature, diluted with dichloromethane.
4. filtered by silicon gel.
5.

| Oxazolidinone | MW |
|---|---|
| SC2 | 169.18 |
| SC3 | 184 |
| SG2 | 173 |
| B11 | 295.26 |
| SG3 | 131.13 |
| K2 | 221.62 |
| K10 | 253.06 |
| K6 | 254.72 |

Desired Products:

SC2K2, SC3K2, SC5K2, SC5K10, SG2K10, B11K6, SG3K2

0.2 nmol of starting material were used in the presence of 3 equivalent of triethylamine as base in 1 mL of dichloromethane. The reactions were stirred for overnight.

Remake some of the library compounds for testing according to the result on Mar. 14, 2002.

| Oxazolidinone | MW |
|---|---|
| SC3 | 184 |
| SG2 | 173 |
| SG3 | 131.13 |
| K2 | 221.62 |
| K10 | 253.06 |
| K3 | 206.65 |
| K23 | 234.68 |
| K22 | 254.12 |
| SG3-N | 130.07 |
| E8 | 212.63 |

Desired Products:

SC3E8, SG3E8, SG3-N-E8, SG3-N-K2, SG3-N-K3,

Procedure:

0.1 nmol of starting material were used in the presence of 1.5 equivalent of triethylamine as base in 1 mL of dichloromethane. The reactions were stirred for overnight.

E112-Oxazolidione Library Compound Synthesis:

O-Linkage and N-Linkage:

| Oxazolidinone | MW |
|---|---|
| SC2 | 169.18 |
| SC3 | 184 |
| SG2 | 173 |
| B11 | 295.26 |
| B10 | 264 |
| SG3 | 131.1 |
| SG3—NH— | 130.07 |
| SC5 | 157 |
| SC1 | 157 |

Desired Products:

SC3E112, SG3-N-E112, SG3-E112, SC1E112, B11E112.

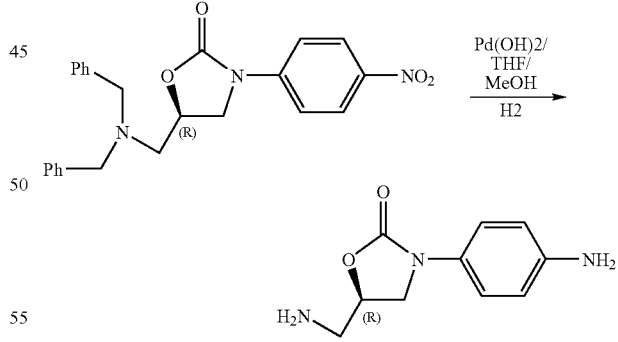

300 mg of ZD3-75-2

500 mg of Pd(OH)2

5 mL of THF 5 mL of MeOH

The reaction was stirred at room temperature 10 mins (see new spot and starting material on TLC, new spot is more polar) and 40 mins (see one new spot, which is less polar than starting material, and only one spot shown on TLC).

111 / 112

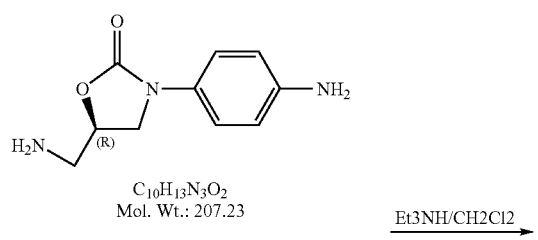

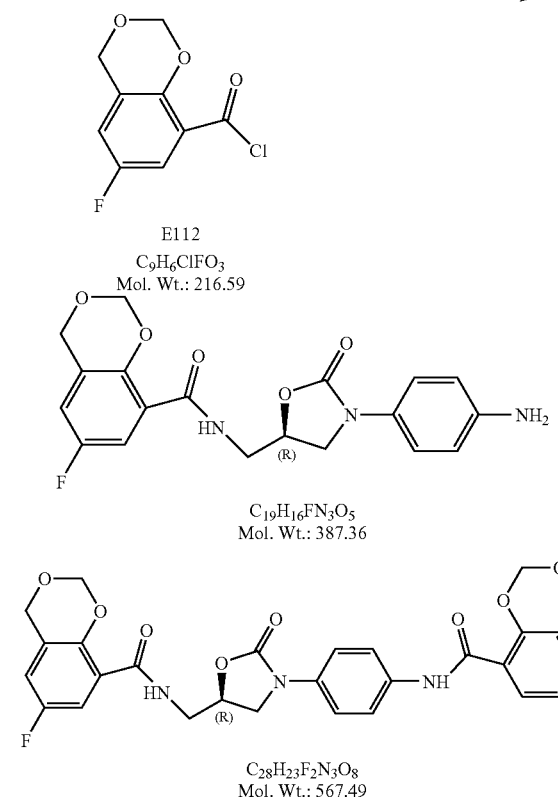

Variety of E112-Oxazolidione Library Compound Synthesis:

| Oxazolidinone | MW |
|---|---|
| RC2 | 169.18 |
| B10 | 264 |
| SG3 | 131.1 |
| SC5 | 157 |
| RC5 | 157 |
| RC1 | 157 |

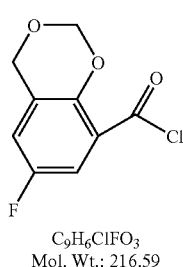

E112

Desired Products:

| | | | |
|---|---|---|---|
| RC2 E112 | SB10 E112 | SG3 E112 | SC5 E112 |
| RC5 E112 | RC1 E112 | ZD3-87-E112 (387.36 or 567.49), | |
| ZD3-88-1 (206.24), ZD3-88-2 (206.24), ZD3-88-3 (206.24) | | | |

Exploring New Linkages:

1). Copper-Catalyzed Coupling of Alkylamines and Aryl Iodides

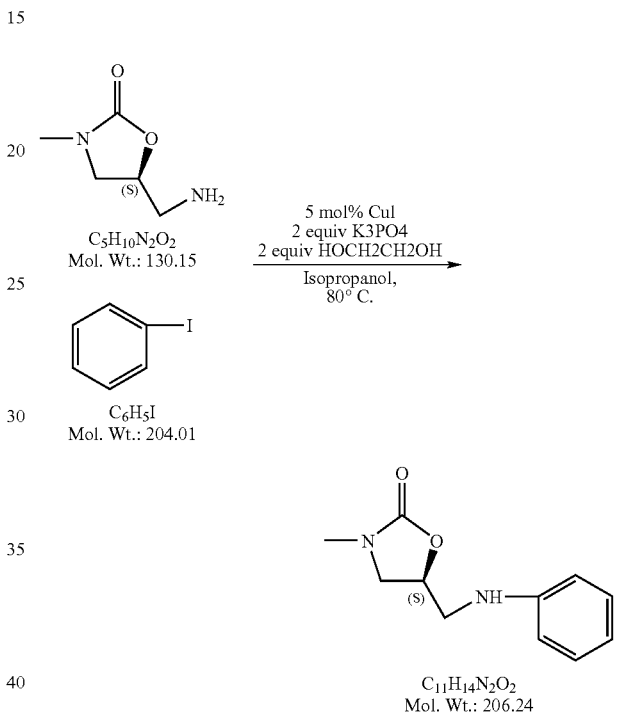

| Materials | d | MW | Wt/V | mMol | equiv |
|---|---|---|---|---|---|
| SM | | 130.15 | 100 mg | | 1 |
| Iodo compound | | 204.0 | 170 mg | | 1.1 |
| CuI | | 190.44 | 7.6 mg | | 0.05 |
| K$_3$PO$_4$ | | 212.5 | 322 mg | | 2 |
| HO(CH$_2$)$_2$OH | 1.13 | 62.07 | 0.1 mL | | 2 |
| Isopropanol | | | 1 mL | | |

Procedure:

To a schlenk tube, CuI and K$_3$PO$_4$ were added then the tube was back-filled with nitrogen for 10 mins, and then rest of starting material were added, the reaction mixture was heated up to 80° C.

Results and Discussion:

Desired product was obtained by para-TLC. (2/1=EtOAc/Hexane).

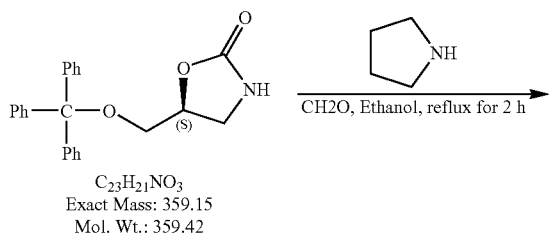

C₂₃H₂₁NO₃
Exact Mass: 359.15
Mol. Wt.: 359.42

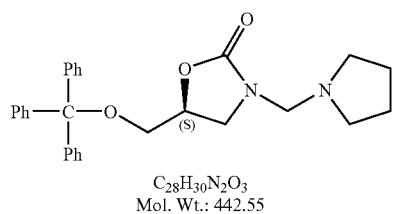

C₂₈H₃₀N₂O₃
Mol. Wt.: 442.55

| Materials | d | MW | Wt/V | mMol | equiv |
|---|---|---|---|---|---|
| SM | | 359.42 | 0.5 g | 2.78 | 1 |
| Pyrrolidine | | | 0.2 mL | | |
| 37% HCHO | | | 0.2 mL | | |
| Ethanol | | | 6 mL | | |

Procedure:

A solution of SM, pyrrolidine and formaldehyde in ethanol (6 mL) was refluxed for 2 h. The solvent was evaporated.

Copper-Catalyzed Coupling of Alkylamines and Aryl Iodides

*Organic Lett.* 2002 Vol. 4, No. 4. page 581-584

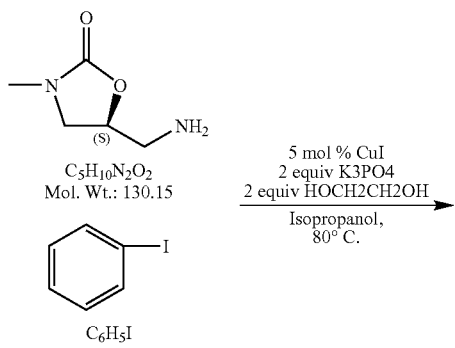

C₅H₁₀N₂O₂
Mol. Wt.: 130.15

C₆H₅I
Mol. Wt.: 204.01

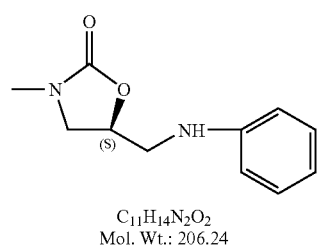

C₁₁H₁₄N₂O₂
Mol. Wt.: 206.24

| Materials | d | MW | Wt/V | mMol | equiv |
|---|---|---|---|---|---|
| SM | | 130.15 | 100 mg | | 1 |
| Iodo compound | | 204.0 | 170 mg | | 1.1 |
| CuI | | 190.44 | 7.6 mg | | 0.05 |
| K₃PO₄ | | 212.5 | 322 mg | | 2 |
| HO(CH₂)₂OH | 1.13 | 62.07 | 0.1 mL | | 2 |
| Isopropanol | | | 1 mL | | |

Procedure:

To a schlenk tube, CuI and K₃PO₄ were added then the tube was back-filled with Nitrogen for 10 mins, and then rest of starting material were added, the reaction mixture was heated up to 80° C.

Copper-Catalyzed Coupling of Alkylamines and Aryl Iodides

*Organic Lett.* 2002 Vol. 4, No. 4. page 581-584

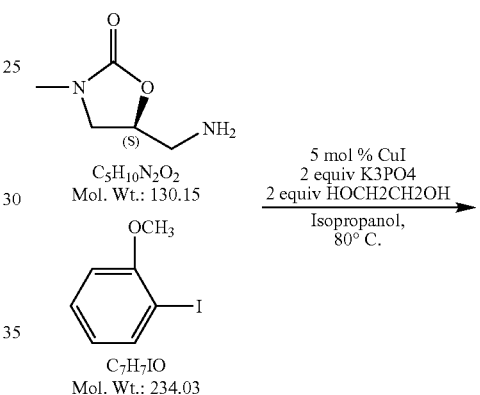

C₅H₁₀N₂O₂
Mol. Wt.: 130.15

C₇H₇IO
Mol. Wt.: 234.03

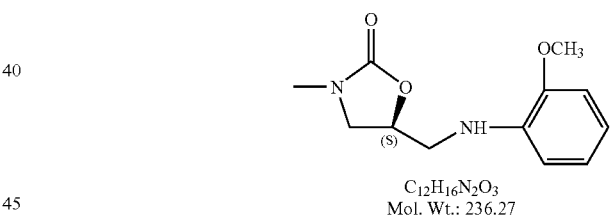

C₁₂H₁₆N₂O₃
Mol. Wt.: 236.27

| Materials | d | MW | Wt/V | mMol | equiv |
|---|---|---|---|---|---|
| SM | | 130.15 | 100 mg | 0.76 | 1 |
| Iodo compound | | 234.0 | 211 mg | 0.84 | 1.1 |
| CuI | | 190.44 | 7.6 mg | | 0.05 |
| K₃PO₄ | | 212.5 | 322 mg | | 2 |
| HO(CH2)2OH | 1.13 | 62.07 | 0.1 mL | | 2 |
| Isopropanol | | | 1 mL | | |

Procedure:

To a schlenk tube, CuI and K₃PO₄ were added then the tube was back-filled with Nitrogen for 10 mins, and then rest of starting material were added, the reaction mixture was heated up to 90° C.

Copper-Catalyzed Coupling of Alkylamines and Aryl Iodides

*Organic Lett.* 2002 Vol. 4, No. 4. page 581-584

115

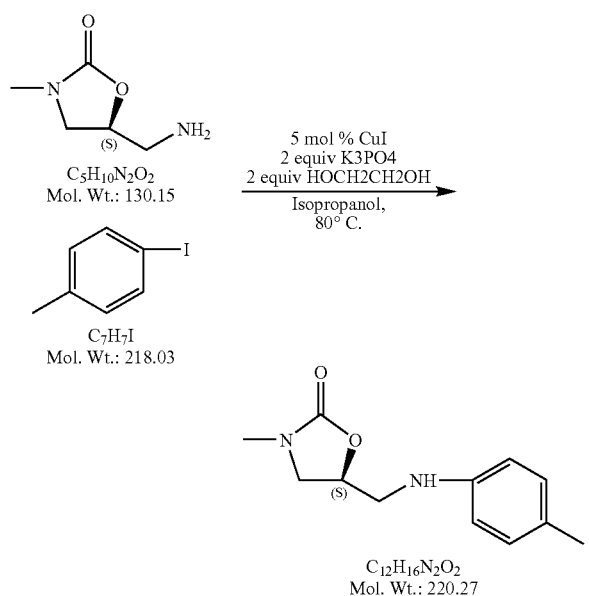

| Materials | d | MW | Wt/V | mMol | equiv |
|---|---|---|---|---|---|
| SM | | 130.15 | 40 mg | | 1 |
| Iodo compound | | 218.0 | 72 mg | | 1.1 |
| CuI | | 190.44 | 3 mg | | 0.05 |
| K$_3$PO$_4$ | | 212.5 | 128 mg | | 2 |
| HO(CH$_2$)$_2$OH | 1.13 | 62.07 | 0.1 mL | | 2 |
| Isopropanol | | | 1 mL | | |

Procedure:

To a schlenk tube, CuI and K$_3$PO$_4$ were added then the tube was back-filled with Nitrogen for 10 mins, and then rest of starting material were added, the reaction mixture was heated up to 90° C.

CAN. J. CHEM. Vol. 61, 411 (1983)

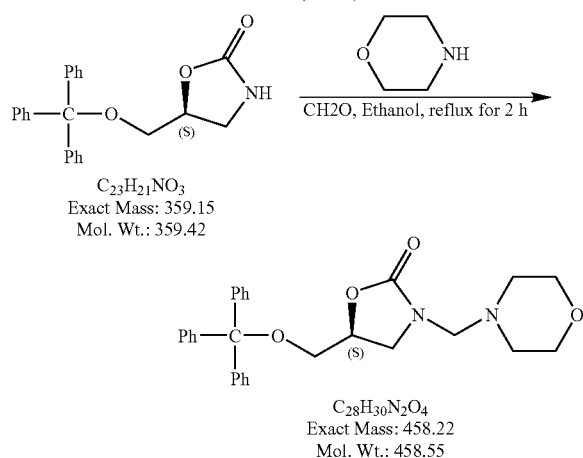

| Materials | d | MW | Wt/V | mMol | equiv |
|---|---|---|---|---|---|
| SM | | 359.42 | 0.68 g | 2.78 | 1 |
| Morpholine | | 87.12 | 0.4 mL | | |
| 37% HCHO | | | 0.4 mL | | |
| Ethanol | | | 8 mL | | |

116

Procedure:

A solution of SM, morpholine and formaldehyde in 8 mL in ethanol was refluxed for 4 h. The solvent was evaporated.

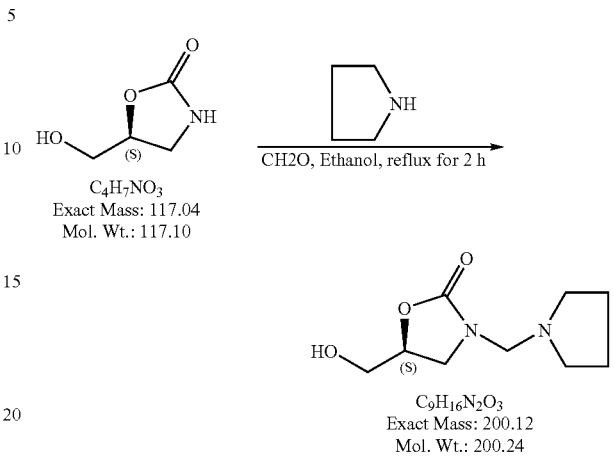

| Materials | d | MW | Wt/V | mMol | equiv |
|---|---|---|---|---|---|
| SM | | 117 | 0.47 g | | |
| Pyrrolidine | | | 0.2 mL | | |
| 37% HCHO | | | 0.4 mL | | |
| Ethanol | | | 3 mL | | |

Procedure:

A solution of SM, morpholine and formaldehyde in 3 mL in ethanol was refluxed for 2 h. The solvent was evaporated.

Deprotection:

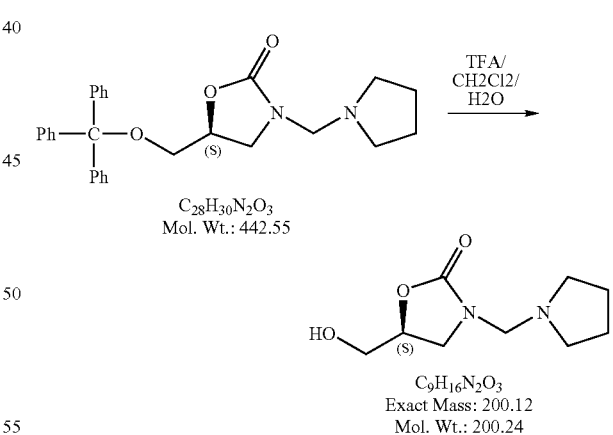

| Materials | d | MW | Wt/V | mMol | equiv |
|---|---|---|---|---|---|
| SM | | 442.55 | 24 mg | 0.05 | 1 |
| TFA | | | one drop | | |
| H$_2$O | | | one drop | | |
| CH$_2$Cl$_2$ | | | 1 mL | | |

Stir for Overnight.

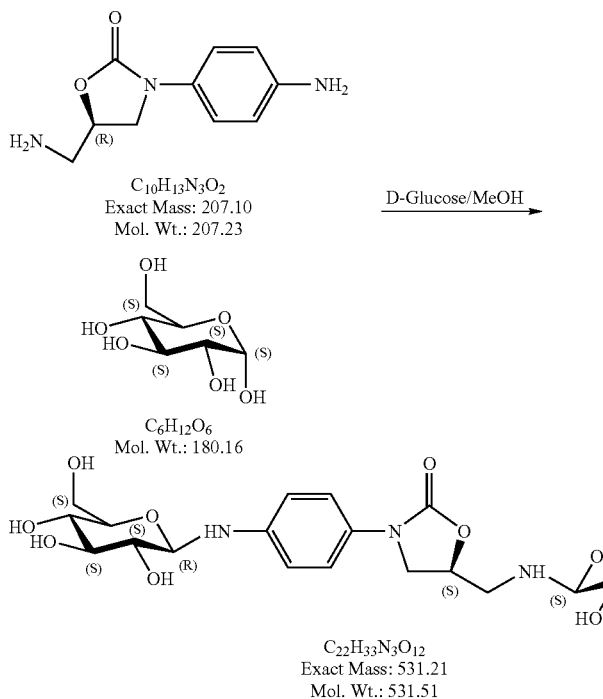

amine compound: 18 mg

D-glucose: 140 mg

MeOH: 3 mL

Procedure:

To a schlenk tube was added Amine compound, D-glucose and MeOH. The reaction was heated up to 60° C. for overnight.

Copper-Catalyzed Coupling of Alkylamines and Aryl Iodides

*Organic Lett.* 2002 Vol. 4, No. 4. page 581-584

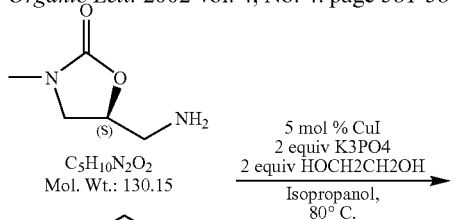

| Materials | d | MW | Wt/V | mMol | equiv |
|---|---|---|---|---|---|
| SM | | 130.15 | 40 mg | | 1 |
| Iodo compound | | 218.0 | 72 mg | | 1.1 |
| CuI | | 190.44 | 3 mg | | 0.05 |
| $K_3PO_4$ | | 212.5 | 128 mg | | 2 |
| $HO(CH_2)_2OH$ | 1.13 | 62.07 | 0.1 mL | | 2 |
| Isopropanol | | | 1 mL | | |

Procedure:

To a schlenk tube, CuI and $K_3PO_4$ were added then the tube was back-filled with Nitrogen for 10 mins, and then rest of starting material were added, the reaction mixture was heated up to 95° C. for overnight.

Copper-Catalyzed Coupling of Alkylamines and Aryl Iodides

*Organic Lett.* 2002 Vol. 4, No. 4. page 581-584

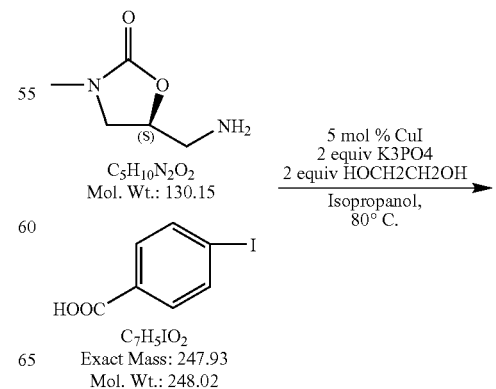

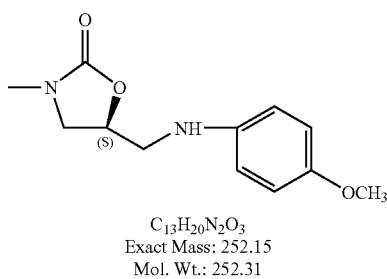

-continued

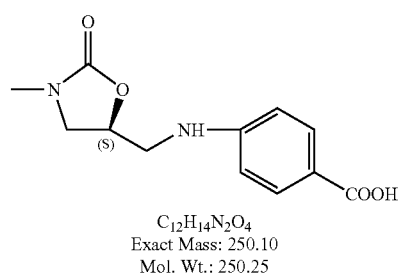

C₁₂H₁₄N₂O₄
Exact Mass: 250.10
Mol. Wt.: 250.25

| Materials | d | MW | Wt/V | mMol | equiv |
|---|---|---|---|---|---|
| SM | | 130.15 | 40 mg | | 1 |
| Iodo compound | | 248.0 | 72 mg | | 1.0 |
| CuI | | 190.44 | 3 mg | | 0.05 |
| K₃PO₄ | | 212.5 | 128 mg | | 2 |
| HO(CH2)2OH | 1.13 | 62.07 | 0.1 mL | | 2 |
| Isopropanol | | | 1 mL | | |

Procedure:

To a schlenk tube, CuI and K₃PO₄ were added then the tube was back-filled with Nitrogen for 10 mins, and then rest of starting material were added, the reaction mixture was heated up to 95° C. for overnight.

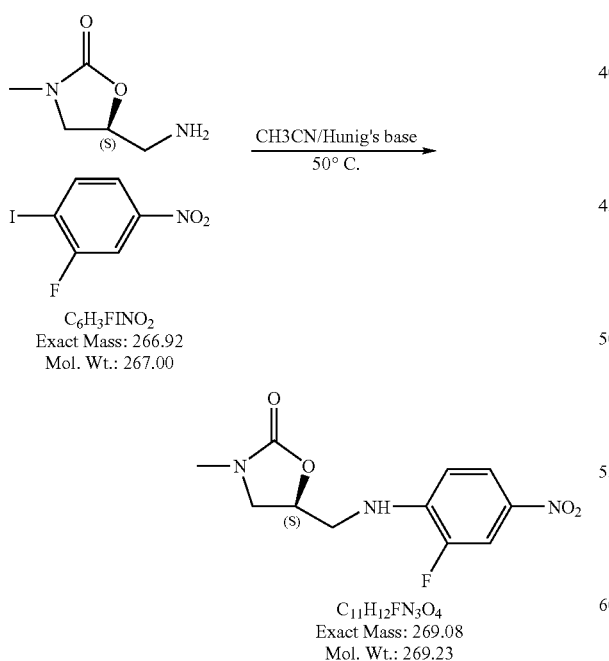

C₆H₃FINO₂
Exact Mass: 266.92
Mol. Wt.: 267.00

C₁₁H₁₂FN₃O₄
Exact Mass: 269.08
Mol. Wt.: 269.23

The solution of 4 equiv of Hunig's base and 1 equiv of amine starting material in CH₃CN was stirred at 50° C. for overnight.

Reduction of Nitro Group

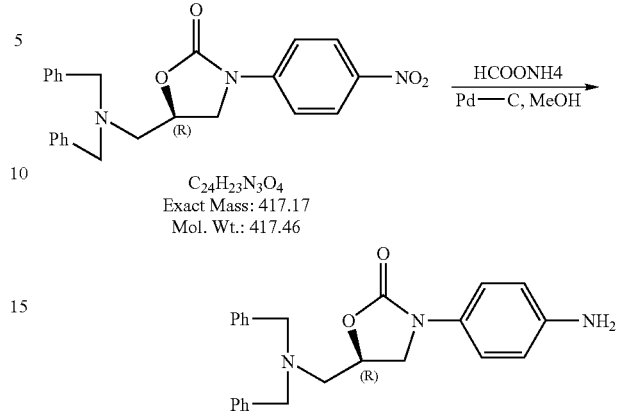

C₂₄H₂₃N₃O₄
Exact Mass: 417.17
Mol. Wt.: 417.46

C₂₄H₂₅N₃O₂
Exact Mass: 387.19
Mol. Wt.: 387.47

| Materials | d | MW | Wt/V | mMol | equiv |
|---|---|---|---|---|---|
| SM | | 417.46 | 70 mg | 0.24 | 1 |
| HCOONH₄ | | 63 | 56 | 0.88 | 3.6 |
| Pd/C | | | | (Wt) | 10 |
| THF | | | 0.4 mL | | |
| MeOH | | | 0.4 mL | | |

1. To a solution of oxazolidinone and THF-MeOH(1:1) was Ammonium formate and Pd—C.
2. The reaction was stirred at room temperature for 2 h.
3. Diluted with THF.
4. Filtered and washed several times with THF.
5. Filtrate concentrated to a dark yellow solid.

Reduction of Nitro Group

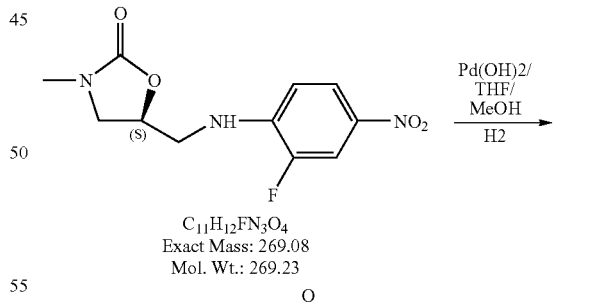

C₁₁H₁₂FN₃O₄
Exact Mass: 269.08
Mol. Wt.: 269.23

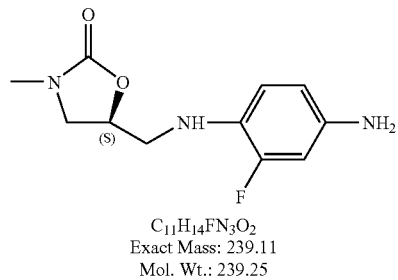

C₁₁H₁₄FN₃O₂
Exact Mass: 239.11
Mol. Wt.: 239.25

| Materials | d | MW | Wt/V | mMol | equiv |
|---|---|---|---|---|---|
| SM | | 269.23 | 120 | 0.45 | 1 |
| Pd(OH)$_2$ | | | | | 10% |
| THF | | | | | |
| MeOH | | | 1 mL | | |

The reaction was stirred at room temperature under H$_2$ for 2 hrs.

Deprotection:

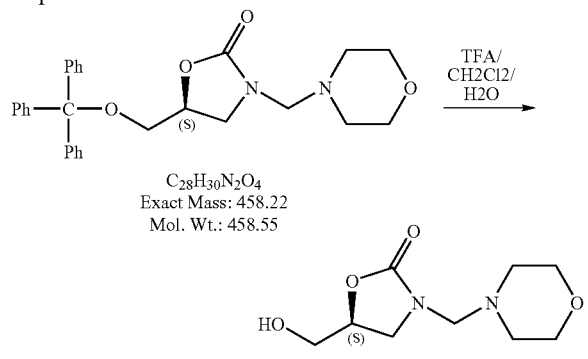

C$_{28}$H$_{30}$N$_2$O$_4$
Exact Mass: 458.22
Mol. Wt.: 458.55

C$_9$H$_{16}$N$_2$O$_4$
Exact Mass: 216.11
Mol. Wt.: 216.23

| Materials | d | MW | Wt/V | mMol | equiv |
|---|---|---|---|---|---|
| SM | | 458.55 | 800 mg | 0.57 | 1 |
| TFA | | | 0.3 mL | | |
| H$_2$O | | | 0.1 mL | | |
| CH$_2$Cl$_2$ | | | 3 mL | | |

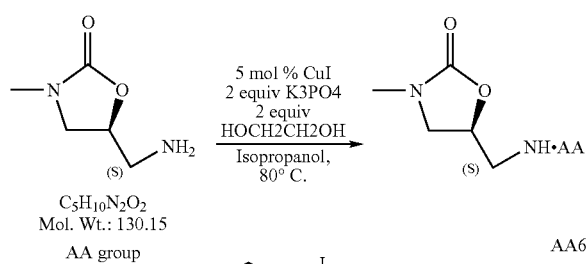

C$_5$H$_{10}$N$_2$O$_2$
Mol. Wt.: 130.15
AA group

AA6

C$_6$H$_4$INO$_2$
Exact Mass: 248.93
Mol. Wt.: 249.01

AA7

C$_6$H$_4$INO$_2$
Exact Mass: 248.93
Mol. Wt.: 249.01

-continued

AA8

C$_6$H$_4$INO$_2$
Exact Mass: 248.93
Mol. Wt.: 249.01

AA9

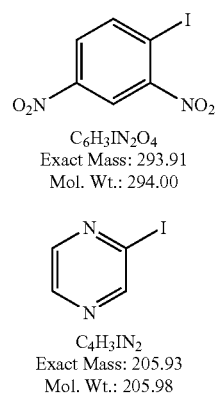

C$_6$H$_3$IN$_2$O$_4$
Exact Mass: 293.91
Mol. Wt.: 294.00

AA12

C$_4$H$_3$IN$_2$
Exact Mass: 205.93
Mol. Wt.: 205.98

| Materials | d | MW | Wt/V | mMol | equiv |
|---|---|---|---|---|---|
| SM | | 130.15 | 40 mg | 0.31 | 1 |
| CuI | | 190.44 | 3 mg | | 0.05 |
| K$_3$PO$_4$ | | 212.5 | 128 mg | | 2 |
| HO(CH$_2$)$_2$OH | 1.13 | 62.07 | 0.1 mL | | 2 |
| Isopropanol | | | 1 mL | | |

AA Group: 0.31 mmol

AA6 77 mg

AA7 77 mg

AA9 91 mg

AA12 65 mg

Procedure:
To a test tube, CuI and K$_3$PO$_4$ were added then the tube was back-filled with Nitrogen for 10 mins, and then rest of starting material were added, the reaction mixture was heated up to 80° C. for overnight.

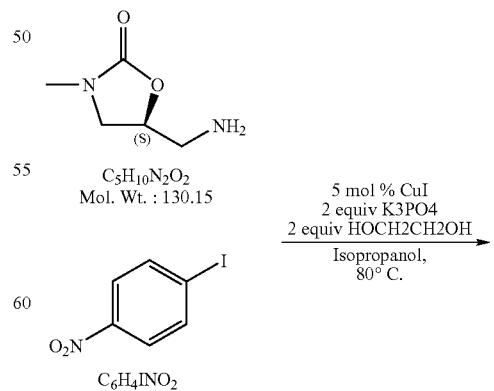

C$_5$H$_{10}$N$_2$O$_2$
Mol. Wt. : 130.15

C$_6$H$_4$INO$_2$
Exact Mass: 248.93
Mol. Wt.: 249.01
AA 8

-continued

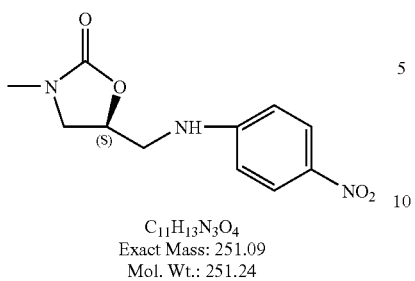

C₁₁H₁₃N₃O₄
Exact Mass: 251.09
Mol. Wt.: 251.24

| Materials | d | MW | Wt/V | mMol | equiv |
|---|---|---|---|---|---|
| SM | | 130.15 | 200 mg | | |
| CuI | | 190.44 | 15 mg | | |
| K₃PO₄ | | 212.5 | 640 mg | | |
| HO(CH₂)₂OH | 1.13 | 62.07 | 0.5 mL | | |
| Isopropanol | | | 2 mL | | |
| AA8 | | 249 | 385 mg | | |

Procedure:

To a test tube, CuI and K₃PO₄ were added then the tube was back-filled with Nitrogen for 10 mins, and then rest of starting material were added, the reaction mixture was heated up to 90° C. for overnight.

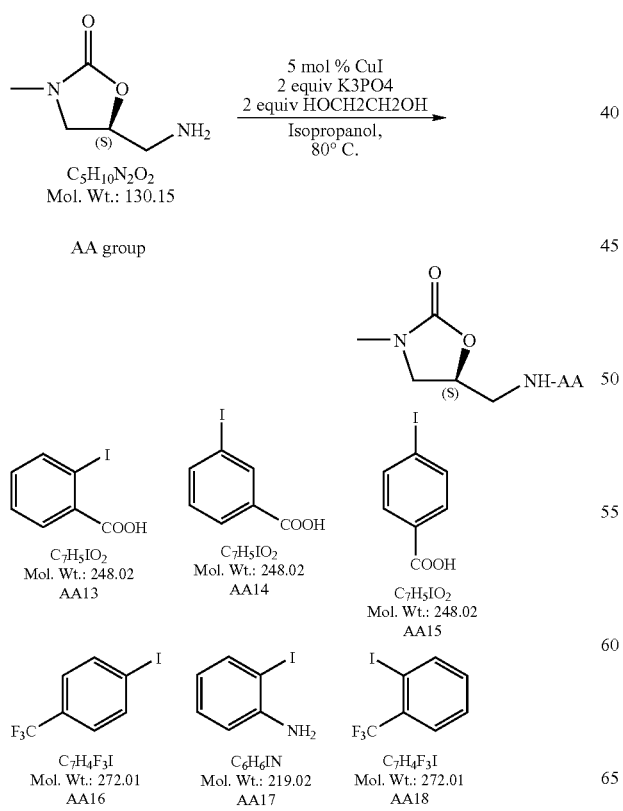

-continued

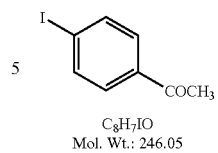

C₈H₇IO
Mol. Wt.: 246.05
AA19

| Materials | d | MW | Wt/V | mMol | equiv |
|---|---|---|---|---|---|
| SM | | 130.15 | 40 mg | 0.31 | 1 |
| CuI | | 190.44 | 3 mg | | 0.05 |
| K₃PO₄ | | 212.5 | 128 mg | | 2 |
| HO(CH2)2OH | 1.13 | 62.07 | 0.1 mL | | 2 |
| Isopropanol | | | 1 mL | | |

AA Group: 0.31 mmol

AA13, AA14, AA15 77 mg; AA16, AA18 84 mg; AA17 68 mg; AA19 77 mg

Procedure:

To a small vial, CuI and K₃PO₄ were added then the tube was back-filled with Nitrogen for 10 mins, and then rest of starting material were added, the reaction mixture was heated up to 80° C. for overnight.

CAN. J. CHEM. Vol. 61, 411 (1983)

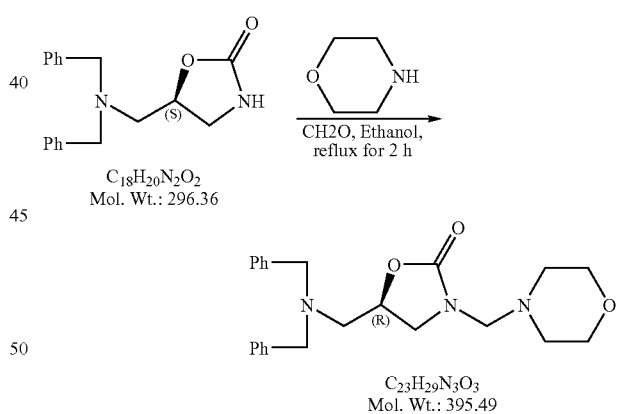

| Materials | d | MW | Wt/V | mMol | equiv |
|---|---|---|---|---|---|
| SM | | 296 | 0.1 g | 0.4 | 1 |
| Morpholine | | 87.12 | 0.1 mL | | |
| 37% HCHO | | | 0.1 mL | | |
| Ethanol | | | 1.5 mL | | |

Procedure:

A solution of SM, morpholine and formaldehyde in 1.5 mL in ethanol was refluxed for 2 h. The solvent was evaporated.

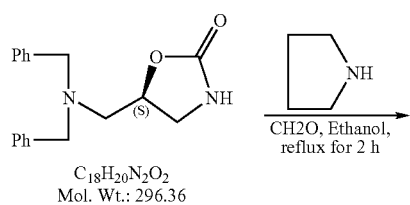

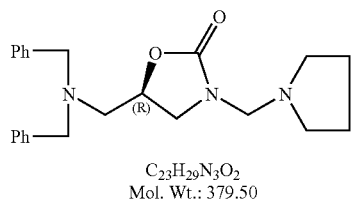

| Materials | d | MW | Wt/V | mMol | equiv |
|---|---|---|---|---|---|
| SM | | 296.36 | 0.1 g | | |
| Pyrrolidine | | | 0.1 mL | | |
| 37% HCHO | | | 0.1 mL | | |
| Ethanol | | | 1.5 mL | | |

Procedure:

A solution of SM, morpholine and formaldehyde in 1.5 mL in ethanol was refluxed for 2 h. The solvent was evaporated.

Ether type of Linkages:

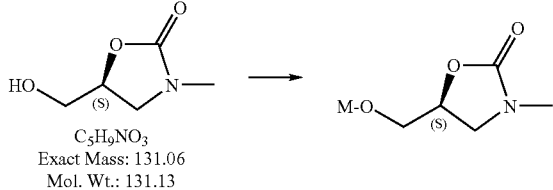

Library Design:

Oxazolidinones: SG3, 130 mg in 5 mL of CHCl2. 0.5 mL was took for each reaction.

M compounds: M1, M4, MS, M11, M14, M24, M30, M35, M37, M38

DIAD=0.10 nM in THF (MW 202), 202 mg in 10 mL THF. 1 mL was for each reaction.

Ph3P-polystyrene 1 mmol/g 100 mg for each compound 0.1 mMol

Procedure:
1. The vials were charged with SM and Ph₃P-polystrene.
2. A solution of DIAD in THF was added into the reaction mixture.
3. The reactions were stirred for overnight.

Ether Type of Linkages:

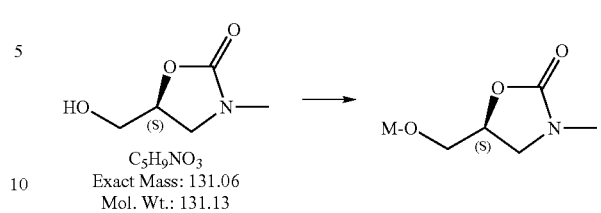

Library Design:

Oxazolidinones: SG3, 130 mg in 5 mL of CHCl2. 0.5 mL was took for each reaction.

M compounds: M9, M13, M20, M21, M22, M23, M23, M29, M32, M33

DIAD=0.10 nM in THF (MW 202), 202 mg in 10 mL THF and 1.5 mL of DMPU as co-solvent. 1.2 mL was took for each reaction.

Ph₃P-polystyrene 1 mmol/g 100 mg for each compound 0.1 mMol

Procedure:
1. The vials were charged with SM and Ph₃P-polystrene.
2. A solution of DIAD in THF was added into the reaction mixture.
3. The reactions were stirred for overnight.

Acid Hydrazide from Ester

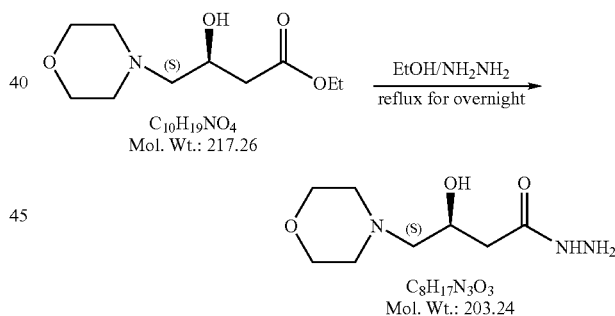

| Materials | d | MW | Wt/V | mMol | Equiv |
|---|---|---|---|---|---|
| SM | | 217.26 | 2 g | 9.2 | 1 |
| EtOH | | | 5 mL | | |
| hydrazine | | 32 | 588 mg | 18.4 | 2 |

1. Loaded hydrazine and EtOH with a round flask and ester was added slowly.
2. The reaction was heated up to reflux for overnight.
3. The solvents were removed by water rota-vap.
4. NMR showed there is no ester.

127

Curtius Rearrangement:

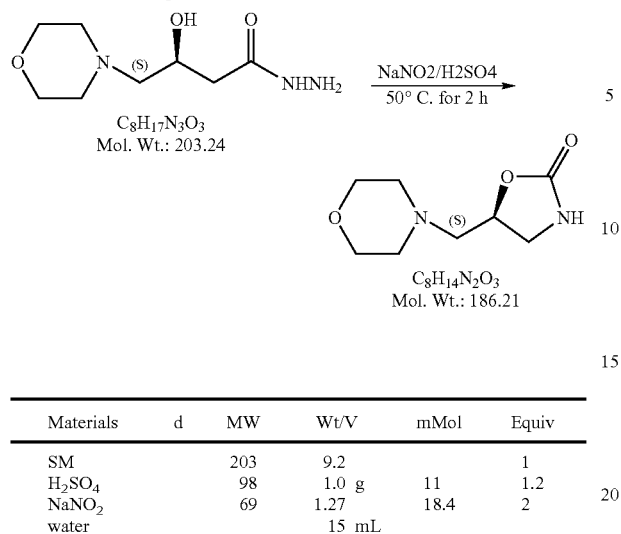

| Materials | d | MW | Wt/V | mMol | Equiv |
|---|---|---|---|---|---|
| SM | | 203 | 9.2 | | 1 |
| H₂SO₄ | | 98 | 1.0 g | 11 | 1.2 |
| NaNO₂ | | 69 | 1.27 | 18.4 | 2 |
| water | | | 15 mL | | |

Procedure:
1). The hydrazide compound was dissolved in water (7 mL), and concentrated sulfuric acid (1.0 g) diluted in water (3 mL) and added into the stirred solution. The mixture was cooled in the ice bath and then NaNO₂ (in 5 mL water) was added slowly.
2). The reaction mixture was stirred at 50° C. for overnight.

Library:

SG3-N- MW 130.15

SG3 MW 131.13

For SG3: K107, K96, K100, K114, K115, K76

For SG3-N: K76, K96, K100, K101, K112, K114, K115. K2

Procedure:

0.10 mol of S 0.15 mmol of Et₃N 0.08 mmol of K compounds

Acid Hydrazide from Ester

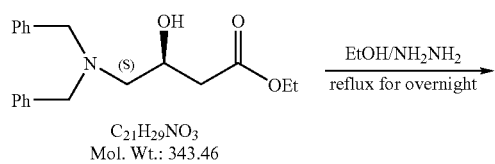

128

-continued

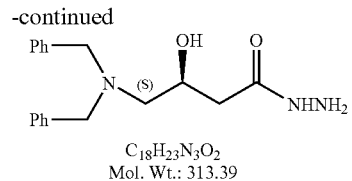

| Materials | d | MW | Wt/V | mMol | Equiv |
|---|---|---|---|---|---|
| SM | | 343.46 | 16 g | 46.6 | 1 |
| EtOH | | | 30 mL | | |
| hydrazine | | 32 | 2.2 g | 70 | 1.5 |

1. Loaded hydrazine and EtOH with a schlenk tube and ester.
2. The reaction was heated up to 80° C. for overnight.
3. The solvents were removed by water rota-vap.

Ether type of Linkages:

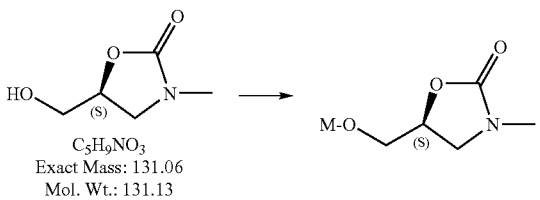

Library Design:

Oxazolidinones: SG3, 104 mg in 4 mL of CH₂Cl₂. 0.5 mL was took for each reaction.

M compounds: M2, M3, M6, M34, M38, M39, M40, M41, DIAD=0.10 nM in THF (MW 202), 160 mg in 8 mL THF. 1 mL was for each reaction.

Ph₃P-polystyrene 1 mmol/g 100 mg for each compound 0.1 mMol

Procedure:
1. The vials were charged with SM and Ph₃P-polystrene.
2. A solution of DIAD in THF was added into the reaction mixture.
3. The reactions were stirred for overnight.

Nitro compounds with special linkages,

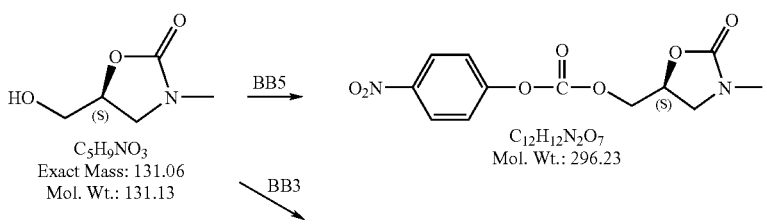

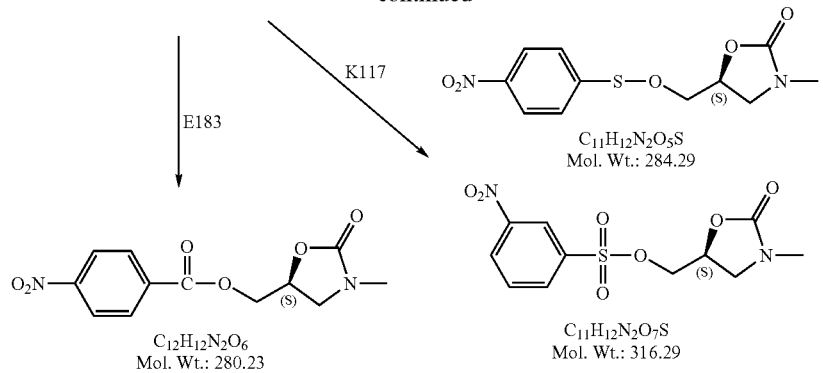
SG3-N- MW 130.15
SG3 MW 131.13
For SG3 and SG3-N: K117, BB3, BB5, E183
Procedure:
0.1 mmol of Starting material
0.15 mmol of Et$_3$N
0.08 mmol of K and B compounds
Exploration of Different Linkages
Alkylation:
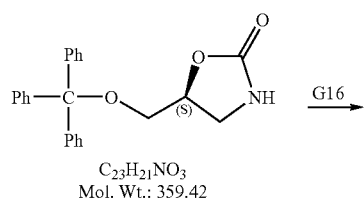
For G16,
| Materials | MW | Wt/V | mMol | Equiv |
|---|---|---|---|---|
| SM | 359.42 | 1 g | 2.78 | 1 |
| G16 | 143.42 | 0.6 mL | | |
| t-BuOK | | 3 mL | | |
| THF | | 8 mL | | |
For G14
| Materials | M | Wt/V | mMol | Equiv |
|---|---|---|---|---|
| SM | 359.42 | 1 g | 2.78 | 1 |
| G14 (d 2.1) | 209.94 | 0.4 mL | 4.17 | 1.5 |
| t-BuOK | | 3 mL | | |
| THF | | 8 mL | | |
Alkylation: (By NaH)
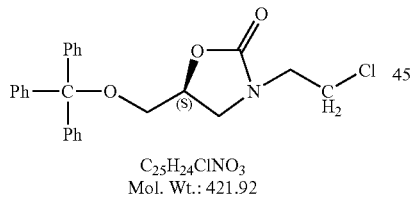
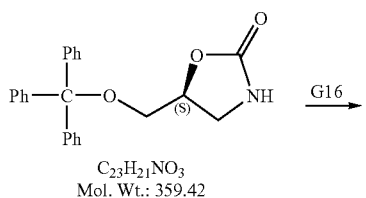
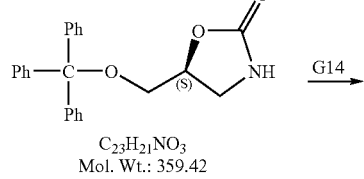
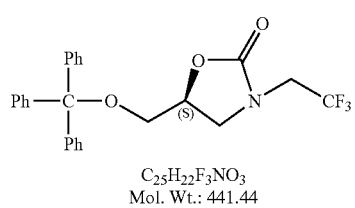
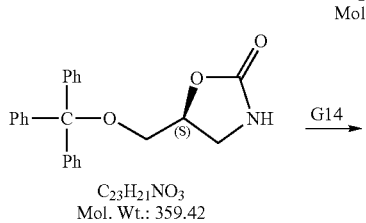

-continued

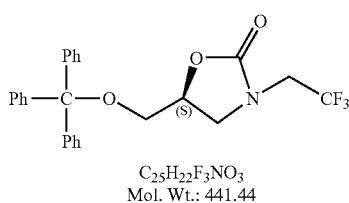

C$_{25}$H$_{22}$F$_3$NO$_3$
Mol. Wt.: 441.44

For G16,

| Materials | MW | Wt/V | mMol | Equiv |
|---|---|---|---|---|
| SM | 359.42 | 1 g | 2.78 | 1 |
| G16 | 143.42 | 0.6 mL | | |
| NaH (60%) | 24 | 166 mg | 4.17 | 1.5 |
| THF | | 8 mL | | |

For G14

| Materials | MW | Wt/V | mMol | Equiv |
|---|---|---|---|---|
| SM | 359.42 | 1 g | 2.78 | 1 |
| G14 (d 2.1) | 209.94 | 0.4 mL | 4.17 | 1.5 |
| NaH (60%) | 24 | 166 mg | 4.17 | 1.5 |
| THF | | 8 mL | | |

Alkylation: (By NaH)

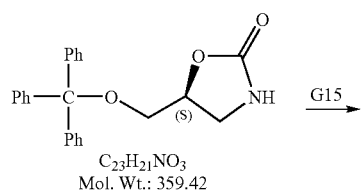

C$_{23}$H$_{21}$NO$_3$
Mol. Wt.: 359.42

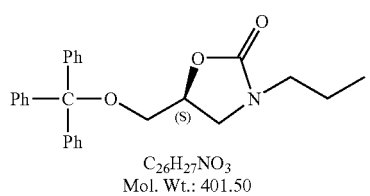

C$_{26}$H$_{27}$NO$_3$
Mol. Wt.: 401.50

For G16,

| Materials | MW | Wt/V | mMol | Equiv |
|---|---|---|---|---|
| SM | 359.42 | 6.5 g | 18.1 | 1 |
| G15 (d1.74) | 170 | 2.5 mL | | |
| NaH (60%) | 24 | 941.2 mg | | |
| THF | | 50 mL | | |

Deprotection: (G15)

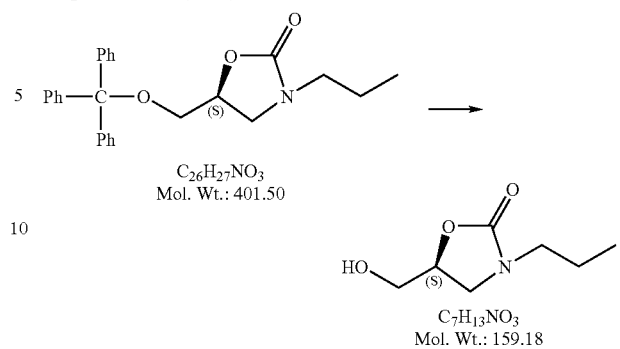

TFA 2 mL

H$_2$O 0.5 mL

CH$_2$Cl$_2$ 5 mL

Deprotection: (Combine 1 g of the Reaction of G16 with BuOK and with NaH)

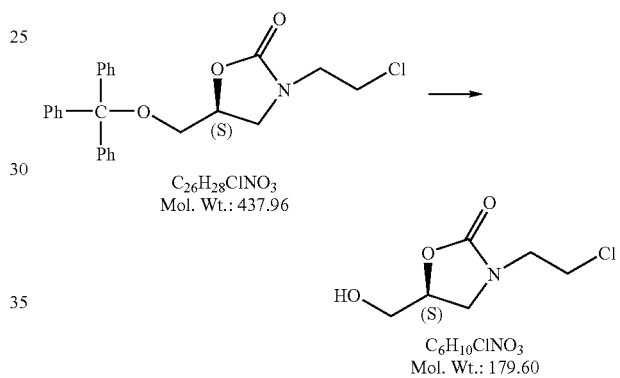

TFA 1 mL

H$_2$O 0.3 mL

CH$_2$Cl$_2$ 3 mL

Glycosylation:

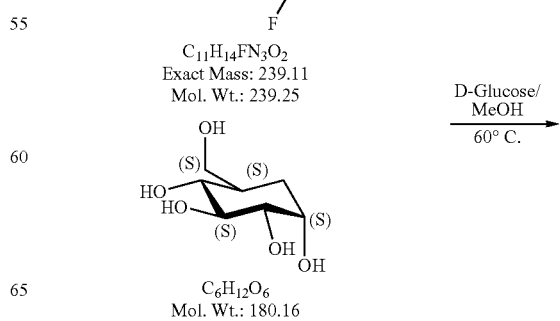

C$_{11}$H$_{14}$FN$_3$O$_2$
Exact Mass: 239.11
Mol. Wt.: 239.25

D-Glucose/
MeOH
——→
60° C.

C$_6$H$_{12}$O$_6$
Mol. Wt.: 180.16

-continued

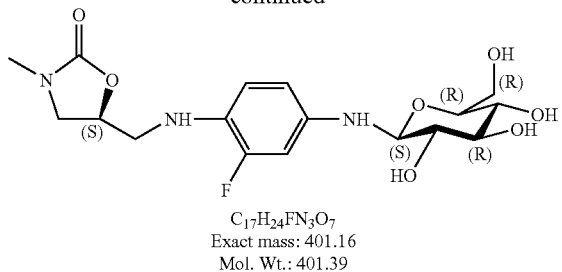

C₁₇H₂₄FN₃O₇
Exact mass: 401.16
Mol. Wt.: 401.39

5 mg of starting material 10 mg of sugar 1 mL of MeOH

Glycosylation

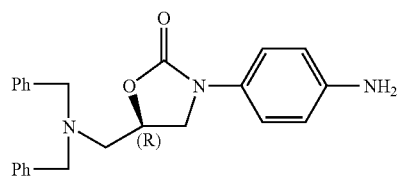

C₂₄H₂₅N₃O₂
Exact Mass: 387.19
Mol. Wt.: 387.47

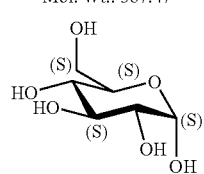

C₆H₁₂O₆
Mol. Wt.: 180.16

D-Glucose/MeOH
⎯⎯⎯⎯⎯⎯⎯→
60° C.

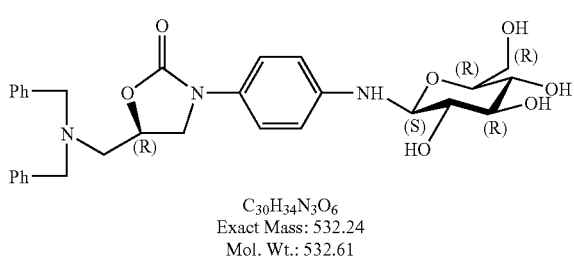

C₃₀H₃₄N₃O₆
Exact Mass: 532.24
Mol. Wt.: 532.61

10 mg of starting material 18 mg of sugar 1 mL of MeOH

Deprotection:

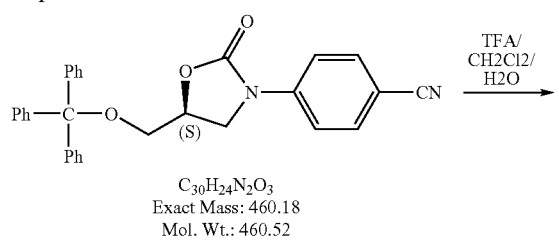

C₃₀H₂₄N₂O₃
Exact Mass: 460.18
Mol. Wt.: 460.52

TFA/
CH2Cl2/
H2O
⎯⎯⎯⎯→

-continued

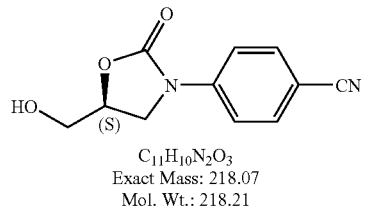

C₁₁H₁₀N₂O₃
Exact Mass: 218.07
Mol. Wt.: 218.21

SM 700 mg

TFA 1.2 mL

H₂O 0.3 mL

CH₂Cl₂ 3 mL

The mixture was stirred for two hours. The TLC showed no starting material left.

Library:

SG3-N- MW 130.15

SG3 MW 131.13

SC3 MW 183.20

K100 (235.65), K101 (221.62), K102 (201.63), K103 (339.51), K104 (229.06), K105 (279.06), K106 (245.51), K107 (212.60), K108 (372.67), K109 (312.62) K110 (240.71), K111 (330.74)

Procedure:

0.11 mol of S 0.15 mmol of Et₃N 0.08 mmol of K compounds

New Library Linkage:

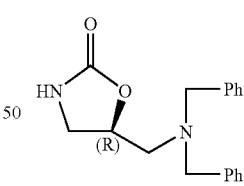

C₁₆H₂₀N₂O₂
Mol. Wt.: 296.36

THF/tBuOK
⎯⎯⎯⎯⎯⎯→
G or C
G2, G3, C1, C3, C2, C5

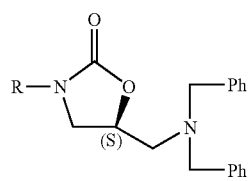

Copper-Catalyzed Coupling of Alkylamines and Aryl Iodides

*Organic Lett.* 2002 Vol. 4, No. 4. page 581-584

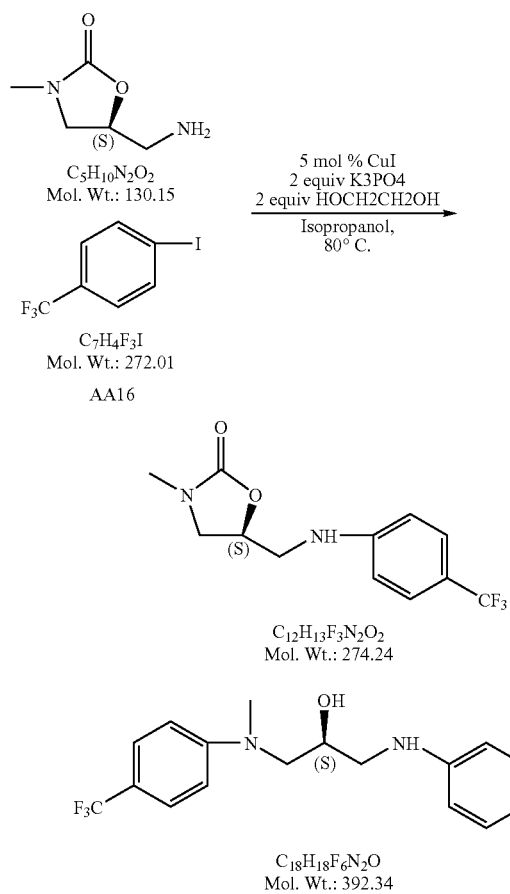

| Materials | d | MW | Wt/V | mMol | equiv |
|---|---|---|---|---|---|
| SM | | 131 | 100 mg | | 1 |
| Iodo compound | | 272.01 | 500 mg | | 1.8 |
| CuI | | 190.44 | 19 mg | | 0.1 |
| K₃PO₄ | | 212.5 | 322 mg | | 2 |
| HO(CH₂)₂OH | 1.13 | 62.07 | 0.15 mL | | 2 |
| Isopropanol | | | 1 mL | | |

Procedure:

To a small vial, CuI and K₃PO₄ were added then the tube was back-filled with Nitrogen for 10 mins, and then rest of starting material were added, the reaction mixture was heated up to 60° C. for overnight, and Isolated by parp-TLC.

CAN. J. CHEM. Vol. 61, 411 (1983)

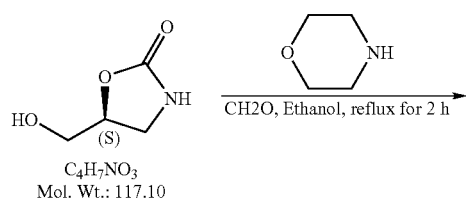

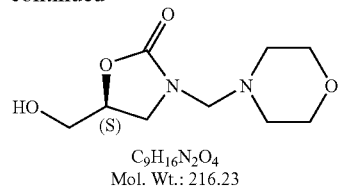

| Materials | d | MW | Wt/V | mMol | equiv |
|---|---|---|---|---|---|
| SM | | 359.42 | 0.1 g | 2.78 | 1 |
| Morpholine | | 87.12 | 0.1 mL | | |
| 37% HCHO | | | 0.05 mL | | |
| Ethanol | | | 1.5 mL | | |

Procedure:

A solution of SM, morpholine and formaldehyde in 1.5 mL in ethanol was heated it up to 60° C. for overnight.

CAN. J. CHEM. Vol. 61, 411 (1983)

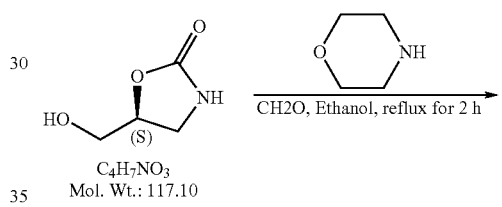

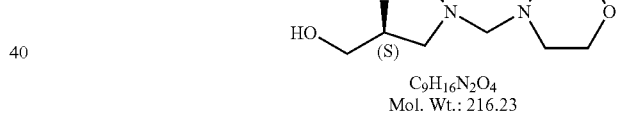

| Materials | d | MW | Wt/V | mMol | equiv |
|---|---|---|---|---|---|
| SM | | 117.10 | 456 mg | 3.9 | 1 |
| Morpholine | | 87.12 | 1 mL | | |
| 37% HCHO | | | 0.4 mL | | |
| Ethanol | | | 3 mL | | |

Procedure:

A solution of SM, morpholine and formaldehyde in 3 mL in ethanol was heated it up to 60° C. for overnight.

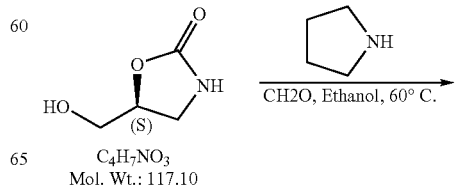

-continued

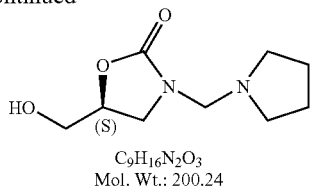

C₉H₁₆N₂O₃
Mol. Wt.: 200.24

| Materials | d | MW | Wt/V | mMol | equiv |
|---|---|---|---|---|---|
| SM | | 117 | 443 mg | 3.78 | 1 |
| pyrrolidine | | | 1 mL | | |
| 37% HCHO | | | 0.4 mL | | |
| Ethanol | | | 3 mL | | |

Procedure:

A solution of SM, morpholine and formaldehyde in 3 mL in ethanol was heated it up to 60° C. for overnight.

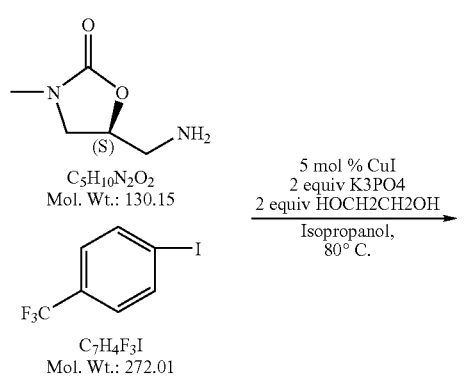

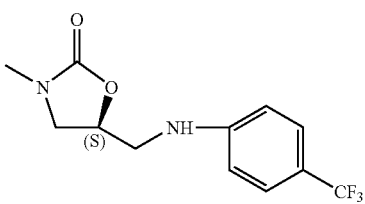

C₁₂H₁₃F₃N₂O₂
Mol. Wt.: 274.24

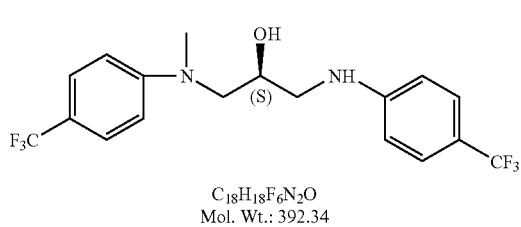

C₁₈H₁₈F₆N₂O
Mol. Wt.: 392.34

| Materials | d | MW | Wt/V | mMol | equiv |
|---|---|---|---|---|---|
| SM | | 130.15 | 40 mg | 0.31 | 1 |
| CuI | | 190.44 | 3 mg | | 0.05 |

-continued

| Materials | d | MW | Wt/V | mMol | equiv |
|---|---|---|---|---|---|
| K₃PO₄ | | 212.5 | 128 mg | | 2 |
| HO(CH₂)₂OH | 1.13 | 62.07 | 0.1 mL | | 2 |
| Isopropanol | | | 1 mL | | |

AA Group: 0.31 mmol

AA20, AA21, AA22, AA23, AA24, AA25, AA26, AA27, AA28

Procedure:

To a test tube, CuI and K₃PO₄ were added then the tube was back-filled with Nitrogen for 10 mins, and then rest of starting material were added, the reaction mixture was heated up to 65° C. for overnight.

Library Linkage:

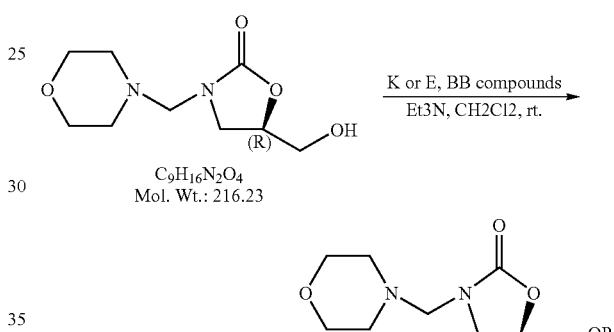

Starting material: 22 mg for each reaction K2, K90, K91, K92, K95, K96, K97, K100, K101, K102, K114, K117, E183, E184, BB3, BB5

Procedure:

0.1 mmol of starting material 0.15 mmol of Et₃N 0.1 mmol of K and BB or E compounds.

The reactions were stirred for overnight.

Buchwald Reaction:

*Org. Lett.*, Vol. 2, No. 8, 2000

Pd-Catalyzed Amination of Activated Ary Halides:

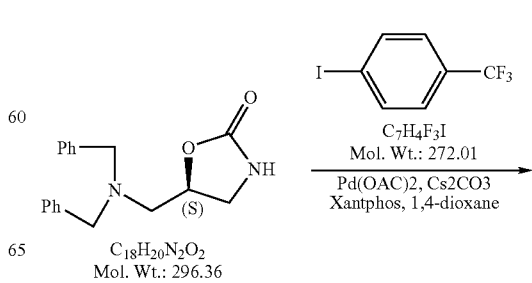

C₁₈H₂₀N₂O₂
Mol. Wt.: 296.36

-continued

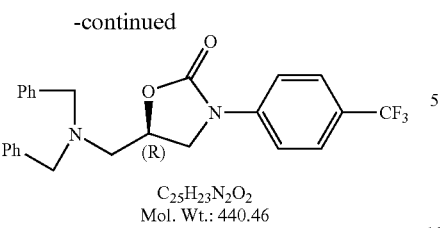

C25H23N2O2
Mol. Wt.: 440.46

| Materials | d | MW | Wt/V | mMol | equiv |
|---|---|---|---|---|---|
| SM |  | 296.36 | 454 mg | 1.6 | 1 |
| Iodo compound |  | 272 | 500 mg | 1.8 | 1.2 |
| Pd(OAC)2 |  | 224.49 | 10 mg | 0.016 | 0.01 |
| Cesium carbonate |  | 325.82 | 730 mg | 2.24 | 1.4 |
| Xantphos |  | 578.63 | 14 mg | 0.024 | 0.015 |
| 1,4-dioxane |  |  | 3 mL |  |  |

Procedure:

1. A 10 mL Round flask was loaded with oxazolidinone, bromo compound, palladium(II) acetate, Xantphos and Cesium carbonate and flashed by N2 protection for 10 mins.

2. 1,4-dioxane was added and heated up to 70° C. for overnight and then cool down to room temperature, diluted with dichloromethane.

Library Linkage:

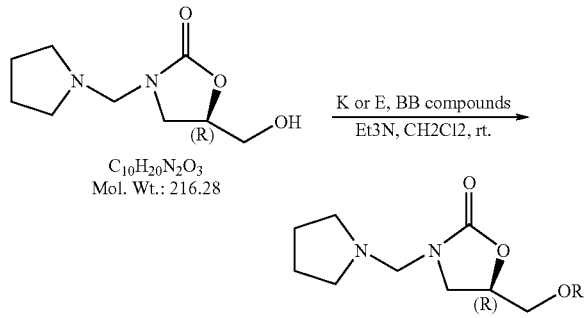

Starting material: 22 mg for each reaction K2, K90, K91, K92, K95, K96, K97, K100, K101, K102, K117, E183, BB3

Procedure:

0.2 mmol of starting material 0.15 mmol of Et3N 0.2 mmol of K and BB or E compounds.

The reactions were stirred for overnight.

Alkylation: (By NaH)

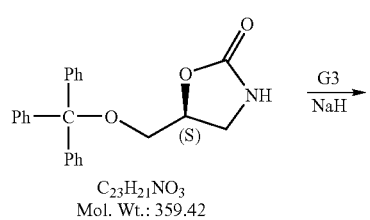

C23H21NO3
Mol. Wt.: 359.42

-continued

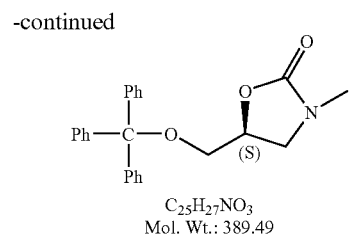

C25H27NO3
Mol. Wt.: 389.49

For G16,

| Materials | MW | Wt/V | mMol | Equiv |
|---|---|---|---|---|
| SM | 359.42 | 50 g | 139 | 1 |
| G3 (d 2.28) | 141.9 | 17 mL | 278 | 2 |
| NaH (60%) | 24 | 10.3 g | 257 | 1.8 |
| THF |  | 400 mL |  |  |

NaH was added into the pre-cooled (by dry ice and acetone) the THF and SM solution, then stirred for two hours. G3 were added after re-cooled the reaction mixture.

Deprotection: (G3)

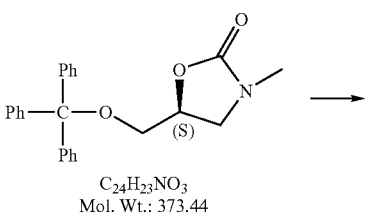

C24H23NO3
Mol. Wt.: 373.44

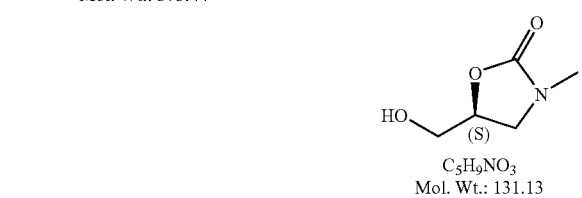

C5H9NO3
Mol. Wt.: 131.13

TFA 14 mL

H2O 4 mL

CH2Cl2 50 mL

Ether Type of Linkages:

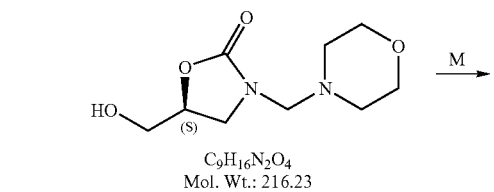

C9H16N2O4
Mol. Wt.: 216.23

Library Design:

Oxazolidinones: 25 mg (1.17 equiv) for each reaction.
M compounds: M1, M2, M3, M4, M5, M6, M11, M14, M24, M30, M34, M35, M37, M38, M39, M40, M41 (1 equiv)

DIAD=0.10 nM in THF (MW 202), 400 mg in 17 mL THF. 1 mL was taken for each reaction.

Ph₃P-polystyrene 1 mmol/g 100 mg for each compound 0.1 mMol

Procedure:
4. The vials were charged with SM and Ph₃P-polystrene.
5. A solution of DIAD in THF was added into the reaction mixture.
6. The reactions were stirred for overnight.

CAN. J. CHEM. Vol. 61, 411 (1983)

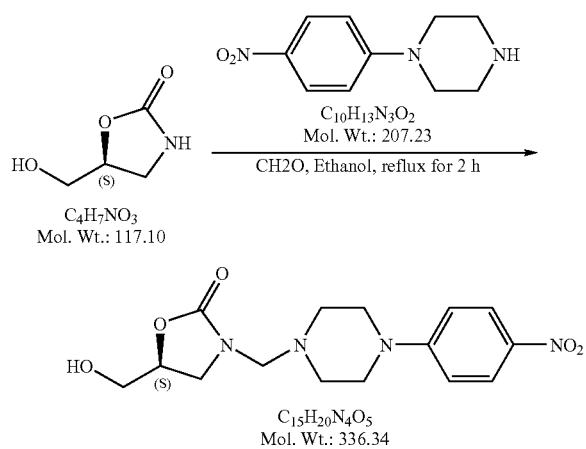

| Materials | d | MW | Wt/V | mMol | equiv |
|---|---|---|---|---|---|
| SM | | 117.10 | 500 mg | | |
| Nitro compound | | 207.23 | 884 mg | | |
| 37% HCHO | | | 0.6 mL | | |
| Ethanol | | | 6 mL | | |

Procedure:
A solution of SM, nitro compound and formaldehyde in 3 mL in ethanol was heated it up to 65° C. for overnight.

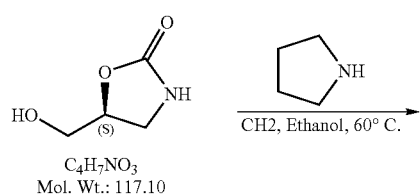

| Materials | d | MW | Wt/V | mMol | equiv |
|---|---|---|---|---|---|
| SM | | 117 | 500 mg | | |
| pyrrolidine | | | 1 mL | | |
| 37% HCHO | | | 0.6 mL | | |
| Ethanol | | | 3 mL | | |

Procedure:
A solution of SM, morpholine, and formaldehyde in 3 mL in ethanol was heated it up to 60° C. for overnight.

Alkylation: (By NaH)

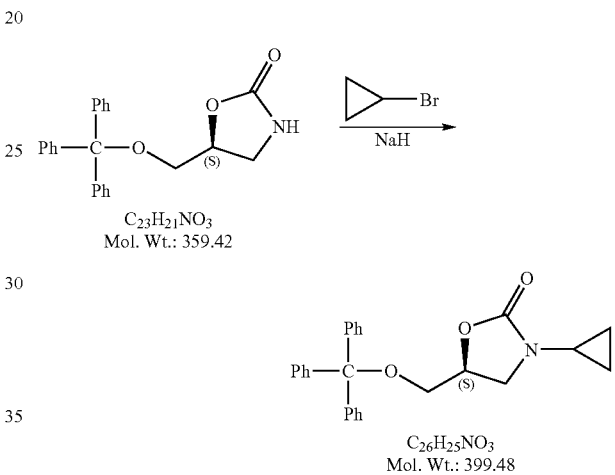

For C18,

| Materials | MW | Wt/V | mMol | Equiv |
|---|---|---|---|---|
| SM | 359.42 | 0.5 g | 1.39 | 1 |
| C18 (d1.5) | 120 | 0.2 mL | 2.78 | 2 |
| NaH (60%) | 24 | 100 mg | 2.57 | 1.8 |
| THF | | 4 mL | | |

NaH was added into the pre-cooled (by dry ice and acetone) the THF and SM solution, then stirred for two hours. G3 were added after re-cooled the reaction mixture.

alkylation: (By NaH)

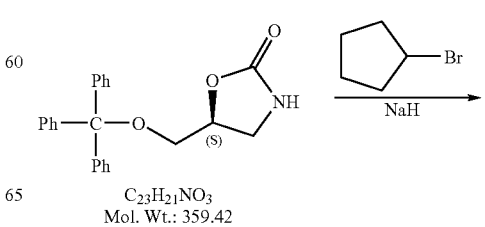

-continued

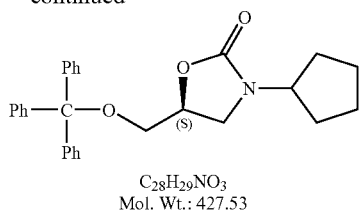

C28H29NO3
Mol. Wt.: 427.53

For C18,

| Materials | MW | Wt/V | mMol | Equiv |
|---|---|---|---|---|
| SM | 359.42 | 0.5 g | 1.39 | 1 |
| C19 | 149 | 414 mg | 2.78 | 2 |
| NaH (60%) | 24 | 100 mg | 2.57 | 1.8 |
| THF | | 4 mL | | |

NaH was added into the pre-cooled (by dry ice and acetone) the THF and SM solution, then stirred for two hours. C19 were added after re-cooled the reaction mixture.

Curtius Rearrangement:

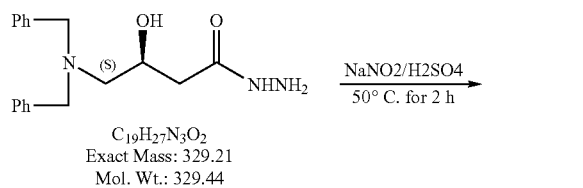

C19H27N3O2
Exact Mass: 329.21
Mol. Wt.: 329.44

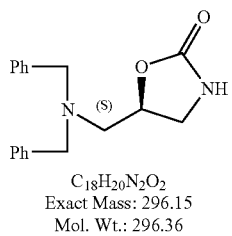

C18H20N2O2
Exact Mass: 296.15
Mol. Wt.: 296.36

| Materials | d | MW | Wt/V | mMol | Equiv |
|---|---|---|---|---|---|
| SM | | 329.44 | 26 | 79 | 1 |
| H2SO4 | | 98 | 9.2 mL | 95 | 1.2 |
| NaNO2 | | 69 | 8.2 g | 118 | 1.5 |
| water | | | 100 mL | | |

Procedure:

1). The hydrazide compound was dissolved in water (75 mL), and concentrated sulfuric acid (9.2 mL) diluted in water (25 mL) and added into the stirred solution. The mixture was cooled in the ice bath and then NaNO₂ in water (20 mL) was added dropwise.

2). The reaction mixture was stirred at room temperature for overnight. Then was put on the water rota-vap without vacuum to shake for 6 hours at 50° C.

3). The reaction was neutralized by sodium carbonate and extracted with EtOAc three times, brine and dried over Na₂SO₄.

4). The solvents were removed by water rota-vap to afford residues.

5). Column chromatograph to isolate the desired compound.

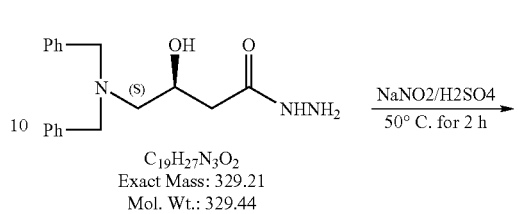

C19H27N3O2
Exact Mass: 329.21
Mol. Wt.: 329.44

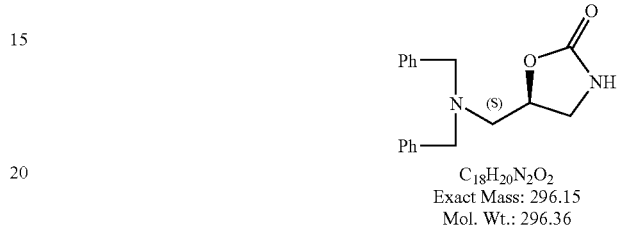

C18H20N2O2
Exact Mass: 296.15
Mol. Wt.: 296.36

| Materials | d | MW | Wt/V | mMol | Equiv |
|---|---|---|---|---|---|
| SM | | 329.44 | 4.5 g | | 1 |
| H2SO4 | | 98 | 1.6 mL | | 1.2 |
| NaNO2 | | 69 | 1.4 g | | 1.5 |
| water | | | 30 mL | | |

Procedure:

1). The hydrazide compound was dissolved in water (25 mL), and concentrated sulfuric acid (1.6 mL) diluted in water (5 mL) and added into the stirred solution. The mixture was cooled in the ice bath and then NaNO₂ powder was added directly.

2). The reaction mixture was stirred at room temperature for overnight. Then was put on the water rota-vap without vacuum to shake for 6 hours at 50° C.

3). The reaction was neutralized by sodium carbonate and extracted with EtOAc three times, brine and dried over Na₂SO₄.

4). The solvents were removed by water rota-vap to afford residues.

5). Column chromatographed to isolate the desired compound.

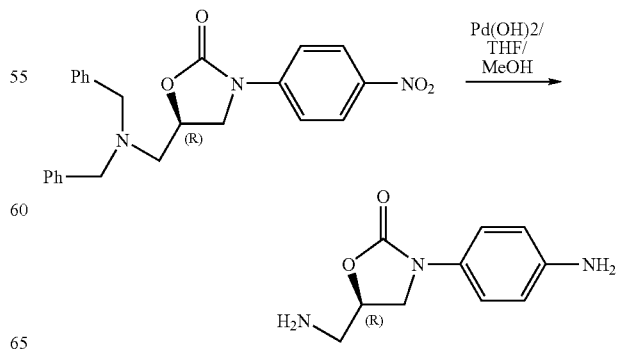

300 mg of ZD3-75-2

500 mg of Pd(OH)$_2$ 5 mL of THF 5 mL of MeOH

The reaction was stirred at room temperature 10 mins (see new spot and starting material on TLC, new spot is more polar) and 40 mins (see one new spot, which is less polar than starting material, and only one spot shown on TLC).

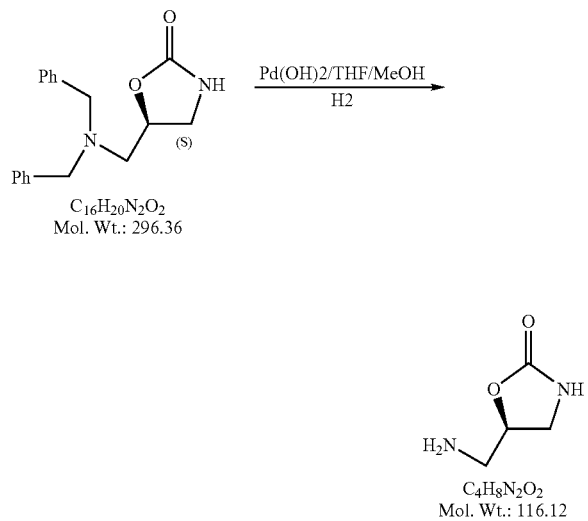

300 mg of ZD3-75-2

500 mg of Pd(OH)$_2$ 5 mL of THF 5 mL of MeOH

The reaction was stirred at room temperature 10 mins (see new spot and starting material on TLC, new spot is more polar) and 40 mins (see one new spot, which is less polar than starting material, and only one spot shown on TLC).

To a solution of starting material in THF, Et3N was added then BB3 was added. The reaction was stirred for overnight. Isolated by parp-TLC (3/1=EtOAc/Hexane) a Library:

Oxazolidinone derivatives: SC1, H, SG3-N, RG3, RC3 (0.1 nmol CH$_2$Cl$_2$ solution except H in THF)

Nitrobenzene derivatives: BB3, BB7, BB8, BB9 ((0.1 nmol CH$_2$Cl$_2$ solution except BB7 in THF)

Base: triethylamine (0.15 nmol)

The reactions were set up in the usual way and kept for overnight. Isolated by parp-TLC (3/1=EtOAc/Hexane).

Library

New M compounds:

Oxazolidinone derivatives: RG3, RC5, RC3

(0.1 nmol CH$_2$Cl$_2$ solution)

Nitrobenzene derivatives: M42, M43, M44, M45, M46, M47

(0.1 nmol) DIAD=0.10 nM in THF (MW 202), 1 equiv.

Ph$_3$P-polystyrene 1 mmol/g 100 mg for each compound 0.1 mMol

Procedure:

7. The vials were charged with SM and Ph$_3$P-polystrene.
8. A solution of DIAD in THF was added into the reaction mixture.

The reactions were stirred for overnight.

The reactions were set up in the usual way and kept for overnight. Isolated by parp-TLC (3/1=EtOAc/Hexane).

Alkylation: (By t-BuOK)

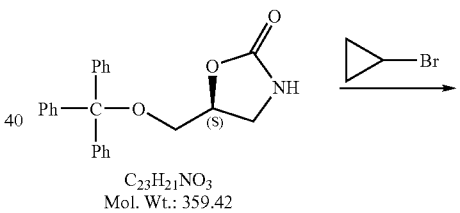

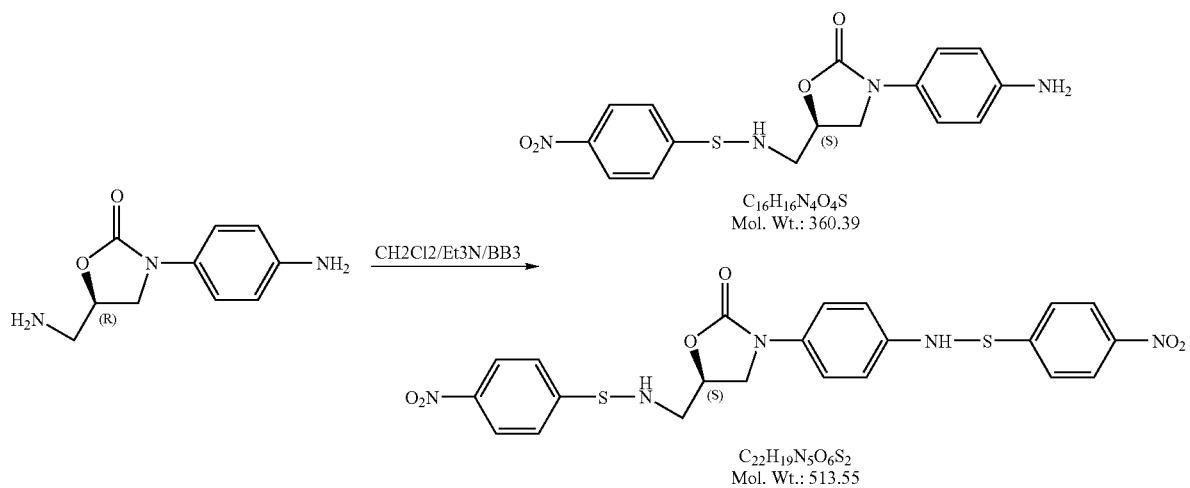

-continued

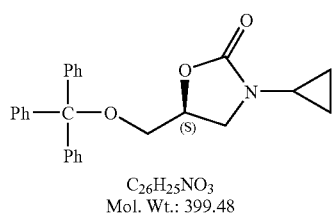

C26H25NO3
Mol. Wt.: 399.48

For C18,

| Materials | MW | Wt/V | mMol | Equiv |
|---|---|---|---|---|
| SM | 359.42 | 0.5 g | 1.39 | 1 |
| C18 (d1.5) | 120 | 0.2 mL | 2.78 | 2 |
| t-BuOK | | 3 mL | 2.57 | 1.8 |
| THF | | 5 mL | | |

To a solution of SM and THF was added t-BuOK, then C19 was added. The reaction mixture was heated up to 60° C. in sealed tube.

Alkylation: (By t-BuOK)

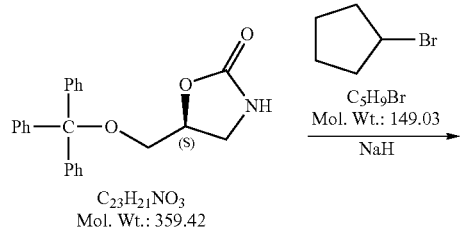

C23H21NO3
Mol. Wt.: 359.42

C5H9Br
Mol. Wt.: 149.03
NaH

C28H29NO3
Mol. Wt.: 427.53

For C19,

| Materials | MW | Wt/V | mMol | Equiv |
|---|---|---|---|---|
| SM | 359.42 | 0.5 g | 1.39 | 1 |
| C19 | 149 | 414 mg | 2.78 | 2 |
| t-BuOK | | 3 mL | 2.57 | 1.8 |
| THF | | 5 mL | | |

To a solution of SM and THF was added t-BuOK, then C19 was added. The reaction mixture was heated up to 60° C. in sealed tube.

Alkylation: (By t-BuOK)

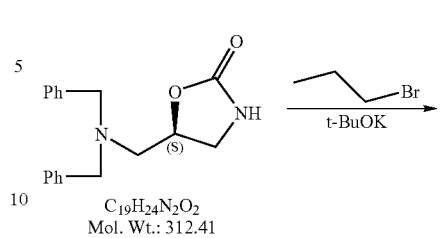

C19H24N2O2
Mol. Wt.: 312.41

C21H26N2O2
Mol. Wt.: 338.44

For C18,

| Materials | MW | Wt/V | mMol | Equiv |
|---|---|---|---|---|
| SM | 359.42 | 0.5 g | 1.39 | 1 |
| C18 (d1.5) | 120 | 0.2 mL | 2.78 | 2 |
| t-BuOK | | 3 mL | 2.57 | 1.8 |
| THF | | 5 mL | | |

To a solution of SM and THF was added t-BuOK, then C19 was added. The reaction mixture was heated up to 60° C. in sealed tube.

Library Linkage:

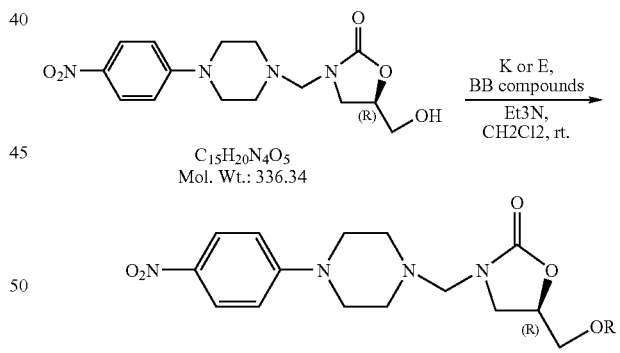

C15H20N4O5
Mol. Wt.: 336.34

ZD4-55-1

Starting material: 22 mg for each reaction K2, K91, K92, K95, K96, K97, K100, K101, K117, E183, E184, BB3, BB7, BB9, BB5, K93, K98, K94, K106, AC2, AC3, AC5, AC7.

Procedure:

0.08 mol of starting material 0.15 mmol of Et₃N 0.09 mmol of K and BB, AC or E compounds.

The reactions were stirred for weekend.

Library Linkage:

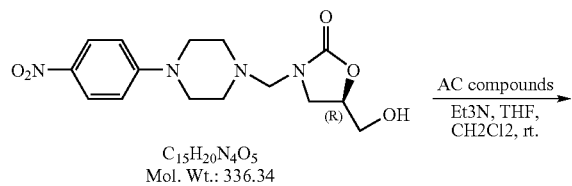

ZD4-55-1

Starting material: 14 mg for each reaction.

AC1, AC4, AC8, AC9, AC10, AC11, AC12, MsCl

Procedure:

0.04 mmol of starting material 0.15 mmol of Et$_3$N 0.06 mmol of AC compounds.

The reactions were stirred for overnight.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A compound having the formula

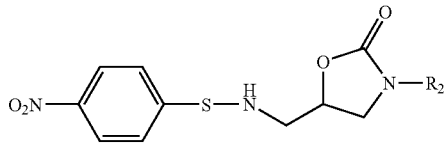

wherein R$_2$ is alkyl selected from the group consisting of methyl, ethyl and isopropyl moieties.

2. The compound of claim 1 wherein the alkyl is ethyl.
3. The compound of claim 1 wherein the alkyl is isopropyl.
4. The compound of claim 1 wherein the alkyl is methyl.
5. A compound having the formula

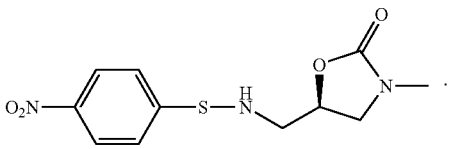

* * * * *

UNITED STATES PATENT AND TRADEMARK OFFICE
CERTIFICATE OF CORRECTION

PATENT NO. : 7,390,825 B2
APPLICATION NO. : 10/272877
DATED : June 24, 2008
INVENTOR(S) : Rawle I. Hollingsworth et al.

It is certified that error appears in the above-identified patent and that said Letters Patent is hereby corrected as shown below:

Column 6, line 2, "Pd(OAc)2" should be --Pd(OAc)$_2$--.

Column 7, line 55, " 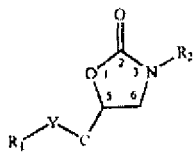 " should be -- 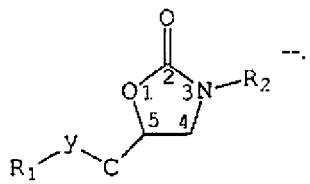 --.

Column 71, line 58, "MS" should be --M5--.

Column 72, line 33, " 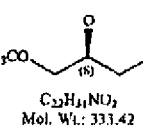 " should be -- 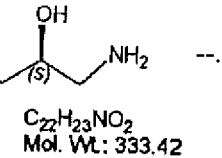 --.

Column 96, line 1, "(17)41" should be --(17)4i--.

Column 107, line 22, "= 4" should be --= $^1/_4$--.

Column 107, line 37, " 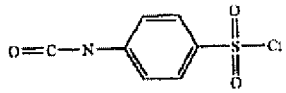 " should be -- $Ph_3CO$ ... $NH_2$ $C_{22}H_{23}NO_2$ Mol. Wt.: 333.42 --.

Column 111, line 30, "$C_{19}H_{16}FN_3O_5$" should be --$C_{19}H_{18}FN_3O_5$--.

Column 121, line 8, In the table under column Wt/V for material THF, please insert --1 mL--.

Column 125, line 54, "MS" should be --M5--.

Column 128, line 45, "Ph3P" should be --Ph$_3$P--.

Column 134, line 53, "$C_{16}H_{20}N_2O_2$" should be --$C_{18}H_{20}N_2O_2$--.

Column 141, line 55, "CH2" should be --CH20--.

Column 142, line 64, "$C_9H_{15}N_2O_3$" should be --$C_9H_{16}N_2O_3$--.

Column 144, lines 51-65, "  " should be -- 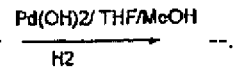 --.

UNITED STATES PATENT AND TRADEMARK OFFICE
CERTIFICATE OF CORRECTION

PATENT NO. : 7,390,825 B2
APPLICATION NO. : 10/272877
DATED : June 24, 2008
INVENTOR(S) : Rawle I. Hollingsworth et al.

It is certified that error appears in the above-identified patent and that said Letters Patent is hereby corrected as shown below:

Column 145, line 21, "$C_{16}H_{20}N_2O_2$" should be --$C_{18}H_{20}N_2O_2$"--.

Column 145, lines 25-33, " 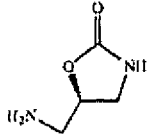 " should be -- 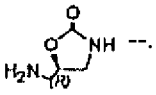 --.

Signed and Sealed this

Twenty-fifth Day of August, 2009

David J. Kappos
*Director of the United States Patent and Trademark Office*